(12) United States Patent
Vincent et al.

(10) Patent No.: US 9,617,320 B2
(45) Date of Patent: Apr. 11, 2017

(54) NUCLEIC ACIDS ENCODING FHL1 MUTATIONS ASSOCIATED WITH NOVEL X-LINKED MUSCULAR MYOPATHIES AND METHODS OF SCREENING A SUBJECT

(71) Applicant: CENTRE FOR ADDICTION AND MENTAL HEALTH, Toronto (CA)

(72) Inventors: John Vincent, Toronto (CA); Christian Windpassinger, Graz (AT); Stefan Quasthoff, Graz (AT)

(73) Assignee: Centre for Addiction and Mental Health, Toronto, Ontario (CA)

( * ) Notice: Subject to any disclaimer, the term of this patent is extended or adjusted under 35 U.S.C. 154(b) by 0 days.

(21) Appl. No.: 14/835,869

(22) Filed: Aug. 26, 2015

(65) Prior Publication Data

US 2016/0002309 A1 Jan. 7, 2016

Related U.S. Application Data

(63) Continuation of application No. 14/077,887, filed on Nov. 12, 2013, now Pat. No. 9,150,923, which is a continuation of application No. 12/663,221, filed as application No. PCT/CA2008/001062 on Jun. 4, 2008, now Pat. No. 8,580,502.

(60) Provisional application No. 60/933,251, filed on Jun. 4, 2007.

(51) Int. Cl.
| | |
|---|---|
| *C07K 14/47* | (2006.01) |
| *G01N 33/68* | (2006.01) |
| *C12Q 1/68* | (2006.01) |
| *G01N 33/566* | (2006.01) |

(52) U.S. Cl.
CPC .......... *C07K 14/4707* (2013.01); *C07K 14/47* (2013.01); *C12Q 1/6883* (2013.01); *G01N 33/566* (2013.01); *G01N 33/6893* (2013.01); *G01N 33/6896* (2013.01); *G01N 2800/2878* (2013.01); *G01N 2800/325* (2013.01)

(58) Field of Classification Search
CPC .. C07K 14/47; C07K 14/4707; C12Q 1/6883; G01N 33/566; G01N 33/6893; G01N 33/6896; G01N 2800/2878; G01N 2800/325
See application file for complete search history.

(56) References Cited

U.S. PATENT DOCUMENTS

2005/0202421 A1 9/2005 Hirsch et al.

FOREIGN PATENT DOCUMENTS

| WO | 89/06286 A2 | 7/1989 |
| WO | WO2005/113812 | * 12/2005 |

OTHER PUBLICATIONS

Kim et al., "Forkhead-associated Domains of the Tobacco NtFHA1 Transcription Activator and Yeast Fhl1 Forkhead Transcription Factor Are Functionally Conserved," J. Biol. Chem., 277(41):38781-38790 (Oct. 11, 2002).
Taylor et al., "Current and Emerging Techniques for Diagnostic Mutation Detection," Methods in Molecular Medicine, Molecular Diagnosis of Genetic Diseases, 92:9-44 (2004).
Wakai et al., "A novel method of identifying genetic mutations using an electrochemical DNA array," Nucleic Acids Research, 32(18):e141 (10 pages) (Oct. 21, 2004).
International Search Report and Written Opinion, PCT/CA2008/001062, Aug. 29, 2008.
Bione et al., "Identification of a novel X-linked gene responsible for Emery-Dreifuss muscular dystrophy," Nature Genetics, 8:323-327 (1994).
Blanco et al., "The kyphoscoliosis (ky) mouse is deficient in hypertrophic responses and is caused by a mutation in a novel muscle-specific protein," Human Molecular Genetics, 10(1):9-16 (2001).
Carsana et al., "A Larger Spectrum of Intragenic Short Tandem Repeats Improves Linkage Analysis and Localization of Intragenic Recombination Detection in the Dystrophin Gene. An Analysis of 93 Families from Southern Italy," Journal of Molecular Diagnostics, 9(1):64-69 (Feb. 2007).
Davies et al., "Molecular mechanisms of muscular dystrophies: old and new players," Nature Reviews Molecular Cell Biology, 7:762-773 (Oct. 2006).
Ellis, "Visions & Reflections (Minireview). Emery-Dreifuss muscular dystrophy at the nuclear envelope: 10 years on," Cell. Mol. Life Sci., 63:2702-2709 (2006).
Ervasti, "Dystrophin, its interactions with other proteins, and implications for muscular dystrophy," Biochimica et Biophysica Acta, 1772:108-117 (2007).
Fukuda, "Biogenesis of the Lysosomal Membrane," Subcellular Biochemistry, 22:199-230 (1994).
Fukuda et al., "Cloning of cDNAs Encoding Human Lysosomal Membrane Glycoproteins, h-lamp-1 and h-lamp-2," Journal of Biological Chemistry, 263(35):18920-18928 (Dec. 15, 1988).
Gecz et al., "Fibroblast growth factor homologous factor 2 (FHF2): gene structure, expression and mapping to the Börjeson-Forssman-Lehmann syndrome region in Xq26 delineated by a duplication breakpoint in a BFLS-like patient," Hum Genet, 104:56-63 (1999).
"GeneChip Human Mapping 500K Array Set," Affymetrix Product Family, pp. 1-4 (2006).
Gudbjartsson et al., "Allegro, a new computer program for multipoint linkage analysis," Nature Genetics, 25:12-13 (2000).
Hauser et al., "Identification of isoforms of the exocytosis-sensitive phosphoprotein PP63/parafusin in Paramecium tetraurelia and demonstration of phosphoglucomutase activity," Biochemical Journal, 323:289-296 (1997).
Ho et al., "Isolation of the Gene for McLeod Syndrome that Encodes a Novel Membrane Transport Protein," Cell, 77:869-880 (Jun. 17, 1994).
Hoffman et al., "easyLINKAGE-Plus-automated linkage analyses using large-scale SNP data," Bioinformatics, 21(17):3565-3567 (Sep. 1, 2005).

(Continued)

*Primary Examiner* — Robert Landsman
(74) *Attorney, Agent, or Firm* — Winston & Strawn LLP

(57) ABSTRACT

Four and a Half LIM domains protein 1 (FHL-1) mutations at positions 128 or 224 that are associated with X-linked muscular myopathy, methods of screening subjects to identify those susceptible to muscular myopathy including muscular dystrophy and cardiomyopathy and kits.

16 Claims, 21 Drawing Sheets

(56) References Cited

OTHER PUBLICATIONS

Holaska et al., "Lmo7 is an emerin-binding protein that regulates the transcription of emerin and many other muscle-relevant genes," Human Molecular Genetics, 15(23):3459-3472 (2006).

Kadrmas et al., "The LIM domain: From the Cytoskeleton to the Nucleus," Nat Rev Mol Cell Biol., 5(11):920-931 (Nov. 5, 2004).

Lee et al., "Chromosomal mapping, tissue distribution and cDNA sequence of Four-and-a-half LIM domain protein 1 (FHL1)," Gene, 216:163-170 (1998).

Lee et al., "Characterization of a brain-specific nuclear LIM domain protein (FHL1B) which is an alternatively spliced variant of FHL1," Gene, 237:253-263 (1999).

Maeda et al., "Mammalian Vestigial-like 2, a Cofactor of TEF-1 and MEF2 Transcription Factors that Promotes Skeletal Muscle Differentiation," Journal of Biological Chemistry, 277(50):48889-48898 (Dec. 13, 2002).

Marsh et al., "Elevated Serum Creatine Phosphokinase in Subjects with McLeod Syndrome," Vox Sang., 40:403-411 (1981).

McGrath et al., "Skeletal muscle LIM protein 1 (SLIM1/FHL1) induces a5β1-integrin-dependent myocyte elongation," Am J Physiol Cell Physiol, 285:C1513-C1526 (2003).

McGrath et al., "Four and a Half LIM Protein 1 Binds Myosin-binding Protein C and Regulates Myosin Filament Formation and Sarcomere Assembly," The Journal of Biological Chemistry, 281(11):7666-7683 (2006).

Miller et al., "Recruitment of human muscleblind proteins to (CUG)n expansions associated with myotonic dystrophy," EMBO Journal, 19(17):4439-4448 (2000).

Morris et al., "Molecular Genetics of Emery-Dreifuss Muscular Dystrophy," in Encyclopedia of Life Sciences (ELS), pp. 1-7, John Wiley & Sons, Ltd., Chichester (Sep. 2010).

Nowak et al., "Mutations in the skeletal muscle α-actin gene in patients with actin myopathy and nemaline myopathy," Nature Genetics, 23:208-2012 (1999).

Quinzii et al., "X-Linked Dominant Scapuloperoneal Myopathy is Due to a Mutation in the Gene Encoding Four-and-a-Half-LIM Protein 1," The American Journal of Human Genetics, 82:208-213 (Jan. 2008).

Schadt et al., "Feature Extraction and Normalization Algorithms for High-Density Oligonucleotide Gene Expression Array Data," Journal of Cellular Biochemistry Supplement, 37:120-125 (2001).

Schessl et al., "Proteomic identification of FHL1 as the protein mutated in human reducing body myopathy," J. Clin. Invest., 118:904-912 (2008).

Talra et al., "Role of the LIM class homeodomain protein Xlim-1 in neural and muscle induction by the Spemann organizer in Xenopus," Nature, 372:677-679 (1994).

Vaudin et al., "TONDU (TDU), a novel human protein related to the product of vestigial (vg) gene of *Drosophila melanogaster* interacts with vertebrate TEF factors and substitutes for Vg function in wing formation," Development, 126:4807-4816 (1999).

Windpassinger et al., "An X-Linked Myopathy with Postural Muscle Atrophy and Generalized Hypertrophy, Termed XMPMA, is Caused by Mutations in FHL1," The American Journal of Human Genetics, 82:88-99 (Jan. 2008).

Yasuda et al., "Dystrophic heart failure blocked by membrane sealant poloxamer," Nature, 436(7053):1025-1029 (Aug. 18, 2005).

Zheng et al., "The diverse biofunctions of LIM domain proteins: determined by subcellular localization and protein-protein interaction," Biol. Cell, 99:489-502 (2007).

Stratagene Catalog, p. 39 (1988).

U.S. Appl. No. 12/663,221, Restriction Requirement, Aug. 23, 2010.

U.S. Appl. No. 12/663,221, Non-Final Office Action, Oct. 15, 2010.

U.S. Appl. No. 12/663,221, Final Office Action, Mar. 25, 2011.

U.S. Appl. No. 12/663,221, Notice of Allowance, Jul. 12, 2013.

U.S. Appl. No. 14/077,887, Restriction Requirement, Oct. 10, 2014.

U.S. Appl. No. 14/077,887, Non-Final Office Action, Jan. 2, 2015.

U.S. Appl. No. 14/077,887, Final Office Action, Apr. 20, 2015.

U.S. Appl. No. 14/077,887, Notice of Allowance, Jun. 2, 2015.

\* cited by examiner

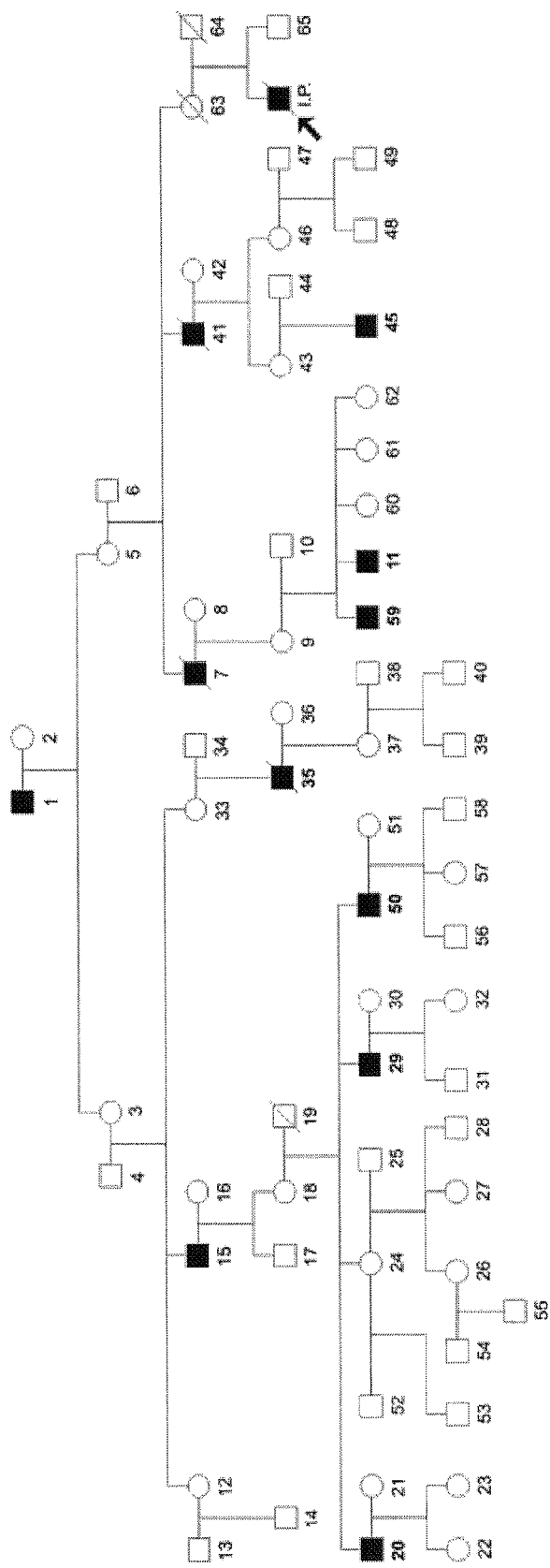
Fig. 1A. Pedigree of the X-recessive postural muscular myopathy family.

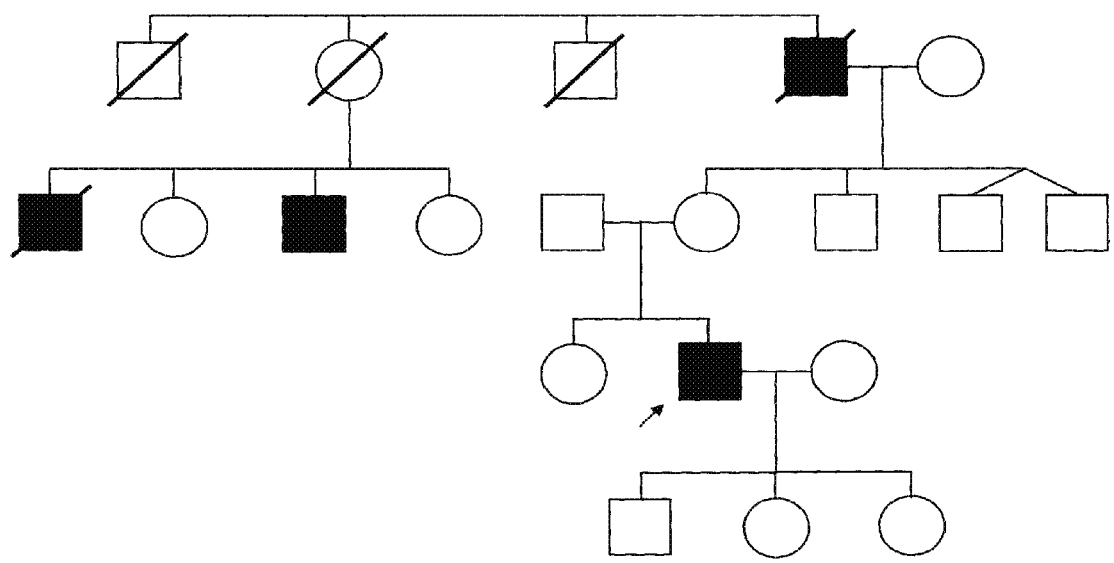
Figure 1B. UK family 2 pedigree.

Figure 1C. UK family 3 pedigree: c.381_382insATC; p.Phe127_Thr128insIle
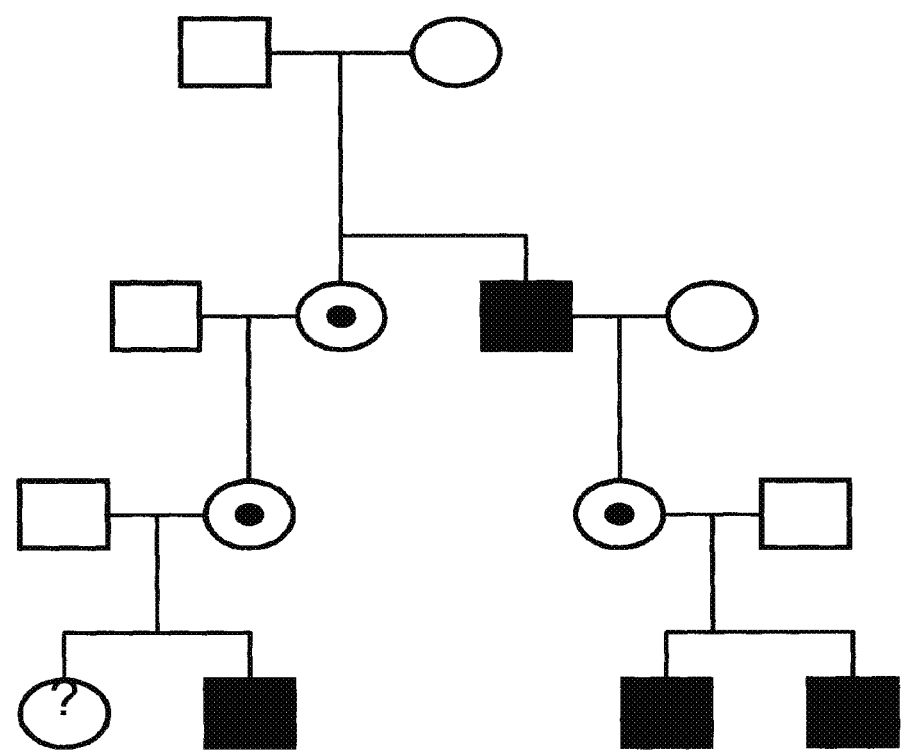

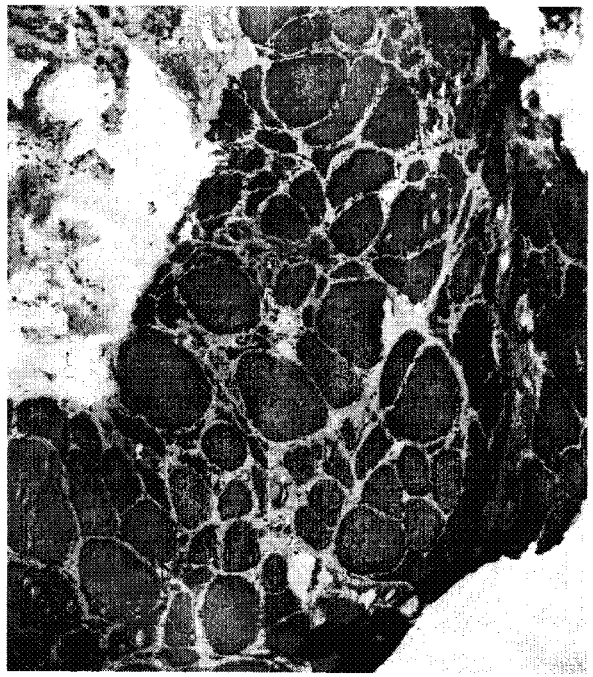
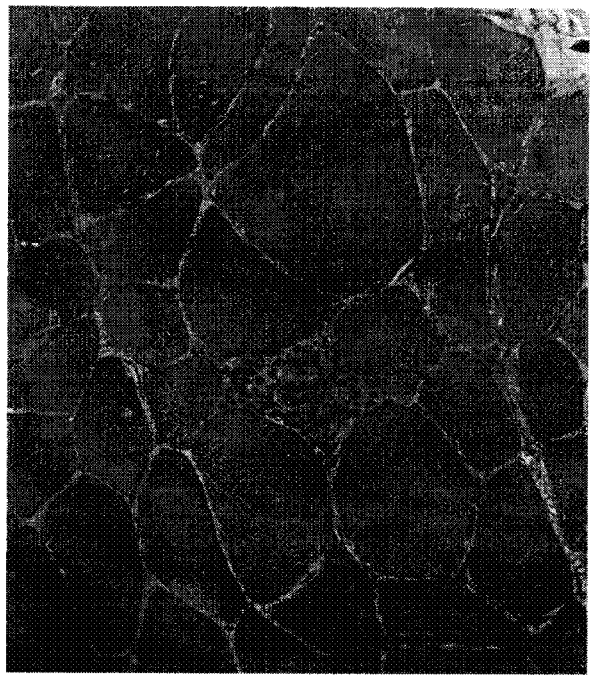
Fig. 3

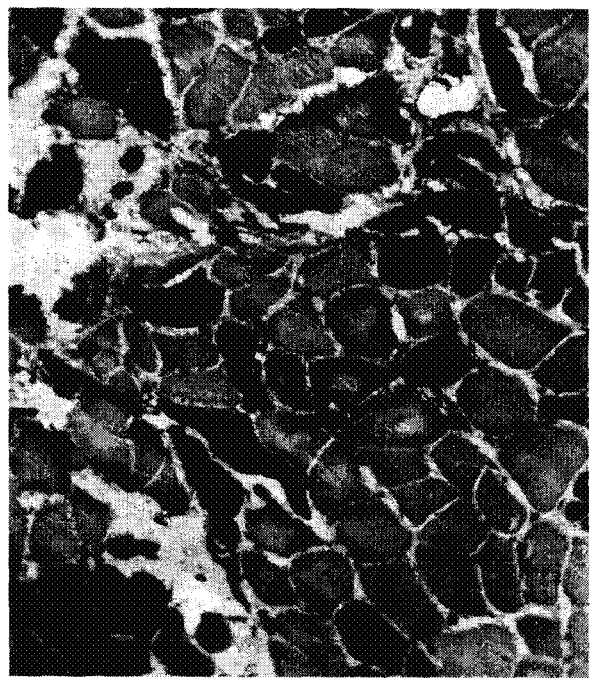
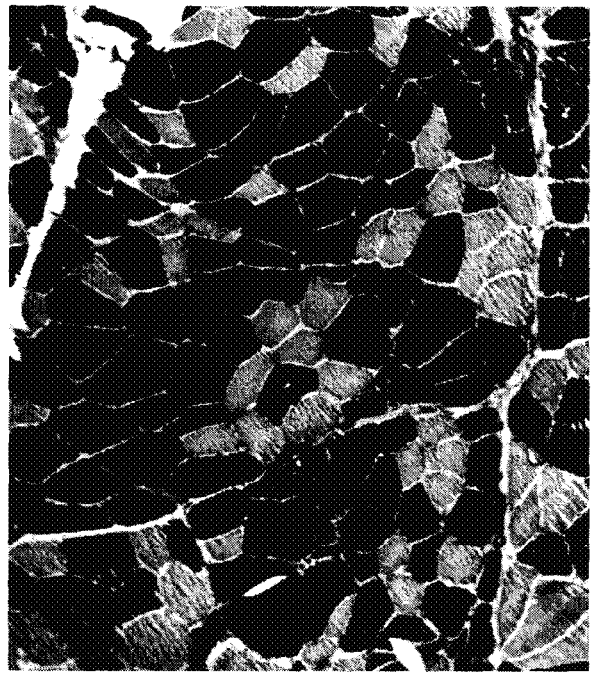
Fig. 4

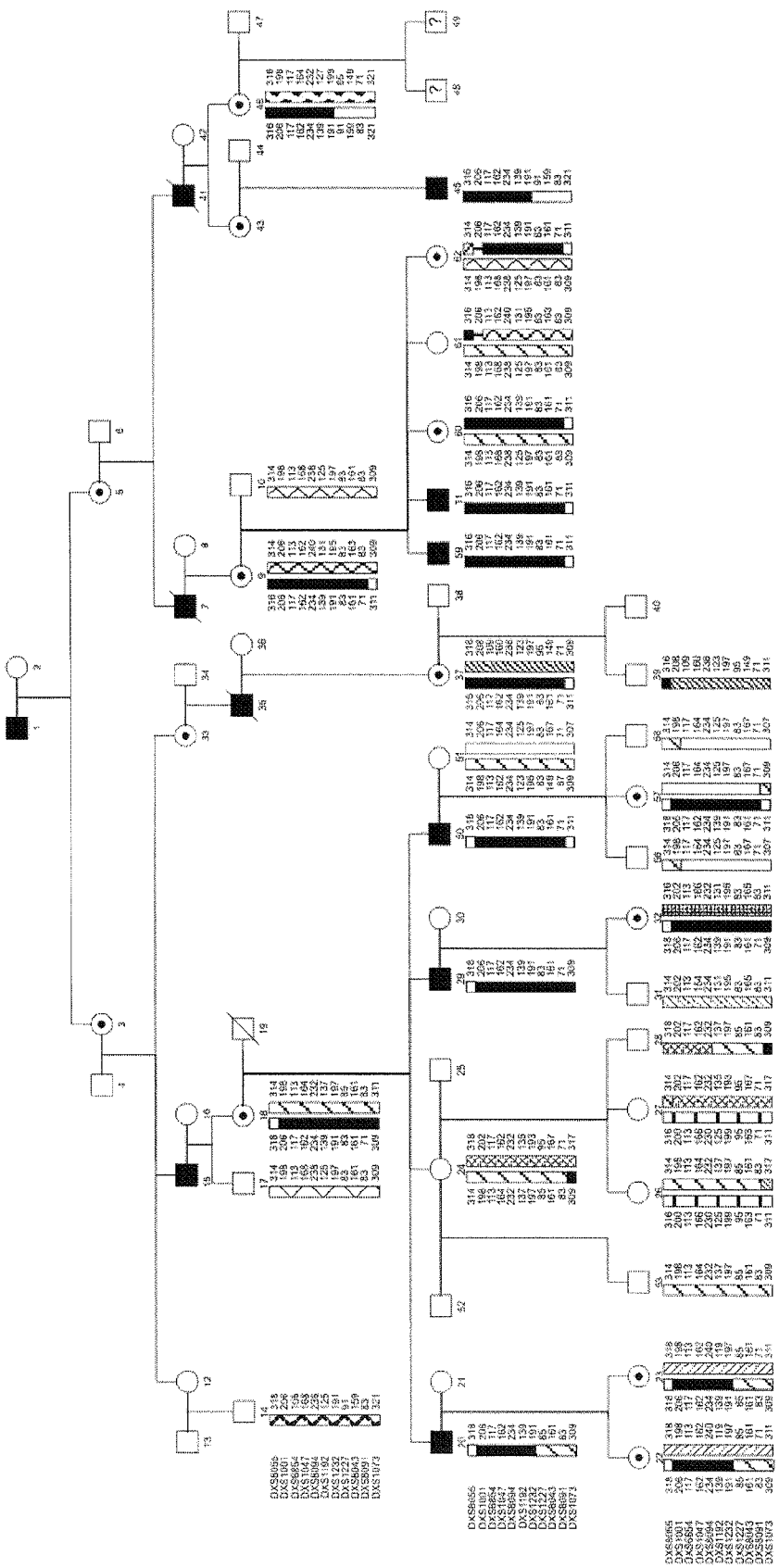
Fig. 5. Linkage analysis to the DMD locus using polymorphic STR intragenic markers STR-44, STR-45, STR-48, STR-49 and STR-50 revealed different haplotypes in the affecteds, conclusively excluding the DMD locus. Recombination of markers STR-44, STR-48, STR-49, and STR-50 is evident, as illustrated by haplotypes. Error!

Fig. 6. Ideogrammatic representation of the XMPMA locus on the distal arm of chromosome X, the electropherograms indicating the wild-type and mutation sequence for the Austrian XMPMA family, and the secondary structure of FHL1, indicating the position of the resulting amino acid substitution, C224W, relative to structural features in the protein.

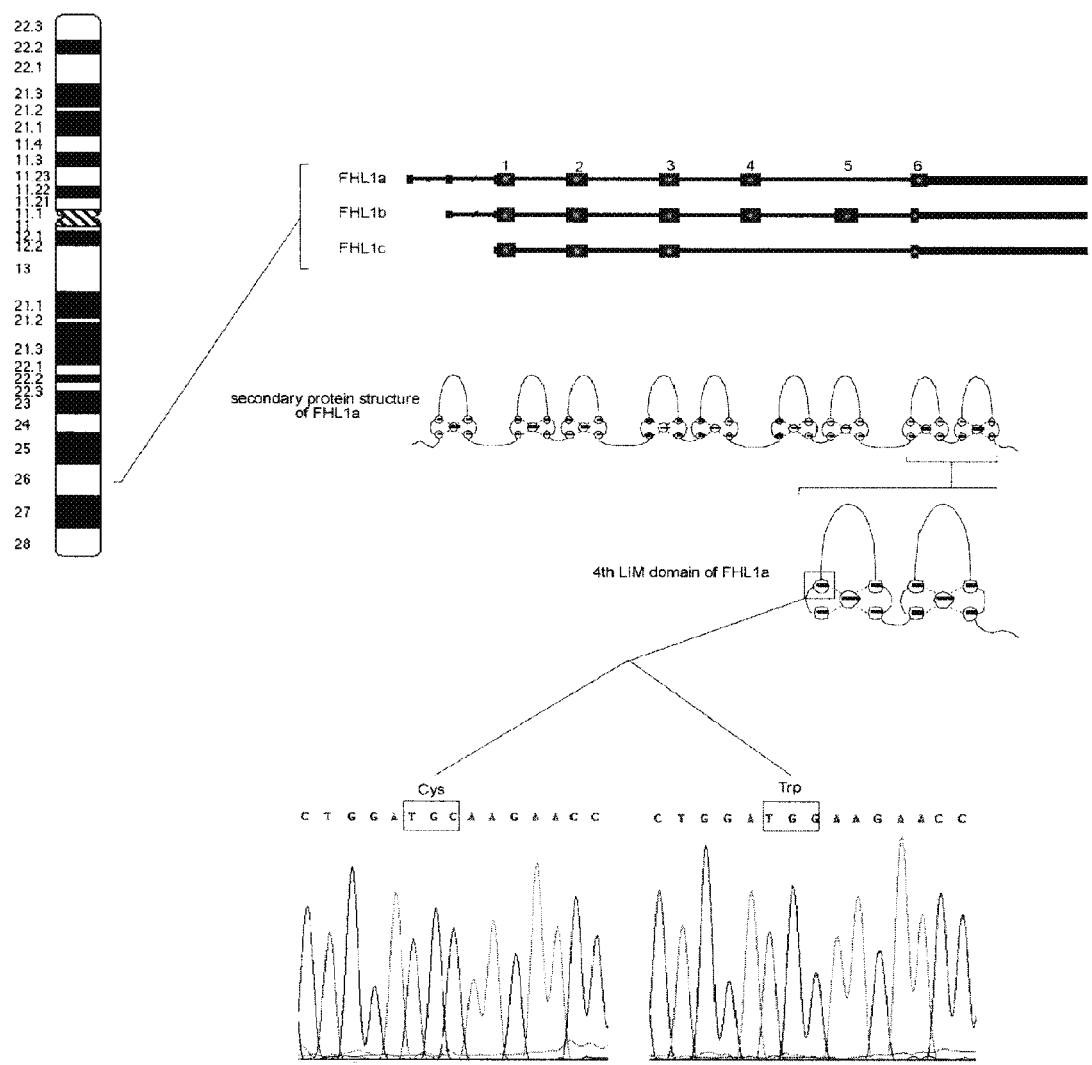

MAEKFDCHYCRDPLQGKKYVQKDGHHCC LKC FDKFC ANTC VEC RKPIGADSKEVHYKNRF
WHDTCFRCAKCLHPLANETFVAKDNKILC NKCTTREDSPKC KGC FKAIVAGDQNVEYKGT
VWH KDC FTC SNC KQVIGTGSFFPKGEDFYC VTC HETKFAKHC VKC NKAITSGGITYQDQP
WHADCFVCVTC SKKLAGQRFTAVEDQYYC VDCYKNFVAKKC AGC KNPITGFGKGSSVVAY
EGQSWHDYCFHCKKC SVNLANKRFVFHQEQVYC PDCAKKL

FIGURE 7

Human FHL1 isoform a and isoform b shared sequence

MAEKFDCHYCRDPLQGKKYVQKDGHHCCLKCFDKFCANTCVECRKPIGADSKEVHYKNRFWH
DTCFRCAKCLHPLANETFVAKDNKILCNKCTTREDSPKCKGCFKAIVAGDQNVEYKGTVWHKD
CFTCSNCKQVIGTGSFFPKGEDFYCVTCHETKFAKHCVKCNKAITSGGITYQDQPWHADCFVCV
TCSKKLAGQRFTAVEDQYYCVDCYKNFVAKKCAGXKNPITG (SEQ ID NO:1)

C224W mutation in human FHL1 isoform a (W is underlined)

MAEKFDCHYCRDPLQGKKYVQKDGHHCCLKCFDKFCANTCVECRKPIGADSKEVHYKNRFWH
DTCFRCAKCLHPLANETFVAKDNKILCNKCTTREDSPKCKGCFKAIVAGDQNVEYKGTVWHKD
CFTCSNCKQVIGTGSFFPKGEDFYCVTCHETKFAKHCVKCNKAITSGGITYQDQPWHADCFVCV
TCSKKLAGQRFTAVEDQYYCVDCYKNFVAKKCAG<u>W</u>KNPITGFGKGSSVVAYEGQSWHDYCFH
CKKCSVNLANKRFVFHQEQVYCPDCAKKL (SEQ ID NO:2)

C224W mutation in human FHL1 isoform b (W is underlined)

MAEKFDCHYCRDPLQGKKYVQKDGHHCCLKCFDKFCANTCVECRKPIGADSKEVHYKNRFWH
DTCFRCAKCLHPLANETFVAKDNKILCNKCTTREDSPKCKGCFKAIVAGDQNVEYKGTVWHKD
CFTCSNCKQVIGTGSFFPKGEDFYCVTCHETKFAKHCVKCNKAITSGGITYQDQPWHADCFVCV
TCSKKLAGQRFTAVEDQYYCVDCYKNFVAKKCAG<u>W</u>KNPITGKRTVSRVSRPVSKARKPPVCHG
KRLPLTLFPSANLRGRHPGGERTCPSWVVVLYRKNRSLAAPRGPGLVKAPVWWPMKDNPGTTT
ASTAKNAP (SEQ ID NO:3)

species/isoform conserved sequence

VAKKCX$_1$GX$_2$X$_3$NPIT (SEQ ID NO:4)

Representative mRNA encoding mutant human FHL1 isoform a; mutation of X (underlined) to
nucleotide that results in C224W mutation associated with X-linked muscular myopathy CGGAGGGGGCTCAGTCCGCAGCCGCCGCCGCCACCGCCGCGCCTCGGCCTCGGTGCAGGCA
GCGGCCGCCGCCGCCGAGACAGCTGCGCGGGCGAGCATCCCCACGCAGCACCTTGGAAGTT
GTTTTCAACCATATCCAGCCTTTGCCGAATACATCCTATCTGCCACACATCCAGCGTGAGGTC FIGURE 7 (continued)

CCTCCAGCTACAAGGTGGGCACCATGGCGGAGAAGTTTGACTGCCACTACTGCAGGGATCCC
TTGCAGGGGAAGAAGTATGTGCAAAAGGATGGCCACCACTGCTGCCTGAAATGCTTTGACAA
GTTCTGTGCCAACACCTGTGTGGAATGCCGCAAGCCCATCGGTGCGGACTCCAAGGAGGTGC
ACTATAAGAACCGCTTCTGGCATGACACCTGCTTCCGCTGTGCCAAGTGCCTTCACCCCTTGG
CCAATGAGACCTTTGTGGCCAAGGACAACAAGATCCTGTGCAACAAGTGCACCACTCGGGAG
GACTCCCCCAAGTGCAAGGGGTGCTTCAAGGCCATTGTGGCAGGAGATCAAAACGTGGAGT
ACAAGGGGACCGTCTGGCACAAAGACTGCTTCACCTGTAGTAACTGCAAGCAAGTCATCGGG
ACTGGAAGCTTCTTCCCTAAAGGGGAGGACTTCTACTGCGTGACTTGCCATGAGACCAAGTT
TGCCAAGCATTGCGTGAAGTGCAACAAGGCCATCACATCTGGAGGAATCACTTACCAGGATC
AGCCCTGGCATGCCGATTGCTTTGTGTGTGTTACCTGCTCTAAGAAGCTGGCTGGGCAGCGT
TTCACCGCTGTGGAGGACCAGTATTACTGCGTGGATTGCTACAAGAACTTTGTGGCCAAGAA
GTGTGCTGGATG■AAGAACCCCATCACTGGGTTTGGTAAAGGCTCCAGTGTGGTGGCCTATG
AAGGACAATCCTGGCACGACTACTGCTTCCACTGCAAAAAATGCTCCGTGAATCTGGCCAAC
AAGCGCTTTGTTTTCCACCAGGAGCAAGTGTATTGTCCCGACTGTGCCAAAAAGCTGTAAAC
TGACAGGGGCTCCTGTCCTGTAAAATGGCATTTGAATCTCGTTCTTTGTGTCCTTACTTTCTG
CCCTATACCATCAATAGGGGAAGAGTGGTCCTTCCCTTCTTTAAAGTTCTCCTTCCGTCTTTT
CTCCCATTTTACAGTATTACTCAAATAAGGGCACACAGTGATCATATTAGCATTTAGCAAAA
AGCAACCCTGCAGCAAAGTGAATTTCTGTCCGGCTGCAATTTAAAAATGAAAACTTAGGTAG
ATTGACTCTTCTGCATGTTTCTCATAGAGCAGAAAAGTGCTAATCATTTAGCCACTTAGTGAT
GTAAGCAAGAAGCATAGGAGATAAAACCCCCACTGAGATGCCTCTCATGCCTCAGCTGGGAC
CCACCGTGTAGACACACGACATGCAAGAGTTGCAGCGGCTGCTCCAACTCACTGCTCACCCT
CTTCTGTGAGCAGGAAAAGAACCCTACTGACATGCATGGTTTAACTTCCTCATCAGAACTCT
GCCCTTCCTTCTGTTCTTTTGTGCTTTCAAATAACTAACACGAACTTCCAGAAAATTAACATT
TGAACTTAGCTGTAATTCTAAACTGACCTTTCCCCGTACTAACGTTTGGTTTCCCCGTGTGGC
ATGTTTTCTGAGCGTTCCTACTTTAAAGCATGGAACATGCAGGTGATTTGGGAAGTGTAGAA
AGACCTGAGAAAACGAGCCTGTTTCAGAGGAACATCGTCACAACGAATACTTCTGGAAGCTT
AACAAAACTAACCCTGCTGTCCTTTTTATTGTTTTTAATTAATATTTTTGTTTTAATTGATAGC
AAAATAGTTTATGGGTTTGGAAACTTGCATGAAAATATTTTAGCCCCCTCAGATGTTCCTGC
AGTGCTGAAATTCATCCTACGGAAGTAACCGCAAAACTCTAGAGGGGGAGTTGAGCAGGCG
CCAGGGCTGTCATCAACATGGATATGACATTTCACAACAGTGACTAGTTGAATCCCTTGTAA

FIGURE 7 (continued)
CGTAGTAGTTGTCTGCTCTTTGTCCATGTGTTAATGAGGACTGCAAAGTCCCTTCTGTTGTGA

TTCCTAGGACTTTTCCTCAAGAGGAAATCTGGATTTCCACCTACCGCTTACCTGAAATGCAGG

ATCACCTACTTACTGTATTCTACATTATTATATGACATAGTATAATGAGACAATATCAAAAGT

AAACATGTAATGACAATACATACTAACATTCTTGTAGGAGTGGTTAGAGAAGCTGATGCCTC

ATTTCTACATTCTGTCATTAGCTATTATCATCTAACGTTTCAGTGTATCCTTACAGAAATAAA

GCAGCATATGAAAAAAAAAAAAAAAAAAAAAAA (SEQ ID NO: 5);

Representative mRNA encoding mutant human FHL1 isoform b; mutation of X (underlined) to nucleotide that results in C224W mutation associated with X-linked muscular myopathy

TCCTATCTGCCACACATCCAGCGTGAGGTCCCTCCAGCTACAAGGTGGGCACCATGGCGGAG

AAGTTTGACTGCCACTACTGCAGGGATCCCTTGCAGGGGAAGAAGTATGTGCAAAAGGATG

GCCACCACTGCTGCCTGAAATGCTTTGACAAGTTCTGTGCCAACACCTGTGTGGAATGCCGC

AAGCCCATCGGTGCGGACTCCAAGGAGGTGCACTATAAGAACCGCTTCTGGCATGACACCTG

CTTCCGCTGTGCCAAGTGCCTTCACCCCTTGGCCAATGAGACCTTTGTGGCCAAGGACAACA

AGATCCTGTGCAACAAGTGCACCACTCGGGAGGACTCCCCCAAGTGCAAGGGGTGCTTCAAG

GCCATTGTGGCAGGAGATCAAAACGTGGAGTACAAGGGGACCGTCTGGCACAAAGACTGCT

TCACCTGTAGTAACTGCAAGCAAGTCATCGGGACTGGAAGCTTCTTCCCTAAAGGGGAGGAC

TTCTACTGCGTGACTTGCCATGAGACCAAGTTTGCCAAGCATTGCGTGAAGTGCAACAAGGC

CATCACATCTGGAGGAATCACTTACCAGGATCAGCCCTGGCATGCCGATTGCTTTGTGTGTG

TTACCTGCTCTAAGAAGCTGGCTGGGCAGCGTTTCACCGCTGTGGAGGACCAGTATTACTGC

GTGGATTGCTACAAGAACTTTGTGGCCAAGAAGTGTGCTGGATG▪AAGAACCCCATCACTGG

GAAAAGGACTGTGTCAAGAGTGAGCCGCCCAGTCTCTAAAGCTAGGAAGCCCCAGTGTGC

CACGGGAAACGCTTGCCTCTCACCCTGTTTCCCAGCGCCAACCTCCGGGGCAGGCATCCGGG

TGGAGAGAGGACTTGTCCCTCGTGGGTGGTGGTTCTTTATAGAAAAAATCGAAGCTTAGCAG

CTCCTCGTGGCCCGGGTTTGGTAAAGGCTCCAGTGTGGTGGCCTATGAAGGACAATCCTGGC

ACGACTACTGCTTCCACTGCAAAAAATGCTCCGTGAATCTGGCCAACAAGCGCTTTGTTTTCC

ACCAGGAGCAAGTGTATTGTCCCGACTGTGCCAAAAAGCTGTAA (SEQ ID NO:6)

FIGURE 7 (continued)
Human FHL1 isoform a

NM_001449

>gi|34147646|ref|NM_001449.3| Homo sapiens four and a half LIM domains
  1 (FHL1), mRNA

CGGAGGGGGCTCAGTCCGCAGCCGCCGCCGCCACCGCCGCGCCTCGGCCTCGGTGCAGGCAGCGGCCGCC

GCCGCCGAGACAGCTGCGCGGGCGAGCATCCCCACGCAGCACCTTGGAAGTTGTTTTCAACCATATCCAG

CCTTTGCCGAATACATCCTATCTGCCACACATCCAGCGTGAGGTCCCTCCAGCTACAAGGTGGGCACCAT

GGCGGAGAAGTTTGACTGCCACTACTGCAGGGATCCCTTGCAGGGGAAGAAGTATGTGCAAAAGGATGGC

CACCACTGCTGCCTGAAATGCTTTGACAAGTTCTGTGCCAACACCTGTGTGGAATGCCGCAAGCCCATCG

GTGCGGACTCCAAGGAGGTGCACTATAAGAACCGCTTCTGGCATGACACCTGCTTCCGCTGTGCCAAGTG

CCTTCACCCCTTGGCCAATGAGACCTTTGTGGCCAAGGACAACAAGATCCTGTGCAACAAGTGCACCACT

CGGGAGGACTCCCCCAAGTGCAAGGGGTGCTTCAAGGCCATTGTGGCAGGAGATCAAAACGTGGAGTACA

AGGGGACCGTCTGGCACAAAGACTGCTTCACCTGTAGTAACTGCAAGCAAGTCATCGGGACTGGAAGCTT

CTTCCCTAAAGGGGAGGACTTCTACTGCGTGACTTGCCATGAGACCAAGTTTGCCAAGCATTGCGTGAAG

TGCAACAAGGCCATCACATCTGGAGGAATCACTTACCAGGATCAGCCCTGGCATGCCGATTGCTTTGTGT

GTGTTACCTGCTCTAAGAAGCTGGCTGGGCAGCGTTTCACCGCTGTGGAGGACCAGTATTACTGCGTGGA

TTGCTACAAGAACTTTGTGGCCAAGAAGTGTGCTGGATG▊AAGAACCCCATCACTGGGTTTGGTAAAGGC

TCCAGTGTGGTGGCCTATGAAGGACAATCCTGGCACGACTACTGCTTCCACTGCAAAAAATGCTCCGTGA

ATCTGGCCAACAAGCGCTTTGTTTTCCACCAGGAGCAAGTGTATTGTCCCGACTGTGCCAAAAAGCTGTA

AACTGACAGGGGCTCCTGTCCTGTAAAATGGCATTTGAATCTCGTTCTTTGTGTCCTTACTTTCTGCCCT

ATACCATCAATAGGGGAAGAGTGGTCCTTCCCTTCTTTAAAGTTCTCCTTCCGTCTTTTCTCCCATTTTA

CAGTATTACTCAAATAAGGGCACACAGTGATCATATTAGCATTTAGCAAAAGCAACCCTGCAGCAAAGT

GAATTTCTGTCCGGCTGCAATTTAAAAATGAAAACTTAGGTAGATTGACTCTTCTGCATGTTTCTCATAG

AGCAGAAAAGTGCTAATCATTTAGCCACTTAGTGATGTAAGCAAGAAGCATAGGAGATAAAACCCCCACT

GAGATGCCTCTCATGCCTCAGCTGGGACCCACCGTGTAGACACACGACATGCAAGAGTTGCAGCGGCTGC

TCCAACTCACTGCTCACCCTCTTCTGTGAGCAGGAAAAGAACCCTACTGACATGCATGGTTTAACTTCCT

CATCAGAACTCTGCCCTTCCTTCTGTTCTTTTGTGCTTTCAAATAACTAACACGAACTTCCAGAAAATTA

ACATTTGAACTTAGCTGTAATTCTAAACTGACCTTTCCCCGTACTAACGTTTGGTTTCCCCGTGTGGCAT

GTTTTCTGAGCGTTCCTACTTTAAAGCATGGAACATGCAGGTGATTTGGGAAGTGTAGAAAGACCTGAGA

AAACGAGCCTGTTTCAGAGGAACATCGTCACAACGAATACTTCTGGAAGCTTAACAAAACTAACCCTGCT

FIGURE 7 (continued)

GTCCTTTTTATTGTTTTAATTAATATTTTTGTTTTAATTGATAGCAAAATAGTTTATGGGTTTGGAAAC

TTGCATGAAAATATTTTAGCCCCCTCAGATGTTCCTGCAGTGCTGAAATTCATCCTACGGAAGTAACCGC

AAAACTCTAGAGGGGGAGTTGAGCAGGCGCCAGGGCTGTCATCAACATGGATATGACATTTCACAACAGT

GACTAGTTGAATCCCTTGTAACGTAGTAGTTGTCTGCTCTTTGTCCATGTGTTAATGAGGACTGCAAAGT

CCCTTCTGTTGTGATTCCTAGGACTTTTCCTCAAGAGGAAATCTGGATTTCCACCTACCGCTTACCTGAA

ATGCAGGATCACCTACTTACTGTATTCTACATTATTATATGACATAGTATAATGAGACAATATCAAAAGT

AAACATGTAATGACAATACATACTAACATTCTTGTAGGAGTGGTTAGAGAAGCTGATGCCTCATTTCTAC

ATTCTGTCATTAGCTATTATCATCTAACGTTTCAGTGTATCCTTACAGAAATAAAGCAGCATATGAAAAA

AAAAAAAAAAAAAAAAA

NP_001440 (LIM Domains highlighted in Red;

>gi|21361122|ref|NP_001440.2| four and a half LIM domains 1 [Homo sapiens]

MAEKFDCHYCRDPLQGKKYVQKDGHHCCLKCFDKFCANTCVECRKPIGADSKEVHYKNRFWHDTCFRCAK
CLHPLANETFVAKDNKILCNKCTTREDSPKCKGCFKAIVAGDQNVEYKGTVWHKDCFTCSNCKQVIGTGS
FFPKGEDFYCVTCHETKFAKHCVKCNKAITSGGITYQDQPWHADCFVCVTCSKKLAGQRFTAVEDQYYCV
DCYKNFVAKKCAGCKNPITGFGKGSSVVAYEGQSWHDYCFHCKKCSVNLANKRFVFHQEQVYCPDCAKKL

Human FHL1 isoform b
AF098518

>gi|3851649|gb|AF098518.1|AF098518 Homo sapiens four and a half LIM domains 1 protein isoform B (FHL1) mRNA, complete cds

TCCTATCTGCCACACATCCAGCGTGAGGTCCCTCCAGCTACAAGGTGGGCACCATGGCGGAGAAGTTTGA

CTGCCACTACTGCAGGGATCCCTTGCAGGGGAAGAAGTATGTGCAAAAGGATGGCCACCACTGCTGCCTG

AAATGCTTTGACAAGTTCTGTGCCAACACCTGTGTGGAATGCCGCAAGCCCATCGGTGCGGACTCCAAGG

AGGTGCACTATAAGAACCGCTTCTGGCATGACACCTGCTTCCGCTGTGCCAAGTGCCTTCACCCCTTGGC

CAATGAGACCTTTGTGGCCAAGGACAACAAGATCCTGTGCAACAAGTGCACCACTCGGGAGGACTCCCCC

AAGTGCAACGGGTGCTTCAAGGCCATTGTGGCAGGAGATCAAAACGTGGAGTACAAGGGGACCGTCTGGC

ACAAAGACTGCTTCACCTGTAGTAACTGCAAGCAAGTCATCGGGACTGGAAGCTTCTTCCCTAAAGGGGA

GGACTTCTACTGCGTGACTTGCCATGAGACCAAGTTTGCCAAGCATTGCGTGAAGTGCAACAAGGCCATC

ACATCTGGAGGAATCACTTACCAGGATCAGCCCTGGCATGCCGATTGCTTTGTGTGTGTTACCTGCTCTA

AGAAGCTGGCTGGGCAGCGTTTCACCGCTGTGGAGGACCAGTATTACTGCGTGGATTGCTACAAGAACTT

TGTGGCCAAGAAGTGTGCTGGATGCAAGAACCCCATCACTGGGAAAAGGACTGTGTCAAGAGTGAGCCGC

CCAGTCTCTAAAGCTAGGAAGCCCCCAGTGTGCCACGGGAAACGCTTGCCTCTCACCCTGTTTCCCAGCG

FIGURE 7 (continued)

CCAACCTCCGGGGCAGGCATCCGGGTGGAGAGAGGACTTGTCCCTCGTGGGTGGTGGTTCTTTATAGAAA
AAATCGAAGCTTAGCAGCTCCTCGTGGCCCGGGTTTGGTAAAGGCTCCAGTGTGGTGGCCTATGAAGGAC
AATCCTGGCACGACTACTGCTTCCACTGCAAAAAATGCTCCGTGAATCTGGCCAACAAGCGCTTTGTTTT
CCACCAGGAGCAAGTGTATTGTCCCGACTGTGCCAAAAAGCTGTAA

AAC72390

>gi|3851650|gb|AAC72390.1| four and a half LIM domains 1 protein
  isoform B [Homo sapiens]

MAEKFDCHYCRDPLQGKKYVQKDGHHCCLKCFDKFCANTCVECRKPIGADSKEVHYKNRFWHDTCFRCAK
CLHPLANETFVAKDNKILCNKCTTREDSPKCKGCFKAIVAGDQNVEYKGTVWHKDCFTCSNCKQVIGTGS
FFPKGEDFYCVTCHETKFAKHCVKCNKAITSGGITYQDQPWHADCFVCVTCSKKLAGQRFTAVEDQYYCV
DCYKNFVAKKCAGCKNPITGKRTVSRVSRPVSKARKPPVCHGKRLPLTLFPSANLRGRHPGGERTCPSWV
VVLYRKNRSLAAPRGPGLVKAPVWWPMKDNPGTTTASTAKNAP

Human FHL1 isoform c

AF220153

>gi|6942192|gb|AF220153.1|AF220153 Homo sapiens four and a half LIM
  domains 1 protein isoform C (FHL1) mRNA, complete cds, alternatively
  spliced ATGGCGGAGAAGTTTGACTGCCACTACTGCAGGGATCCCTTGCAGGGGAAGAAGTATGTGCAAAAGGATG
GCCACCACTGCTGCCTGAAATGCTTTGACAAGTTCTGTGCCAACACCTGTGTGGAATGCCGCAAGCCCAT
CGGTGCGGACTCCAAGGAGGTGCACTATAAGAACCGCTTCTGGCATGACACCTGCTTCCGCTGTGCCAAG
TGCCTTCACCCCTTGGCCAATGAGACCTTTGTGGCCAAGGACAACAAGATCCTGTGCAACAAGTGCACCA
CTCGGGAGGACTCCCCCAAGTGCAAGGGGTGCTTCAAGGCCATTGTGGCAGGAGATCAAAACGTGGAGTA
CAAGGGGACCGTCTGGCACAAAGACTGCTTCACCTGTAGTAACTGCAAGCAAGTCATCGGGACTGGAAGC
TTCTTCCCTAAGGGGAGGACTTCTACTGCGTGACTTGCCATGAGACCAAGTTTGCCAAGCATTGCGTGA
AGTGCAACAAGGGTTTGGTAAAGGCTCCAGTGTGGTGGCCTATGAAGGACAATCCTGGCACGACTACTGC
TTCCACTGCAAAAAATGCTCCGTGA

AAF32351

>gi|6942193|gb|AAF32351.1|AF220153_1 four and a half LIM domains 1
  protein isoform C [Homo sapiens]

MAEKFDCHYCRDPLQGKKYVQKDGHHCCLKCFDKFCANTCVECRKPIGADSKEVHYKNRFWHDTCFRCAK

FIGURE 7 (continued)
CLHPLANETFVAKDNKILCNKCTTREDSPKCKGCFKAIVAGDQNVEYKGTVWHKDCFTCSNCKQVIGTGS

FFPKGEDFYCVTCHETKFAKHCVKCNKGLVKAPVWWPMKDNPGTTTASTAKNAP

Other isoforms:

AK09170

>gi|21750135|dbj|AK091702.1| Homo sapiens cDNA FLJ34383 fis, clone
 HCHON1000015, highly similar to SKELETAL MUSCLE LIM-PROTEIN 1

AGTCCGCAGCCGCCGCCGCCACCGCCGCGCCTCGGCCTCGGTGCAGGCAGCGGCTGCCGCCGCCGAGACA

GCTGCGCGGGCGAGCATCCCCACGCAGCACCTTGGAAGTTGTTTTCAACCATATCCAGCCTTTGCCGAAT

ACATCCTATCTGCCACACATCCAGCGTGAGGTCCCTCCAGCTACAAGGTGGGCACCATGGCGGAGAAGTT

TGACTGCCACTACTGCAGGGATCCCTTGCAGGGGAAGAAGTATGTGCAAAAGGATGGCCACCACTGCTGC

CTGAAATGCTTTGACAAGTTTGCCAAGCATTGCGTGAAGTGCAACAAGGCCATCACATCTGGAGGAATCA

CTTACCAGGATCAGCCCTGGCATGCCGATTGCTTTGTGTGTTACCTGCTCTAAGAAGCTGGCTGGGCA

GCGTTTCACCGCTGTGGAGGACCAGTATTACTGCGTGGATTGCTACAAGAACTTTGTGGCCAAGAAGTGT

GCTGGATGCAAGAACCCCATCACTGGGTTTGGTAAAGGCTCCAGTGTGGTGGCCTATGAAGGACAATCCT

GGCACGACTACTGCTTCCACTGCAAAAAATGCTCCGTGAATCTGGCCAACAAGCGCTTTGTTTTCCACCA

GGAGCAAGTGTATTGTCCCGACTGTGCCAAAAAGCTGTAAACTGACAGGGGCTCCTGTCCTGTAAAATGG

CATTTGAATCTCGTTCTTTGTGTCCTTACTTTCTGCCCTATACCATCAATAGGGGAAGAGTGGTCCTTCC

CTTCTTTAAAGTTCTCCTTCCGTCTTTTCTCCCATTTTACAGTATTACTCAAATAAGGGCACACAGTGAT

CATATTAGCATTTAGCAAAAGCAACCCTGCAGCAAAGTGAATTTCTGTCCGGCTGCAATTTAAAAATGA

AAACTTAGGTAGATTGACTCTTCTGCATGTTTCTCATAGAGCAGAAAAGTGCTAATCATTTAGCCACTTA

GTGATGTAAGCAAGAAGCATAGGAGATAAAACCCCACTGAGATGCCTCTCATGCCTCAGCTGGGACCCA

CCGTGTAGACACACGACATGCAAGAGTTGCAGCGGCTGCTCCAACTCACTGCTCACCCTCTTCTGTGAGC

AGGAAAAGAACCCTACTGACATGCATGGTTTAACTTCCTCATCAGAACTCTGCCCTTCCTTCTGTTCTTT

TGTGCTTTCAAATAACTAACACGAACTTCCAGAAAATTAACATTTGAACTTAGCTGTAATTCTAAACTGA

CCTTTCCCCGTACTAACGTTTGGTTTCCCCGTGTGGCATGTTTCTGAGCGTTCCTACTTTAAAGCATGG

AACATGCAGGTGATTTGGGAAGTGTAGAAAGACCTGAGAAAACGAGCCTGTTTCAGAGGAACATCGTCAC

AACGAATACTTCTGGAAGCTTAACAAAACTAACCCTGCTGTCCTTTTTATTGTTTTAATTAATATTTTT

GTTTTAATTGATAGCAAAATAGTTTATGGGTTTGGAAACTTGCATGAAAATATTTTAGCCCCCTCAGATG

TTCCTGCAGTGCTGAAATTCATCCTACAGAAGTAACCGCAAAACTCTAGAGGGGGAGTTGAGCAGGCGCC

AGGGCTGTCATCAACATGGATATGACATTTCACAACAGTGACTAGTTGAATCCCTTGTAACGTAGTAGTT

FIGURE 7 (continued)

```
GTCTGCTCTTTGTCCATGTGTTAATGAGGACTGCAAAGTCCCTTCTGTTGTGATTCCTAGGACTTTTCCT
CAAGAGGAAATCTGGATTTCCACCTACCGCTTACCTGAAATGCAGGATCACCTACTTACTGTATTCTACA
TTATTATATGACATAGTATAATGAGACAATATCAAAAGTAAACATGTAATGACAATACATACTAACATTC
TTGTAGGAGTGGTTAGAGAAGCTGATGCCTCATTTCTACATTCTGTCATTAGCTATTATCATCTAACGTT
TCAGTGTATCCTTACAGAAATAAAGCAGCATATGAAT
>lcl|Sequence 1 ORF:197..670 Frame +2
MAEKFDCHYCRDPLQGKKYVQKDGHHCCLKCFDKFAKHCVKCNKAITSGGITYQDQPWHADCFVCVTCSK
KLAGQRFTAVEDQYYCVDCYKNFVAKKCAGCKNPITGFGKGSSVVAYEGQSWHDYCFHCKKCSVNLANKR
FVFHQEQVYCPDCAKKL
```

AX747139

```
>gi|32131527|emb|AX747139.1| Sequence 664 from Patent EP1308459
AGTCCGCAGCCGCCGCCGCCACCGCCGCGCCTCGGCCTCGGTGCAGGCAGCGGCTGCCGCCGCCGAGACA
GCTGCGCGGGCGAGCATCCCCACGCAGCACCTTGGAAGTTGTTTTCAACCATATCCAGCCTTTGCCGAAT
ACATCCTATCTGCCACACATCCAGCGTGAGGTCCCTCCAGCTACAAGGTGGGCACCATGGCGGAGAAGTT
TGACTGCCACTACTGCAGGGATCCCTTGCAGGGGAAGAAGTATGTGCAAAAGGATGGCCACCACTGCTGC
CTGAAATGCTTTGACAAGTTTGCCAAGCATTGCGTGAAGTGCAACAAGGCCATCACATCTGGAGGAATCA
CTTACCAGGATCAGCCCTGGCATGCCGATTGCTTTGTGTGTGTTACCTGCTCTAAGAAGCTGGCTGGGCA
GCGTTTCACCGCTGTGGAGGACCAGTATTACTGCGTGGATTGCTACAAGAACTTTGTGGCCAAGAAGTGT
GCTGGATGCAAGAACCCCATCACTGGGTTTGGTAAAGGCTCCAGTGTGGTGGCCTATGAAGGACAATCCT
GGCACGACTACTGCTTCCACTGCAAAAAATGCTCCGTGAATCTGGCCAACAAGCGCTTTGTTTTCCACCA
GGAGCAAGTGTATTGTCCCGACTGTGCCAAAAAGCTGTAAACTGACAGGGGCTCCTGTCCTGTAAAATGG
CATTTGAATCTCGTTCTTTGTGTCCTTACTTTCTGCCCTATACCATCAATAGGGGAAGAGTGGTCCTTCC
CTTCTTTAAAGTTCTCCTTCCGTCTTTTCTCCCATTTTACAGTATTACTCAAATAAGGGCACACAGTGAT
CATATTAGCATTTAGCAAAAAGCAACCCTGCAGCAAAGTGAATTTCTGTCCGGCTGCAATTTAAAAATGA
AAACTTAGGTAGATTGACTCTTCTGCATGTTTCTCATAGAGCAGAAAAGTGCTAATCATTTAGCCACTTA
GTGATGTAAGCAAGAAGCATAGGAGATAAAACCCCACTGAGATGCCTCTCATGCCTCAGCTGGGACCCA
CCGTGTAGACACACGACATGCAAGAGTTGCAGCGGCTGCTCCAACTCACTGCTCACCCTCTTCTGTGAGC
AGGAAAAGAACCCTACTGACATGCATGGTTTAACTTCCTCATCAGAACTCTGCCCTTCCTTCTGTTCTTT
TGTGCTTTCAAATAACTAACACGAACTTCCAGAAAATTAACATTTGAACTTAGCTGTAATTCTAAACTGA
CCTTTCCCCGTACTAACGTTTGGTTTCCCCGTGTGGCATGTTTTCTGAGCGTTCCTACTTTAAAGCATGG
AACATGCAGGTGATTTGGCAAGTGTAGAAAGACCTGAGAAAACGAGCCTGTTTCAGAGGAACATCGTCAC
AACGAATACTTCTGGAAGCTTAACAAAACTAACCCTGCTGTCCTTTTATTGTTTTAATTAATATTTTT
```

FIGURE 7 (continued)
GTTTTAATTGATAGCAAAATAGTTTATGGGTTTGGAAACTTGCATGAAAATATTTTAGCCCCCTCAGATG

TTCCTGCAGTGCTGAAATTCATCCTACAGAAGTAACCGCAAAACTCTAGAGGGGGAGTTGAGCAGGCGCC

AGGGCTGTCATCAACATGGATATGACATTTCACAACAGTGACTAGTTGAATCCCTTGTAACGTAGTAGTT

GTCTGCTCTTTGTCCATGTGTTAATGAGGACTGCAAAGTCCCTTCTGTTGTGATTCCTAGGACTTTTCCT

CAAGAGGAAATCTGGATTTCCACCTACCGCTTACCTGAAATGCAGGATCACCTACTTACTGTATTCTACA

TTATTATATGACATAGTATAATGAGACAATATCAAAAGTAAACATGTAATGACAATACATACTAACATTC

TTGTAGGAGTGGTTAGAGAAGCTGATGCCTCATTTCTACATTCTGTCATTAGCTATTATCATCTAACGTT

TCAGTGTATCCTTACAGAAATAAAGCAGCATATGAAT

>lcl|Sequence 1 ORF:197..670 Frame +2
MAEKFDCHYCRDPLQGKKYVQKDGHHCCLKCFDKFAKHCVKCNKAITSGGITYQDQPWHADCFVCVTCSK
KLAGQRFTAVEDQYYCVDCYKNFVAKKCAGCKNPITGFGKGSSVVAYEGQSWHDYCFHCKKCSVNLANKR
FVFHQEQVYCPDCAKKL*

FIGURE 7 (continued)

Mouse FHL1:

Related mRNA sequences from GenBank: Mouse: AK128904; U77039; AK158966; U41739; BC029024; BC031120; AF114380; BC059009; AF294825; BC055725

NM_010211

>gi|116517333|ref|NM_010211.2| Mus musculus four and a half LIM
  domains 1 (Fhl1), transcript variant 3, mRNA

AGTCCTGTGCTGCCGCTGTCGCCGCTGCGCTTTGGTCTCGGAGCTGGCAGCGGCCGCCGGTGCCGCCTAG

ACAGCTGCGCGGGCAACTGGTAGCTGTTCTTAGCTGTGCCCAGTCCTTCTGGAACACATCCTGTGTGAGG

TCCCTCCAGCTATAAGGTGGGCACCATGTCGGAGAAGTTCGACTGTCACTACTGCAGGGACCCCTTGCAG

GGGAAGAAGTACGTGCAGAAGGATGGCCGTCACTGCTGCCTGAAGTGCTTTGACAAGTTCTGCGCCAACA

CCTGCGTGGACTGCCGCAAGCCCATAAGCGCTGATGCCAAGGAGGTGCATTATAAGAATCGCTACTGGCA

CGACAACTGCTTCCGCTGTGCCAAGTGCCTTCACCCCTTGGCCAGTGAGACCTTTGTGTCCAAGGATGGC

AAGATCCTGTGCAACAAGTGCGCTACTCGGGAGGACTCCCCAGGTGCAAAGGGTGCTTCAAGGCCATTG

TGGCAGGAGACCAGAACGTGGAGTACAAGGGCACCGTCTGGCATAAAGACTGCTTCACCTGCAGCAACTG

CAAGCAAGTCATTGGGACCGGAAGCTTCTTCCCGAAAGGGGAGGACTTCTACTGTGTGACTTGCCATGAG

ACCAAGTTCGCCAAACATTGCGTGAAGTGCAACAAGGCCATCACATCTGGAGGAATCACTTACCAGGATC

AGCCCTGGCATGCCGAGTGCTTTGTGTGTGTTACCTGCTCTAAGAAGCTGGCTGGGCAGCGTTTCACCGC

TGTGGAGGACCAGTATTACTGCGTGGATTGCTACAAGAACTTTGTGGCCAAGAAGTGTGCTGGATGCAAG

AACCCCATCACTGGGTTTGGTAAAGGCTCCAGTGTGGTGGCCTATGAAGGACAATCCTGGCACGACTACT

GCTTCCACTGCAAAAAATGCTCCGTGAATCTGGCCAACAAGCGCTTTGTATTTCATAATGAGCAGGTGTA

TTGCCCTGACTGTGCCAAAAAGCTGTAACTTGACAGGGGCTCCTGTCCTGTAAAATGGCATTGGAACCAT

TCTTTGTGTCCTTTGCTCCCTCCCTCCCTCTGTACCATCCATAGGGCAAGAGTGGGCTTTCACCTCTTTA

AAGTTGCTCTTTCCGTCTTTTCTCCCATTTTACAGTATTAATCAACGAAGGACACACAGTGATCATATTA

AGATTTAGCAAAGAGCAACCTTGCAGCAAAAATAATTTCTCTGTTGCTGCACTGGAAAAACAAAACCTTA

GACTGACTCTTCTGCATGTTTCTCATAGAGCAGAAAAGTGCTAACCATGTAGCCACTTCACGATGTAAAC

GAGAAGCATAGGCGATAAAGCTCCCACTGAGACACCTTTGGGGCTCAGTCTGGATGCGCTGTGCGGTCAC

GTGACTGCGGTGTAAGAGTTGCAGCGGCTGCTCCAACTCCCTTCTCGCCTTCTCTGGGCAGTTAAGAACT

TGCCAGAATGCATGGTTTAACTTCCTTATCAAAACTCTGACCTTCCTTCTGTTCTTTTGTGCTTTCACAC

GACTAACACAGATTTCCAGAGAATTAACATTTTGAACTTTGTTGTAATTCTCAAGTGACTTTTCCCCCAT

ACTAACATTTGACTCCCTTACGTGGCGTGTTCTCTGAGCGTTCCTACTTTAAAGCATCGAACACACAGGT

GATTTGAAGCATCTAAGCAGATCTGAGAAAACGAGCCTGTTTCAGAACAAACTCACCACAGTGACTACTT

FIGURE 7 (continued)

CGGAAGCTTAACAAGACTAACTCTCCTGTCCTTTTTAATTTTTTTTTTAAATTTTGTTTTAATGAGTAG

TAAAATAGTTTATGGGTTTGGAAACTTGCATGACAATATTTGAGCCTCCTCAAACGTTCCTGCAGTTTTG

AGATTCATCCTGTAGACATGACAAAAACTCTAGAGCCGCAGCTGAGCAGGCACAGGCTGTCATCAAAGT

AGGGACAAGGTGAAGTCCTTGTAACATAACCGTTGTCTGCTCTTTGTCTGCATCCAGGAAGAGTGCAAAG

TCCCTTTGCTTGTGATTCTTAGAACTTTCCCTCCAGAATTGCAGTTAGACTCTGGGGCTGTCGGAGGTGG

TCGTCATCCTTCACAGGCAGGACTGGGTTTTCACCCCCTTCTCTGAAACGCAGGATTGCCTCCTTAACTG

TACTCTCCATTTTATTACATATATAACGAGCCAATATCAAAGTAAAGATGTAATGAAAACACACACTCAT

ATATTACTGTAGGAGTGGTTATAGATGCCAACACCTCATTTCCATATTTGTCATTAGCTGTTTCCATCTA

CTGTTTGATTGTATCCTTACAAAAATAAAGCAGCATAGAAAGAGCA

>CCDS30148.1_prot length=280
MSEKFDCHYCRDPLQGKKYVQKDGRHCCLKCFDKFCANTCVDCRKPISAD
AKEVHYKNRYWHDNCFRCAKCLHPLASETFVSKDGKILCNKCATREDSPR
CKGCFKAIVAGDQNVEYKGTVWHKDCFTCSNCKQVIGTGSFFPKGEDFYC
VTCHETKFAKHCVKCNKAITSGGITYQDQPWHAECFVCVTCSKKLAGQRF
TAVEDQYYCVDCYKNFVAKKCAGCKNPITGFGKGSSVVAYEGQSWHDYCF
HCKKCSVNLANKRFVFHNEQVYCPDCAKKL

AK158966

>gi|74186514|dbj|AK158966.1| Mus musculus visual cortex cDNA, RIKEN
  full-length enriched library, clone:K530020N06 product:four and a
  half LIM domains 1, full insert sequence

GGGGGAGCCGCAGCTCGTGCTCCGTGGCCGCTACTCCGGGGCTGCGCGGACCTGCTGGGCTTGGGTACCT

GCGGCCTCCGGCCTCCGCTGCCTCGCCCACGTTGGGGGCTGAGGAACCTGGGGCTCCAAGGTCCCTTAGG

GCAACTGGTAGCTGTTCTTAGCTGTGCCCAGTCCTTCTGGAACACATCCTGTGTGAGGTCCCTCCAGCTA

TAAGGTGGGCACCATGTCGGAGAAGTTCGACTGTCACTACTGCAGGGACCCCTTGCAGGGGAAGAAGTAC

GTGCAGAAGGATGGCCGTCACTGCTGCCTGAAGTGCTTTGACAAGTTCTGCGCCAACACCTGCGTGGACT

GCCGCAAGCCCATAAGCGCTGATGCCAAGGAGGTGCATTATAAGAATCGCTACTGGCACGACAACTGCTT

CCGCTGTGCCAAGTGCCTTCACCCCTTGGCCAGTGAGACCTTTGTGTCCAAGGATGGCAAGATCCTGTGC

AACAAGTGCGCTACTCGGGAGGACTCCCCCAGGTGCAAAGGGTGCTTCAAGGCCATTGTGGCAGGAGACC

AGAACGTGGAGTACAAGGGCACCGTCTGGCATAAAGACTGCTTCACCTGCAGCAACTGCAAGCAAGTCAT

TGGGACCGGAAGCTTCTTCCCGAAAGGGGAGGACTTCTACTGTGTGACTTGCCATGAGACCAAGTTCGCC

AAACATTGCGTGAAGTGCAACAAGGCCATCACATCTGGAGGAATCACTTACCAGGATCAGCCCTGGCATG

CCGACTGCTTTGTGTGTGTTACCTGCTCTAAGAAGCTGGCTGGGCAGCGTTTCACCGCTGTGGAGGACCA

GTATTACTGCGTGGATTGCTACAAGAACTTTGTGGCCAAGAAGTGTGCTGGATGCAAGAACCCCATCACT

GGGAAAAGGACTGTGTCAAGAGTGAGCCACCCAGTCTCTAAAGCTAGGAAGTCCCCAGTGTGCCACGGGA

FIGURE 7 (continued)

```
AACGCTTGCCTCTCACCCTGTTTCCCAGCGCCAACCTCCGGGGCAGGCATCCGGGTGGAGAGAGGACTTG
TCCCTCGTGGGTGGTGGTTCTTTATAGAAAAAATCGAAGCTTAGCAGCTCCTCGAGGCCCGGGTTTGGTA
AAGGCTCCAGTGTGGTGGCCTATGAAGGACAATCCTGGCACGACTACTGCTTCCACTGCAAAAAATGCTC
CGTGAATCTGGCCAACAAGCGCTTTGTATTTCATAATGAGCAGGTGTATTGCCCTGACTGTGCCAAAAAG
CTGTAACTTGACAGGGGCTCCTGTCCTGTAAAATGGCATTGGAACCATTCTTTGTGTCCTTTGCTCCCTC
CCTCCCTCTGTACCATCCATAGGGCAAGAGTGGGCTTTCACCTCTTTAAAGTTGCTCTTTCCGTCTTTTC
TCCCATTTTACAGTATTAATCAACGAAGGACACACAGTGATCATATTAAGATTTAGCAAAGAGCAACCTT
GCAGCAAAATAATTTCTCTGTTGCTGCACTGGAAAAACAAAACCTTAGACTGACTCTTCTGCATGTTTC
TCATAGAGCAGAAAAGTGCTAACCATGTAGCCACTTCACGATGTAAACGAGAAGCATAGGCGATAAAGCT
CCCACTGAGACACCTTTGGGGCTCAGTCTGGATGCGCTGTGCGGTCACGTGACTGCGGTGTAAGAGTTGC
AGCGGCTGCTCCAACTCCCTTCTCGCCTTCTCTGGGCAGTTAAGAACTTGCCAGAATGCATGGTTTAACT
TCCTTATCAAAACTCTGACCTTCCTTCTGTTCTTTTGTGCTTTCACACGACTAACACAGATTTCCAGAGA
ATTAACATTTTGAACTTTGTTGTAATTCTCAAGTGACTTTTCCCCCATACTAACATTTGACTCCCTTACG
TGGCGTGTTCTCTGAGCGTTCCTACTTTAAAGCATGGAACACACAGGTCATTTGAAGCATCTAAGCAGAT
CTGAGAAAACGAGCCTGTTTCAGAACAAACTCACCACAGTGACTACTTCGGAAGCTTAACAAGACTAACT
CTCCTGTCCTTTTAATTTTTTTTTAAATTTTGTTTTAATGAGTAGTAAAATAGTTTATGGGTTTGGAA
ACTTGCATGACAATATTTGAGCCTCCTCAAACGTTCCTGCAGTTTTGAGATTCATCCTGTAGACATGACA
AAAACTCTAGAGCCGCAGCTGAGCAGGCACAGGGCTGTCATCAAAGTAGGGACAAGGTGAAGTCCTTGTA
ACATAACCGTTGTCTGCTCTTTGTCTGCATCCAGGAAGAGTGCAAAGTCCCTTTGCTTGTGATTCTTAGA
ACTTTCCCTCCAGAATTGCAGTTAGACTCTGGGGCTGTCGGAGGTGGTCGTCATCCTTCACAGGCAGGAC
TGGGTTTTCACCCCCTTCTCTGAAACGCAGGATTGCCTCCTTAACTGTACTCTCCATTTTATTACATATA
TAACGAGCCAATATCAAAGTAAAGATGTAATGAAAACACACACTCATATATTACTGTAGGAGTGGTTATA
GATGCCAACACCTCATTTCCATATTTGTCATTAGCTGTTTCCATCTACTGTTTGATTGTATCCTTACAAA
AATAAAGCAGCATAG

>lcl|Sequence 1 ORF:224..1195 Frame +2
MSEKFDCHYCRDPLQGKKYVQKDGRHCCLKCFDKFCANTCVDCRKPISADAKEVHYKNRYWHDNCFRCAK
CLHPLASETFVSKDGKILCNKCATREDSPRCKGCFKAIVAGDQNVEYKGTVWHKDCFTCSNCKQVIGTGS
FFPKGEDFYCVTCHETKFAKHCVKCNKAITSGGITYQDQPWHAECFVCVTCSKKLAGQRFTAVEDQYYCV
DCYKNFVAKKCAGCKNPITGKRTVSRVSHPVSKARKSPVCHGKRLPLTLFPSANLRGRHPGGERTCPSWV
VVLYRKNRSLAAPRGPGLVKAPVWWPMKDNPGTTTASTAKNAP*
```

NUCLEIC ACIDS ENCODING FHL1 MUTATIONS ASSOCIATED WITH NOVEL X-LINKED MUSCULAR MYOPATHIES AND METHODS OF SCREENING A SUBJECT

This application is a continuation of U.S. application Ser. No. 14/077,877 filed on Nov. 12, 2013, now U.S. Pat. No. 9,150,923, which is a continuation of U.S. application Ser. No. 13/663,221 filed on Jun. 3, 2010, now U.S. Pat. No. 8,580,502, which is a 371 filing of International patent application no. PCT/CA2008/001062 filed on Jun. 4, 2008, which claims the benefit of U.S. provisional application No. 60/933,251 filed on Jun. 4, 2007, the entire content of each of which is incorporated herein by reference thereto.

FIELD OF THE INVENTION

The present invention relates to gene mutations. FHL1 mutations Associated With a Novel X-Linked Muscular Myopathies.

BACKGROUND OF THE INVENTION

Muscular dystrophies (MD) are defined as a group of inherited muscle disorders characterized by the progressive degeneration and weakness of voluntary skeletal muscle (Davies and Nowak, 2006). The various forms of MD vary widely with respect to age of onset, incidence, pattern of inheritance, rate of progression, and distribution and severity of muscle weakness. Certain muscular dystrophies can involve cardiac and smooth muscle tissue. MD most commonly exhibits an X-recessive mode of transmission, and is usually caused by mutations in the DMD gene on Xp21.2. Resulting in deficiencies in dystrophin protein, DMD mutations cause rapidly progressive weakness and wasting of the proximal muscles in the lower body. Duchenne MD (DMD), the most common neuromuscular disorder, is caused by frameshift mutations that result in the complete absence of functional dystrophin, whereas the phenotypically less severe Becker's MD is associated with missense and inframe deletions that result in reduced levels of functional dystrophin or expression of partially functional protein (Davies and Nowak, 2006). This structural protein functions to link the actin cytoskeleton with muscle fibre membranes across the sarcolemma, providing structural support to the muscle cell (Ervasti, 2007). The absence of dystrophin compromises the complex across the muscle, leading to degeneration of muscle tissue. Affecting 1 in 4,000 live male births, DMD is correlated with onset before age 6 and a typical life span of 20-25 years; in contrast, Becker's MD has onset in adolescence or adulthood with symptoms similar to but generally less severe than DMD. These include muscle pseudohypertrophy, proximal muscle atrophy, and rarely, cardiomyopathy and/or mental deficits.

Emery-Dreifuss MD (EDMD) is another form of late onset X-recessive MD caused by deficiencies in the emerin protein, encoded by the EMD gene on Xq28 (Ellis, 2006). EDMD is phenotypically distinct from other X-linked MDs in that there is humeroperoneal distribution of muscle wasting, absence of muscle pseudohypertrophy, and at very high frequency, cardiomyopathy.

There is a need in the art to identify Four and a Half LIM domains protein 1 (FHL-1) mutations, and the proteins encoded therefrom that are associated with muscular myopathies including muscular dystrophy and cardiomyopathy. LIM domains, named after their initial discovery in the proteins Lin11, Is1-1 & Mec-3, are protein structural domains, composed of two contiguous zinc finger domains, separated by a two-amino acid residue hydrophobic linker. Further there is a need in the art to be able to screen for such mutations to identify individuals that have or are at risk for developing muscular myopathies, including muscular dystrophy and cardiomyopathy.

SUMMARY OF THE INVENTION

The present invention relates to gene mutations. More specifically, the present invention relates to gene mutations associated with muscular myopathies.

According to the present invention there is provided a protein comprising amino acids 1-230 of SEQ ID NO:1, a fragment thereof or a sequence exhibiting at least 70% identity thereto and comprising the amino acid sequence VAKKCX$_1$GX$_2$X$_3$NPIT (SEQ ID NO:4) wherein X$_2$ is any amino acid except C; and X$_1$ and X$_3$ are independently any amino acid.

Preferably X$_1$ is A or S and X$_3$ is K, N or Q.

Also provided is the protein as defined above, wherein X$_2$ is tryptophan.

The present invention also provides a protein as defined above, wherein the protein is defined by SEQ ID NO:2 or SEQ ID NO:3.

Also provided by the present invention is a nucleic acid comprising a sequence
  a) encoding the protein as defined above or a fragment thereof;
  b) that is the complement of a sequence encoding the protein as defined above, or a fragment thereof;
  c) that is capable of hybridizing to a nucleic acid encoding the protein as defined above or fragment thereof under stringent hybridization conditions; or
  d) that exhibits greater than about 70% sequence identity with the nucleic acid defined in a) or b).

Also provided by the present invention is a nucleic acid as defined above wherein the fragment comprises the amino acid sequence GWK.

Also provided is a nucleic acid as defined above wherein X$_2$ is tryptophan.

Also contemplated is the nucleic acid as defined above wherein the protein is defined by SEQ ID NO:2 or SEQ ID NO:3.

The present invention also provides a method of screening a subject for an X-linked muscular myopathy comprising,
  a) obtaining a biological sample from the subject, and;
  b) assaying the sample for a nucleic acid encoding the protein as defined above or a fragment thereof comprising the amino acid sequence VAKKCX$_1$GX$_2$X$_3$NPIT (SEQ ID NO:4) wherein X$_2$ is any amino acid except C; and X$_1$ and X$_3$ are independently any amino acid, or
  c) assaying the sample for the protein as defined above or a fragment thereof comprising the amino acid sequence VAKKCX$_1$GX$_2$X$_3$NPIT (SEQ ID NO:4) wherein X$_2$ is any amino acid except C; and X$_1$ and X$_3$ are independently any amino acid.

Also provided is a method as defined above, wherein the muscular myopathy is a skeletal muscle myopathy, or a cardiomyopathy, for example, but not limited to muscular dystrophy.

Also provided is a method as defined above, wherein X$_2$ is tryptophan.

The invention also provides a method as defined above wherein the protein is defined by SEQ ID NO:2 or SEQ ID NO:3.

Further provided is the method as defined above, wherein the subject is a human subject.

Also provided is a method as defined above, wherein the biological sample is a blood sample.

Also provided is a method as defined above wherein assaying comprises PCR, probe hybridization or sequencing.

The present invention also provides a kit comprising
i) a protein or fragment thereof that is associated with muscular myopathy as described herein,
ii) an antibody that selectively binds to a protein or fragment thereof associated with muscular myopathy as described herein, rather than a wild-type protein not associated with the muscular myopathy,
iii) one or more nucleic acid primers to amplify a nucleotide sequence encoding a protein or fragment thereof which comprises a mutation associated with an X-linked muscular myopathy as provided herein,
iv) one or more nucleic acid probes of between about 9 and 100 nucleotides that hybridizes to the nucleotide sequence encoding a protein or fragment thereof which comprises a mutation associated with an X-linked muscular myopathy as provided herein,
v) one or more reagents including, but not limited to buffer(s), dATP, dTTP, dCTP, dGTP, or DNA polymerase(s),
vi) instructions for assaying, diagnosing or determining the risk of a subject to muscular myopathy,
vii) instructions for using any component or practicing any method as described herein,
or any combination thereof.

The present invention also provides a FHL-1 protein comprising an isoleucine insertion at position 128. In a preferred embodiment protein comprises the human isoform a, b or c amino acid sequence or an amino acid sequence which is at least 70% identical thereto.

The present invention also provides a nucleotide sequence encoding the FHL-1 protein as defined above.

Also provided by the present invention is an antibody that selectively binds the FHL-1 protein as described above but preferably not a wild type FHL-1 protein.

The present invention also provides a method of screening a subject for an X-linked muscular myopathy comprising
a) obtaining a biological sample from the subject;
b) assaying the sample for a nucleic acid encoding a FHL-1 protein comprising an isoleucine insertion at position 128, or
c) assaying the sample for the FHL-1 protein comprising an isoleucine insertion at position 128,
wherein the presence of the nucleic acid or protein indicates that the subject has or is at risk of developing a muscular myopathy.

Also provided by the present invention are kits comprising FHL-1 protein having an isoleucine insertion at position 128, a nucleotide sequence encoding a FHL-1 protein comprising an isoleucine insertion at position 128, a probe that may be employed to identify nucleotide sequences encoding an isoleucine at position 128, primers that can amplify such sequences, antibodies that recognize the proteins as defined above but preferably not wild-type FHL-1 proteins, instructions for screening subjects, one or more reagents that can be used to use one or components of the kit or any combination thereof. Other components as described herein or as would be known in the art can also be included and this list is not meant to be limiting in any manner.

This summary of the invention does not necessarily describe all features of the invention.

BRIEF DESCRIPTION OF THE DRAWINGS

These and other features of the invention will become more apparent from the following description in which reference is made to the appended drawings wherein:

FIGS. 1A-C show pedigrees of three families. FIG. 1A shows the pedigree of the X-linked postural muscular myopathy family. Family members from whom DNA samples were obtained are indicated by arrows (↙). FIG. 1B shows UK family 2 pedigree members exhibiting muscular myopathies. FIG. 1C shows UK family 3 pedigree members exhibiting muscular myopathies.

FIG. 3 shows muscle biopsy of the vastus lateralis muscle (A.) and anterior tibial muscle (B). Muscle histology revealed a moderate myopathy with a moderate perimysial and limited endomysial fibrosis. In all biopsies, some round, autophagic vacuoles predominant in type 2 fibers were detectable. These vacuolar changes were most prominent in patient B. Additionally, centrally placed myonuclei were increased and rarely single fiber necrosis and granular myofiber degeneration were seen.

FIG. 4 shows muscle biopsy of the vastus lateralis muscle (A.) and anterior tibial muscle (B). Myosin ATPase staining at acidic pH 4.3/4.6 reveals type I (dark) and type II (light) muscle fibre distribution in patients in the early stages of disease. Variability of fiber size was increased in all specimens, with diameters ranging between 20 to 100. mu·m, and most prominent in type 2 fibers. In NADH and COX histochemistry centrally negative core-like lesions were detected in both patients, without any further mitochondrial alterations.

FIG. 5 shows linkage analysis to the DMD locus using polymorphic STR intragenic markers STR-44, STR-45, STR-48, STR-49, and STR-50 revealed different haplotypes in the affecteds, conclusively excluding the DMD locus. Recombination of markers STR-44, STR-48, STR-49, and STR-50 is evident, as illustrated by haplotypes.

FIG. 6 shows an ideogrammatic representation of the X-linked myopathy with postural muscle atrophy (XMPMA) locus on the distal arm of chromosome X, the electropherograms indicating the wild-type (SEQ ID NO: 40) and mutation sequence (SEQ ID NO: 41) for the Austrian XMPMA family, and the secondary structure of FHL1, indicating the position of the resulting amino acid substitution, C224W, relative to structural features in the protein (SEQ ID NO: 39).

FIG. 7 shows amino acid and nucleotide sequences as described herein and throughout as well as several wild-type protein sequences known in the art, e.g., mRNA sequence NM_001449 (SEQ ID NO:7) and amino acid sequence NP_001440 (SEQ ID NO:8) of Human FHL1 isoform a; mRNA sequence AF098518 (SEQ ID NO:9) and amino acid sequence AAC72390 (SEQ ID NO:10) of Human FHL1 isoform b; mRNA sequence AF220153 (SEQ ID NO:11) and amino acid sequence AAF32351 (SEQ ID NO:12) of Human FHL1 isoform c; mRNA sequence (SEQ ID NO:13) and amino acid sequence (SEQ ID NO:14) of Human FHL1 isoform AK09170; mRNA sequence (SEQ ID NO:15) and amino acid sequence (SEQ ID NO:16) of Human FHL1 isoform AX747139; mRNA sequence (SEQ ID NO:17) and amino acid sequence (SEQ ID NO:18) of Mouse FHL1 isoform NM_010211; mRNA sequence (SEQ ID NO:19) and amino acid sequence (SEQ ID NO:20) of Mouse FHL1 isoform AK158966.

Figure 8:
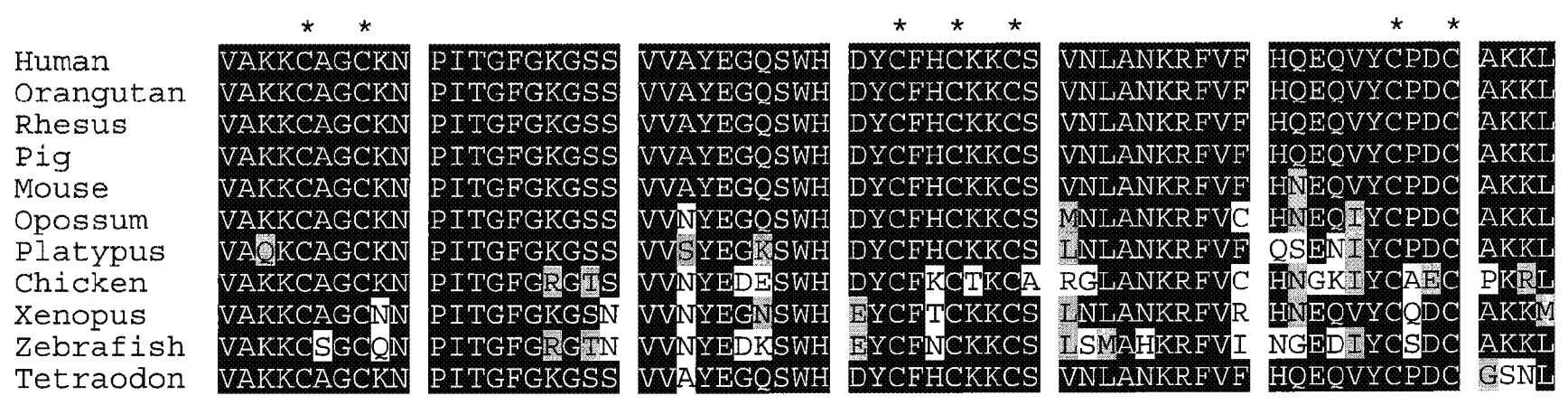

FIG. 8 shows a comparative analysis of the 4$^{th}$ LIM binding domain of FHL1 across several species, i.e., Human (SEQ ID NO:21), Rhesus (SEQ ID NO:22), Mouse (SEQ ID NO:23), Opossum (SEQ ID NO:24), Chicken (SEQ ID NO:25), *Xenopus* (SEQ ID NO:26), Zebrafish (SEQ ID NO:27) and Tetraodon (SEQ ID NO:28).

DETAILED DESCRIPTION

Figure 2:
FIG. 2 shows atrophy of the postural back muscles as clinically assessed in a patient in the early stages of disease. Atrophy of the deltoideus muscle. Gluteus maximus, biceps brachii, triceps brachii, and lower arms appear normal. Biceps femoris (hamstring muscles), adductor magnus (thighs), abductor pollicis brevis and adductor pollicis longus (hand) show signs of atrophy.

The following description is of a preferred embodiment.

We have identified a large multigenerational Austrian family displaying a novel form of muscular myopathy with an X-recessive mode of inheritance. Affected individuals develop specific atrophy of postural muscles, with histology showing gradual atrophy of type I muscle fibers. Known X-recessive MDs were excluded by immunocytochemical staining, marker analysis and gene sequencing. Marker analysis revealed significant linkage at Xq26-q27. Haplotype analysis based on 250K array SNP chip data of five affected individuals along with three unaffected family members confirmed this linkage region on the distal arm of the X-chromosome (Xq26-q27) and enabled us to narrow down the candidate interval to 26 Mb encompassing approximately 850 consecutive SNPs. Sequencing of functional candidate genes led to the identification of a mutation within the four-and-a-half LIM domain 1 gene (FHL1), which putatively disrupts the 4th LIM domain. FHL1 on Xq27.2, is highly expressed specifically in type I muscle fibers. Thus, we have characterized a new form of myopathy, X-linked myopathy with postural muscle atrophy (XMPMA), and identified FHL1 as the causative gene. Other family studies also confirm FHL1 as the causative gene in X-linked myopathies and cardiomyopathies, as described herein.

Proteins and Amino Acids

According to an embodiment of the present invention there is provided a protein comprising amino acids 1-230 of SEQ ID NO:1, a fragment thereof or an amino acid sequence exhibiting at least 70% identity thereto and comprising the amino acid sequence VAKKCX$_1$GX$_2$X$_3$NPIT (SEQ ID NO:4) wherein X$_2$ is any amino acid except C; and X$_1$ and X$_3$ are independently any amino acid. Preferably X$_1$ is A or S and X$_3$ is K, N or Q. In a preferred embodiment X$_2$ is tryptophan, for example, but not limited to as defined by SEQ ID NO:2 or SEQ ID NO:3.

An amino acid sequence exhibiting at least 70% identity thereto is understood to include sequences that exhibit 70%, 75%, 80%, 85%, 90%, 91%, 92%, 93%, 94%, 95%, 96%, 97%, 98%, 99%, 99.9% or 100% identity, or any value therein between to SEQ ID NO:1 or a fragment thereof. Further, the protein may be defined as comprising a range of sequence identity as defined by any two of the values listed or any values therein between.

Any method known in the art may be used for determining the degree of identity between polypeptide sequences. For example, but without wishing to be limiting, a sequence search method such as BLAST (Basic Local Alignment Search Tool; (Altschul S F, Gish W, Miller W, Myers E W, Lipman D J (1990) J Mol Biol 215, 403 410) can be used according to default parameters as described by Tatiana et al., FEMS Microbial Lett. 174:247 250 (1999), or on the National Center for Biotechnology Information web page at ncbi.nlm.gov/BLAST/, for searching closely related sequences. BLAST is widely used in routine sequence alignment; modified BLAST algorithms such as Gapped BLAST, which allows gaps (either insertions or deletions) to be introduced into alignments, or PSI-BLAST, a sensitive search for sequence homologs (Altschul et al., Nucleic Acids Res. 25:3389 3402 (1997); or FASTA, which is available on the world wide web at ExPASy (EMBL—European Bioinformatics Institute). Similar methods known in the art may be employed to compare DNA or RNA sequences to determine the degree of sequence identity.

In an embodiment of the present invention, which is not meant to be considered limiting there is provided a FHL1 protein comprising an amino acid insertion. In a further embodiment, there is provided a FHL1 protein comprising an isoleucine amino acid insertion. In still a further embodiment, there is provided an a FHL1 protein comprising 128InsI. Any isoform, for example, but not meant to be limiting to isoforms a, b or c may comprise this amino acid insertion. Nucleotide sequences encoding such proteins are also encompassed by the invention as described below.

Nucleic Acids

Also contemplated by the present invention is a nucleic acid comprising a sequence
 a) encoding the protein as described above, or a fragment thereof;
 b) that is the complement of a sequence encoding the protein as described above, or a fragment thereof;
 c) that is capable of hybridizing to a nucleic acid encoding the protein as described above or fragment thereof under stringent hybridization conditions; or
 d) that exhibits greater than about 70% sequence identity with the nucleic acid described in a) or b).

Without wishing to be limiting, representative examples of nucleic acids encoding the proteins as defined above are provided by SEQ ID NOs:5 and 6 wherein X is not cytosine (c) or any other nucleotide that produces cysteine when translated.

The nucleic acids described above include nucleic acids that may be employed to produce proteins which are associated with X-linked muscular myopathy, probes which may be used to identify or diagnose subjects carrying a mutation which causes or predisposes the subject to muscular myopathy, antisense or short inhibitory RNA that may be used to modulate production of protein from genes associated with muscular myopathy or a combination thereof. The proteins, fragments thereof or nucleic acids as described above also may be used to produce antibodies that selectively recognize the proteins as described above preferably over wild-type proteins known in the art.

In a preferred embodiment of the nucleic acids as described above, X$_2$ is tryptophan. In a further embodiment of the method, the protein is defined by SEQ ID NO:2 or SEQ ID NO:3. In still a further embodiment, the protein is a human FHL1 protein comprising an isoleucine amino acid insertion at position 128 (128InsI).

Stringent hybridization conditions may be, for example but not limited to hybridization overnight (from about 16-20 hours) hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours); or hybridization in Church aqueous phosphate buffer (7% SDS; 0.5M NaPO$_4$ buffer pH 7.2; 10 mM EDTA) at 65° C., with 2 washes either at 50° C.

in 0.1×SSC, 0.1% SDS for 20 or 30 minutes each, or 2 washes at 65° C. in 2×SSC, 0.1% SDS for 20 or 30 minutes each for unique sequence regions.

The present invention is further directed to a nucleotide construct comprising the nucleic acid as described above operatively linked to one or more regulatory elements or regulatory regions. By "regulatory element" or "regulatory region", it is meant a portion of nucleic acid typically, but not always, upstream of a gene, and may be comprised of either DNA or RNA, or both DNA and RNA. Regulatory elements may include those which are capable of mediating organ specificity, or controlling developmental or temporal gene activation. Furthermore, "regulatory element" includes promoter elements, core promoter elements, elements that are inducible in response to an external stimulus, elements that are activated constitutively, or elements that decrease or increase promoter activity such as negative regulatory elements or transcriptional enhancers, respectively. By a nucleotide sequence exhibiting regulatory element activity it is meant that the nucleotide sequence when operatively linked with a coding sequence of interest functions as a promoter, a core promoter, a constitutive regulatory element, a negative element or silencer (i.e. elements that decrease promoter activity), or a transcriptional or translational enhancer.

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

Regulatory elements as used herein, also includes elements that are active following transcription initiation or transcription, for example, regulatory elements that modulate gene expression such as translational and transcriptional enhancers, translational and transcriptional repressors, and mRNA stability or instability determinants. In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements that modify gene expression. It is to be understood that nucleotide sequences, located within introns, or 3' of the coding region sequence may also contribute to the regulation of expression of a coding region of interest. A regulatory element may also include those elements located downstream (3') to the site of transcription initiation, or within transcribed regions, or both. In the context of the present invention a post-transcriptional regulatory element may include elements that are active following transcription initiation, for example translational and transcriptional enhancers, translational and transcriptional repressors, and mRNA stability determinants.

The regulatory elements, or fragments thereof, may be operatively associated (operatively linked) with heterologous regulatory elements or promoters in order to modulate the activity of the heterologous regulatory element. Such modulation includes enhancing or repressing transcriptional activity of the heterologous regulatory element, modulating post-transcriptional events, or both enhancing/repressing transcriptional activity of the heterologous regulatory element and modulating post-transcriptional events. For example, one or more regulatory elements, or fragments thereof, may be operatively associated with constitutive, inducible, tissue specific promoters or fragment thereof, or fragments of regulatory elements, for example, but not limited to TATA or GC sequences may be operatively associated with the regulatory elements of the present invention, to modulate the activity of such promoters within plant, insect, fungi, bacterial, yeast, or animal cells.

There are several types of regulatory elements, including those that are developmentally regulated, inducible and constitutive. A regulatory element that is developmentally regulated, or controls the differential expression of a gene under its control, is activated within certain organs or tissues of an organ at specific times during the development of that organ or tissue. However, some regulatory elements that are developmentally regulated may preferentially be active within certain organs or tissues at specific developmental stages, they may also be active in a developmentally regulated manner, or at a basal level in other organs or tissues within a plant as well.

By "promoter" it is meant the nucleotide sequences at the 5' end of a coding region, or fragment thereof that contain all the signals essential for the initiation of transcription and for the regulation of the rate of transcription. There are generally two types of promoters, inducible and constitutive promoters.

An inducible promoter is a promoter that is capable of directly or indirectly activating transcription of one or more DNA sequences or genes in response to an inducer. In the absence of an inducer the DNA sequences or genes will not be transcribed. Typically the protein factor that binds specifically to an inducible promoter to activate transcription is present in an inactive form which is then directly or indirectly converted to the active form by the inducer. The inducer can be a chemical agent such as a protein, metabolite, growth regulator, or a physiological stress imposed directly by heat, cold, or toxic elements or indirectly through the action of a pathogen or disease agent such as a virus.

A constitutive promoter directs the expression of a gene throughout the various parts of an organism and/or continuously throughout development of an organism. Any suitable constitutive promoter may be used to drive the expression of the proteins or fragments thereof as described herein. Examples of known constitutive promoters include but are not limited to those associated with the CaMV 35S transcript. (Odell et al., 1985, *Nature*, 313: 810-812).

The term "constitutive" as used herein does not necessarily indicate that a gene is expressed at the same level in all cell types, but that the gene is expressed in a wide range of cell types, although some variation in abundance is often observed.

The gene construct of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3 prime end of the mRNA precursor.

The gene construct of the present invention can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA.

The present invention further includes vectors comprising the nucleic acids as described above. Suitable expression vectors for use with the nucleic acid sequences of the present invention include, but are not limited to, plasmids, phagemids, viral particles and vectors, phage and the like. For insect cells, baculovirus expression vectors are suitable. For plant cells, viral expression vectors (such as cauliflower mosaic virus and tobacco mosaic virus) and plasmid expression vectors (such as the Ti plasmid) are suitable. The entire expression vector, or a part thereof, can be integrated into the host cell genome.

Those skilled in the art will understand that a wide variety of expression systems can be used to produce the proteins or fragments thereof as defined herein. With respect to the in vitro production, the precise host cell used is not critical to the invention. The proteins or fragments thereof can be produced in a prokaryotic host (e.g., *E. coli* or *B. subtilis*) or in a eukaryotic host (e.g., *Saccharomyces* or *Pichia*; mammalian cells, such as COS, NIH 3T3, CHO, BHK, 293, or HeLa cells; insect cells; or plant cells). The methods of transformation or transfection and the choice of expression vector will depend on the host system selected and can be readily determined by one skilled in the art. Transformation and transfection methods are described, for example, in Ausubel et al. (1994) Current Protocols in Molecular Biology, John Wiley & Sons, New York; and various expression vectors may be chosen from those provided, e.g., in Cloning Vectors: A Laboratory Manual (Pouwels et al., 1985, Supp. 1987) and by various commercial suppliers.

In addition, a host cell may be chosen which modulates the expression of the inserted sequences, or modifies/processes the gene product in a specific, desired fashion. Such modifications (e.g., glycosylation) and processing (e.g., cleavage) of protein products may be important for the activity of the protein. Different host cells have characteristic and specific mechanisms for the post-translational processing and modification of proteins and gene products. Appropriate cell lines or host systems can be chosen by one skilled in the art to ensure the correct modification and processing of the expressed cardiac stem cell proliferation protein.

Methods of Screening

The present invention also provides a method of screening a subject for an X-linked muscular myopathy comprising,
  a) obtaining a biological sample from the subject, the biological sample comprising DNA or RNA if the sample is assayed for nucleic acid, or FHL-1 protein if the sample is assayed for protein, and;
  b) assaying the sample for a nucleic acid encoding the protein as defined above or a fragment thereof comprising the amino acid sequence VAKKCX$_1$GX$_2$X$_3$NPIT (SEQ ID NO:4) wherein X$_2$ is any amino acid except C; and X$_1$ and X$_3$ are independently any amino acid, or
  c) assaying the sample for the protein as defined above or a fragment thereof comprising the amino acid sequence VAKKCX$_1$GX$_2$X$_3$NPIT (SEQ ID NO:4) wherein X$_2$ is any amino acid except C; and X$_1$ and X$_3$ are independently any amino acid.

The present invention also provides a method of screening a subject for an X-linked muscular myopathy comprising,
  a) obtaining a biological sample from the subject, the biological sample comprising DNA or RNA if the sample is assayed for nucleic acid, or FHL-1 protein if the sample is assayed for protein, and;
  b) assaying the sample for a nucleic acid encoding a FHL-1 protein comprising an isoleucine insertion at position 128 (128InsI), or
  c) assaying the sample for the FHL-1 protein comprising an isoleucine insertion at position 128 (128InsI).

The FHL protein may be identical or substantially identical to human FHL-1 protein isoform a, b or c, as described herein or it may be substantially identical meaning comprising at least 70% identity, more preferably at least 75%, 80%, 85%, 90%, 91%, 92%, 93%, 94%, 95%, 96%, 97%, 98%, 99%, 99.5% or 99.9% identity thereto.

Also provided is a method as defined above, wherein the muscular myopathy is a skeletal muscle myopathy, for example, but not limited to muscular dystrophy. Alternatively, but not wishing to be limiting, the muscular myopathy may be a cardiomyopathy. Cardiomyopathies are specifically contemplated as the affected individuals studied herein appear to exhibit symptoms of such and/or die of heart related disease.

In the embodiment described above, it is to be understood that identifying the target nucleic acid, protein or both in the biological sample obtained from the subject, may be employed to identify a subject having or being at risk for developing a muscular myopathy, for example, but not limited to an X-linked muscular dystrophy or cardiomyopathy By the terms "assaying the sample for a nucleic acid" it is meant testing and/or characterizing the sample provided by the subject for a nucleic acid that encodes a protein as defined above and is meant to include without limitation hybridization assays, nucleotide sequencing, nucleotide PCR including, but not limited to RT-PCR, etc or any combination thereof.

In a preferred embodiment of the method of screening as defined above, X$_2$ is tryptophan. In a further embodiment, which is not meant to be limiting, the protein is defined by SEQ ID NO:2 or SEQ ID NO:3. Also, while the method of screening may be practiced on a variety of subjects, preferably, the subject is a human subject.

The sample obtained from the subject may comprise any tissue or biological fluid sample from which DNA or RNA may be obtained. For example, but not wishing to be limiting, DNA may be obtained from blood, hair follicle cells, skin cells, cheek cells, tissue biopsy, or the like. In a preferred embodiment, the sample is blood.

The present invention also contemplates screening methods which identify and/or characterize the proteins as defined above within biological samples from subjects. Such samples may or may not comprise DNA or RNA. For example, such screening methods may employ immunological methods, for example, but not limited to antibody binding assays such as ELISAs or the like, protein sequencing, electrophoretic separations to identify the proteins as described above in a sample. As will be evident to a person of skill in the art, the screening methods allow for the differentiation of the proteins as defined herein from wild type proteins known in the art.

Kits

Also provided by the present invention is a kit comprising one or more proteins or fragments thereof that is associated with muscular myopathy, for example, but not limited to, a muscular dystrophy or cardiomyopathy as described herein, an antibody that selectively binds to a protein or fragment thereof associated with muscular myopathy, dystrophy, or cardiomyopathy as described herein, rather than a wild-type protein not associated with muscular myopathy, dystrophy, or cardiomyopathy, one or more nucleic acid primers to amplify a nucleotide sequence encoding a protein or fragment thereof which comprises a mutation associated with an X-linked muscular myopathy, dystrophy or cardiomyopathy as described herein, one or more nucleic acid probes of between about 9 and 100 nucleotides that hybridizes to the nucleotide sequence encoding a protein or fragment thereof which comprises a mutation or insertion associated with an X-linked muscular myopathy, dystrophy or cardiomyopathy as described herein, one or more reagents including, but not limited to buffer(s), dATP, dTTP, dCTP, dGTP, DNA polymerase(s), instructions for assaying, diagnosing or determining the risk of a subject to a muscular myopathy, dystrophy, or cardiomyopathy, instructions for using any component or practicing any method as described herein, or any combination thereof.

In a further embodiment, which is not meant to be considered limiting in any manner, there is provided a method of producing a non-human animal that comprises the protein as defined herein and throughout, the method comprising, transforming the non-human animal with a nucleotide construct that encodes the protein as defined above, preferably in the absence of the wild type FHL-1 protein, more preferably in the absence of all isoforms of the FHL-1 protein. As human subjects exhibit hypertrophy of specific muscles, the method as defined above may be employed in animals, for example, in beef, horses, poultry, swine or any other non-human animal to produce animals that may exhibit increased muscle mass in various body areas.

The present invention will be further illustrated in the following examples.

EXAMPLES

Example 1: Materials and Methods

Clinical Assessment

Probands are from a multigenerational Austrian family displaying clinical features suggesting MD, but with clinical differences from previously described muscular dystrophies (FIG. 1). We identified living 6 patients (all males). Neurological examination was performed by a neurologist trained in neuromuscular disorders (S.Q.). First-degree relatives were examined when possible. Serum creatine kinase (CK) levels were measured in all affected individuals and their family members.

Myosin ATPase Staining

Standard histological protocols were employed to stain for myosin ATPase at acidic pH 4.3/4.6 and assess the distribution of type I (slow twitch) and type II (fast twitch) muscle fibre types. Procedures were performed on adductor, biceps, deltoideus, erector, extensor, flexor, frontalis, gastrocnemius, gluteus, latissimus, pectoralis, peronaeus, rectus, sartorius, soleus, tibialis, triceps, vastus muscles, etc.

Muscle Immunocytochemistry

Standard immunocytochemistry protocols were utilized to perform staining for dystrophin, adhalin, merosin, dysferlin, caveolin, α-dystroglycan, emerin, lamin A/C, desmin, β-slow myosin heavy chain, spectrin, and α-sarcoglycan following muscle biopsies of patient 50. Monoclonal antibodies were obtained from Novocastra Laboratories Ltd. (Vision BioSystems, U.K.) for spectrin (NCL-SPECT), dysferlin (NCL-Hamlet), emerin (NCL-Emerin), and α-sarcoglycan (NCL-α-SARC). Additional Novocastra antibodies were used for dystrophin staining, specific to the dystrophin rod-like domain (NCL-DYS1), C-terminus (NCL-DYS2), and N-terminus (NCL-DYS3). Monoclonal antibodies were employed for merosin (MAB 1922; Chemicon, Germany), caveolin (Caveolin3; Transduction Laboratories, BD Biosciences, Europe), α-dystroglycan (KlonVIA4-1; Upstate Biotechnology, Europe), lamin A/C (Mouse Hybridoma Supernatant), desmin (M0760, Klon D33; Dako, Europe), and myosin (805-502-L001, Lot L02279, Klon A4.951; Alexis Biochemicals, Europe) staining procedures.

Exclusion of the DMD Locus

Genomic DNA was extracted from blood samples using standard procedures. DNA was amplified by PCR with conditions for thermal cycling adapted from the protocol set out by ABI Prism® Linkage Mapping Set v2.5. Denaturation was performed at 95° C. for 15 min, followed by 10 cycles of 94° C. for 15 min, 55° C. for 15 sec, 72° C. for 30 sec. This was followed by 20 cycles of 89° C. for 15 sec, 55° C. for 15 sec, and 72° C. for 30 sec, with a final extension step of 72° C. for 10 min. Reaction mix consisted of 50 ng genomic DNA, 0.1 µmol of each primer, and HotStart Taq Master Mix (Qiagen, Europe) in a reaction mix of 10 µL. Linkage analysis to the DMD locus was performed using standard techniques as will be described under 'Linkage analysis.' Five polymorphic STR microsatellite markers surrounding the DMD gene, STR-44 (DXS1238; 180-210 bp), STR-45 (DXS1237; 160-185 bp), STR-48 (DXS997; 105-120 bp), STR-49 (DXS1236; 230-260 bp), and STR-50 (DXS1235; 230-260 bp), were selected for this purpose. Forward primers were labelled at their 5' ends with either 5-carboxyfluorescein (FAM) or NED fluorochromes. STR-44 (forward primer: TCC AAC ATT GGA AAT CAC ATT TCA A (SEQ ID NO:29); reverse primer: TCA TCA CAA ATA GAT GTT TCA CAG (SEQ ID NO:30)), STR-45 (forward primer: GAG GCT ATA ATT CTT TAA CTT TGG C (SEQ ID NO:31); reverse primer: CTC TTT CCC TCT TTA TTC ATG TTA C (SEQ ID NO:32)), STR-48 (forward primer: GCT GGC TTT ATT TTA AGA GGA (SEQ ID NO:33); reverse primer: GGT TTT CAG TTT CCT GGG TA (SEQ ID NO:34)), STR-49 (forward primer: CGT TTA CCA GCT CAA AAT CTC AAC (SEQ ID NO:35); reverse primer: CAT ATG ATA CGA TTC GTG TTT TGC (SEQ ID NO:36)), and STR-50 (forward primer: AAG GTT CCT CCA GTA ACA GAT TTG G (SEQ ID NO:37); reverse primer: TAT GCT ACA TAG TAT GTC CTC AGA C (SEQ ID NO:38)).

Genome-Wide SNP Analysis: Mapping of a New Locus to Xq26-q27

A genome-wide 250 K NspI Affymetrix SNP microarray was performed on five affected cases (individuals 20, 29, 50, 11, and 45) and three unaffected relatives at the Microarray Facility at The Centre for Applied Genomics (Toronto, Canada). Capable of genotyping on average 250,000 SNPs, the single nucleotide polymorphisms are separated by a median physical distance of 2.5 Kb and an average distance of 5.8 Kb between SNPs (Affymetrix, Calif., USA). The average heterozygosity of these SNPs is 0.30, with approximately 85% of the human genome found within 10 Kb of a SNP. SNP microarray gene chip data was subsequently analyzed using dCHIP software.

Linkage Analysis

Multipoint X-recessive nonparametric linkage was computed using easyLINKAGE plus v5.02. Allele frequencies were considered equal. One cM was assumed to be equivalent to 1 Mb.

Sequencing and Mutation Analysis of Candidate Genes (MBNL3, VGLL1, FGF13)

The National Center for Biotechnology Information Entrez Genome Map Viewer, Ensembl Human Genome Server and GenBank databases were employed to locate known genes, expressed-sequence tags and putative new genes that map to Xq26-q27. Exon-intron boundaries of the candidate sequences were determined by BLAST searches against the human genome sequence database at the National Center for Biotechnology Information. Intronic primers (primer sequences available on request) were used to amplify all exons of the functional candidate genes by PCR. PCR products were sequenced using the BigDye® Terminator 3.1 Cycle Sequencing Kit (Perkin-Elmer, Applied Biosystems). Sequencing reactions were loaded on the ABI Prism® 3100 DNA Analyzer (Perkin-Elmer, Applied Biosystems) and generated data was collected using the ABI® DATA COLLECTION version 1.1, and subsequently analyzed using the DNA SEQUENCING ANALYSIS version 3.6 software. Sequencing and mutation analysis were performed at the Centre for Addiction and Mental Health (Toronto, Canada).

Example 2: Identification and Characterization of a Novel X-Linked Muscular Myopathy This current study is the first to describe a family affected by a mild X-linked MD that specifically features atrophy that is limited mainly to type I muscle fibers in postural muscles. This large multigenerational Austrian family originates from the Czech republic, and six living affected members have been ascertained and examined to date. Pedigree analysis (FIG. 1) shows an X-linked pattern of inheritance. Clinical assessment in all six patients as well as two now-deceased patients from this family revealed a fairly uniform and characteristic phenotype (See Table 1). All subjects appeared to show an athletic stature (FIG. 2), however more detailed examination revealed an almost selective atrophy and wasting of postural muscles, while other muscles were hypertrophic. Predominantly weak and atrophic muscles include the soleus, peroneus longus, tibialis anterior, vastus medialis, erector spinae, lower part of the latissimus dorsi, and abductor pollicis muscles. Additionally, all patients had significant contractures of the Achilles tendon and hamstrings, a short neck and also a mechanically limited range of neck flexion and extension. Tendon reflexes, sensory examination and mental status were normal. In all affected individuals scoliosis, back pain, gait problems and elevated creatine kinase levels were noted. The pseudo-athletic musculature is likely to be a compensatory response to the atrophy of the postural muscles. Cases were asymptomatic until the age of 30, and in six deceased family members who had suffered from the disease there was a wide range in age of death (45-72 years), typically from heart failure but of unknown mechanism. It appears that family members with more active lifestyles show less severe phenotypes and slower progression of disease.

Muscle biopsies from affected individuals revealed dystrophic changes in postural muscles with variation in fiber sizes, degeneration of muscle endurance type I fibers, increased fatty and connective tissue, and multinucleated sarcomeres (FIG. 3). Immunocytochemical staining of biopsied muscle tissue revealed no deficiencies of proteins associated with either autosomal or X-linked forms of MD, including dystrophin and emerin. This is consistent with the clinical and apparent epidemiological differences that distinguish and typify this new type of MD. Myosin ATPase staining revealed a gradual atrophy of high-oxidative, low-glycolytic, endurance type I muscle fibers in postural muscles. While patients in the early stages of the disease show a relatively normal distribution of type I and type II fibers, as the disease progresses there are decreased numbers of type I fibers, which appear atrophied (FIG. 4). Non-postural muscles, including, among others, the gluteus medius, gluteus maximus, biceps brachii, triceps brachii, lower arms, latissimus dorsi, and extensor muscles, appear normal with respect to muscle fiber distribution and function (Table 2).

Three different antibodies were used to detect distinct domains of the dystrophin protein. Staining was faint, but not significantly different than unaffected individuals, suggesting this family does not display a variant form of DMD or Becker's MD. Adhalin staining was performed, which excluded autosomal-recessive limb-girdle MD 2C (LGMD2C), LDMD2D, LGMD2E, and LGMD2F. Normal merosin staining excluded congenital MD. Staining for dysferlin and caveolin allowed for exclusion of LGMD2B and LGMD1C, respectively. LGMD1I was excluded following α-dystroglycan staining. The likelihood of this postural MD representing a variant form of X-recessive EDMD was diminished following normal emerin staining. LGMD2D (Duchenne-like autosomal-recessive MD) and spinocerebellar ataxia type 5 (SCA5) were excluded following α-sarcoglycan (LGMD2D) and spectrin (SCA5) staining. Normal staining for lamin A/C, desmin, and β-slow myosin heavy chain excluded autosomal-dominant EDMD2 and LGMD1B (lamin A/C), desminopathies (desmin), and distal myopathy MPD 1 (myosin), respectively. Myotonic dystrophy 2 (DM2) and proximal myotonic myopathy (PROMM) were also suggested as possible causative factors, but molecular genetic analysis revealed no mutations.

Immunocytochemical data and pedigree analysis suggested that this family displays an unsevere myopathy with multinucleated sarcomeres and a pattern of recessive X-chromosome inheritance. To exclude the possibility that the phenotype in this family is a variant form of DMD or Becker's MD, we performed linkage analysis to the DMD locus using five selected polymorphic STR microsatellite markers surrounding the DMD gene; STR-44 (DXS1238), STR-45 (DXS1237), STR-48 (DXS997), STR-49 (DXS1236), and STR-50 (DXS1235). Different haplotypes were revealed in the affecteds across the DMD locus, excluding this locus as the causative gene in this family. Recombination of the intragenic markers STR-44, STR-48, STR-49 and STR-50 was evident (FIG. 5). Subsequent screening for mutations in the DMD gene was conducted by sequencing cDNA proximal to the area spanned by the intragenic markers, which ruled out intragenic recombination. Genotypes for markers across the X-chromosome were analyzed. Multipoint lod scores were found to be significant for the Xq26-q27 region (lod>3), giving further confirmation for exclusion of the DMD locus. Multipoint lod scores revealed positive, non-significant results for areas surrounding the candidate interval that was later specified by SNP analysis (FIG. 5). A genome-wide SNP genotype analysis was performed on the five affected individuals along with three unaffected family members at The Centre for Applied Genomics (Toronto, Canada). A ~250K NspI Affymetrix SNP micorarray was used, and subsequent analysis using dCHIP implicated a candidate region on Xq26-q27, the candidate region encompasses approximately 850 consecutive SNPs.

Three candidate genes from the Xq26-q27 critical region that encode structural proteins expressed in muscle were screened. The muscleblind-like protein 3 (MBNL3), vestigial-like 1 (VGLL1) gene fibroblast growth factor 13 (FGF13) were all sequenced from genomic DNA, but no coding mutations were identified.

Sequencing of the coding and 5'UTR region of FHL1 (NM_001449) resulted in a transversion at position 672 C to G leading to the amino acid substitution C224W. This mutation co-segregated with disease status within the family, all 6 affected subjects were hemizygous and all obligate carriers were heterozygous for the mutated allele. The mutation was not detected in mixed Caucasian and Austrian control chromosomes.

FHL1 is a member of LIM-only proteins, containing four and a half LIM domains with a common consensus sequence C-X2-C-X16-21-H-X2-C-X2-C-X2-C-X17-C-X2-C. LIM only proteins are zinc-binding proteins that are known to be play a role in cell signaling and transcriptional regulation. So far, 5 FHL proteins have been identified: FHL1-5 are known to act as transcription regulators.

The C224W mutation replaces a highly conserved cysteine of the fourth LIM domain of FHL1 which is one of the four cysteines needed for the central binding of a zinc ion. Mutations of conserved cysteines that are part involved in zinc binding have been shown to have a highly deleterious effect on the tertiary structure of the protein (Taira et al, 1994). Furthermore, the C224W mutation also is located in the first nuclear localization signal (NLS 1) of the alternatively expressed isoform FHL1b (SLIMMER), which might lead to impaired FHL1b protein from shuttle between the cytoplasm and the nucleus (Brown S et al; J Biol Chem. 1999 Sep. 17; 274(38):27083-91

FHL1 has at least 3 different isoforms (a, b and c), each with different tissue specificities. The C224W mutation affects FHL1 isoforms a (the most prevalent isoform) and b, but not isoform c. Hence, mutations within different regions of the gene may affect specific isoforms, with other isoforms unaffected, and thus may have different phenotypic consequences. Furthermore, FHL1 has a number of protein binding partners that bind to different LIM domains within the protein, and thus a mutation affecting the conformation of one LIM domain may have different phenotypic consequences to a mutation affecting a different LIM domain.

In summary, we have identified the gene FHL1, and its encoded protein, as responsible for a new form of muscular myopathy, XMPMA. The phenotypic features described in the Austrian family, in particular the specific atrophy of postural muscles and pseudo athleticism, may be specific for mutations within the SRF and MyBPC1 (muscle fiber type 1-specific isoform) and ERK2 binding regions of FHL1. Mutations elsewhere in the gene may result in a much more heterogeneous myopathic phenotype. This has considerable implications for diagnostic evaluation, screening and genetic counseling for patients (also carriers) with muscular or myotonic dystrophy of unknown genetic cause, in particular where the familial nature indicates X-linked inheritance and where the Becker's/Duchenne's MD and Emery-Dreifuss MD loci have been excluded, but also for sporadic cases. Additional information concerning this example may be obtained from Windpassinger et al., The American Journal of Human Genetics 82, 88-99, January 2008 which is herein incorporated by reference.

Example 3: UK Pedigrees (Families 2 an 3) Exhibiting Muscular Myopathies

Four 4 male individuals in 3 consecutive generations presented with slowly progressive hip and arm weakness with onset in the 3rd-4th decades. The index patient showed prominent shoulder girdle and arm hypertrophy, with CK levels elevated to 1300 U/l. Respiratory failure was reported in two patients who died in their 50s. The UK family 2 pedigree is shown in FIG. 1B.

A third family, with a putative diagnosis of Becker muscular dystrophy was identified, where 6 females and 6 males, spread over 5 generations, were affected. The UK family 3 pedigree is shown in FIG. 1C. In male patients, age at onset was in the late teens-3rd decade, and presenting clinical symptoms were progressive limb-girdle weakness with prominent scapular winging. Muscle hypertrophy was not a prominent feature, while neck/cervical rigidity or weakness and Achilles tendon contractures were reported in three patients. CK levels were around 1500-2200 U/l. Two patients were wheelchair bound from their 30s. Respiratory and heart failure in the late 40s-50s were the causes of death in 2 patients. Female mutation carriers presented with a similar but milder clinical picture with onset in the 5th decade or later and CK levels only slightly elevated at 300 U/l. One female patient died at the age of 88 years due to congestive heart failure. The index patient presented with first symptoms of hip flexor weakness (MRC 4) and elevated serum CK levels of around 1300 U/l at the age of 35 years. At that time he was playing competitive football and showed a very athletic habitus. Muscle hypertrophy was most prominent in his shoulder girdle and arm muscles. Neck flexion was compromised by spinal rigidity. His lung function showed a FVC of 4.6 l (90%) in a sitting position and dropped to 4.0 l (78%) in a lying position. There were no additional clinical signs or symptoms of an underlying skeletal muscle or heart disease. Nerve conduction studies and an EMG were normal. A muscle biopsy from the vastus lateralis showed type I fibre atrophy, variation in fibre size, with some measuring up to 125 μm in diameter, and a few necrotic fibres. Immunohistochemical and Western blot analysis for proteins of the dystrophin glycoprotein complex, emerin, dysferlin, caveolin and calpain were normal. Mutation analysis of the genes for dystrophin and emerin did not reveal any abnormalities. The maternal grandfather of the index patient started to experience difficulties with walking at 42 years of age and used a wheelchair for the last years of his life. He died of respiratory failure at 52 with the label of Becker muscular dystrophy. Two nephews of the grandfather were also labeled with Becker muscular dystrophy and experienced slowly progressive muscle weakness in legs and arms from their early 40ies. One of them died in his 50's of respiratory failure.

Data for the Index Patient, Family 2:
Age of onset: 35
CK: 1342 U/L
EMG: normal
Muscle MRI: N.D.
Athletic habitus in early stages: yes
Muscle biopsy: myopathic
Cardiac involvement: normal heart evaluation
Neck and Achilles tendons: short (AT)

The mutation c.381_382insATC (leading to p.Phe127_Thr128insIle) was identified in the index patients of both families and segregates with the phenotype. The F127_T128InsI mutation occurs within the second LIM domain, and thus is present in all three isoforms of FHL1, a, b and c. In conclusion, the data presented herein shows that the same FHL1 mutation may give rise to heterogeneous phenotypes, with X-linked recessive or dominant inheritance.

Example 4: Study of Cardiomyopathies in the Austrian XMPMA Family

Patients with the clinical diagnosis of XMPMA and their immediate relatives were invited to participate in a study for cardiovascular investigation of XMPMA. Standard 12 lead ECGs were recorded in the recumbent position. The echocardiographic studies were all performed by one operator using a GE Vivid 7 scanner. Measurements were made according to the standards of the American Society of Echocardiography and analyses were performed using the software programs of the scanner. The doppler variables measured were the peak aortic and LVOT velocities, and transmitral flow for assessing the diastoly. Strain and strain rate measurements were obtained by the non-Doppler 2D strain imaging technique as well as with TDI technique. Genomic DNA and serum profile (enzymes) were extracted from blood samples with standard procedures. Also used were: Magnet Resonance Imaging; Intracardiac catheter with biopsy of the left ventricle; Treadmill testing; ECG Holter monitoring.

The most common abnormality was T-wave inversion in V4-V6 and other ST-T wave changes, partly signs of left ventricular hypertrophy. All affected family members had pathological treadmill tests with ST wave changes and arrhythmia with extrasystoles (whereas Holter ECG has not been done yet). Left ventricular hypertrophy with thickening confined to the apex as well as involvement of the right ventricle was present in all affected family members. The left ventricle was normal in size with normal systolic but impaired diastolic function. No abnormalities of the mitral valve and its supporting structures were seen, and no LVOT gradient. All affected patients had a dilated left atrium and increased left atrial volume. Tissue velocities, strain rate and strain are also reduced. All affected male members had elevated levels of serum creatinine kinase, CK-MB, LDH, NT-pro BNP, Trop T and liver enzymes. Without wishing to be limiting in any manner, important clinical findings included symptoms from Dyspnoe New York Heart association class II.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Affymetrix Inc. 2006. GeneChip® Human Mapping 500K Array Set.

Bione S, Maestrini E, Rivella S, Mancini M, Regis S, Romeo G, Toniolo D. Identification of a novel X-linked gene responsible for Emery-Dreifuss muscular dystrophy. *Nat Genet* 1994; 8: 323-7.

Blanco G, Coulton G R, Biggin A, Grainge C, Moss J, Barrett M, Berquin A, Marechal G, Skynner M, van Mier P, Nikitopoulou A, Kraus M, Ponting C P, Mason R M, Brown S D. The kyphoscoliosis (ky) mouse is deficient in hypertrophic responses and is caused by a mutation in a novel muscle-specific protein. *Hum Mol Genet* 2001; 10: 9-16.

Carsana A, Frisso G, Tremolaterra M R, Ricci E, De Rasmo D, Salvatore F. A larger spectrum of intragenic short tandem repeats improves linkage analysis and localization of intragenic recombination detection in the dystrophin gene: an analysis of 93 families from southern Italy. *J Mol Diagn* 2007; 9: 64-9.

Davies K E, Nowak K J. Molecular mechanisms of muscular dystrophies: old and new players. *Nat Rev Mol Cell Biol* 2006; 7: 762-73.

Ellis J A. Emery-Dreifuss muscular dystrophy at the nuclear envelope: 10 years on. *Cell Mol Life Sci* 2006; 63: 2702-9.

Ervasti J M. Dystrophin, its interactions with other proteins, and implications for muscular dystrophy. *Biochim Biophys Acta* 2007; 1772: 108-17.

Fukuda M. Biogenesis of the lysosomal membrane. *Subcell Biochem* 1994; 22: 199-230.

Fukuda M, Viitala J, Matteson J, Carlsson S R. Cloning of the cDNAs encoding human lysosomal membrane glycoproteins, h-lamp-1 and h-lamp-2: comparison of their deduced amino acid sequences. *J Biol Chem* 1988; 263: 18920-18928.

Gecz J, Baker E, Donnelly A, Ming J E, McDonald-McGinn D M, Spinner N B, Zackai E H, Sutherland G R, Mulley J C. Fibroblast growth factor homologous factor 2 (FHF2): gene structure, expression and mapping to the Borjeson-Forssman-Lehmann syndrome region in Xq26 delineated by a duplication breakpoint in a BFLS-like patient. *Hum Genet* 1999; 104: 56-63.

Gudbjartsson D F, Jonasson K, Frigge M L, Kong A. Allegro, a new computer program for multipoint linkage analysis. *Nat Genet* 2000; 25: 12-3.

Ho M, Chelly J, Carter N, Danek A, Crocker P, Monaco A P. Isolation of the gene for McLeod syndrome that encodes a novel membrane transport protein. *Cell* 1994; 77: 869-880.

Hoffmann K, Lindner T H. easyLINKAGE-Plus-automated linkage analyses using large-scale SNP data. *Bioinformatics* 2005; 21: 3565-7.

Maeda T, Chapman D L, Stewart A F R. Mammalian vestigial-like 2, a cofactor of TEF-1 and MEF2 transcription factors that promotes skeletal muscle differentiation. *J Biol Chem* 2002; 277: 48889-48898.

Marsh W L, Marsh N J, Moore A, Symmans W A, Johnson C L, Redman C M. Elevated serum creatine phosphokinase in subjects with McLeod syndrome. *Vox Sang* 1981; 40: 403-411.

Miller J W, Urbinati C R, Teng-umnuay P, Stenberg M G, Byrne B J, Thornton C A, Swanson M S. Recruitment of human muscleblind proteins to (CUG)n expansions associated with myotonic dystrophy. *EMBO J* 2000; 19: 4439-4448.

Nowak K J, Wattanasirichaigoon D, Goebel H H, Wilce M, Pelin K, Donner K, Jacob R L, Hubner C, Oexle K, Anderson J R, Verity C M, North K N, Iannaccone S T, Muller C R, Nurnberg P, Muntoni F, Sewry C, Hughes I, Sutphen R, Lacson A G, Swoboda K J, Vigneron J, Wallgren-Pettersson C, Beggs A H, Laing N G. Mutations in the skeletal muscle alpha-actin gene in patients with actin myopathy and nemaline myopathy. *Nature Genet* 1999; 23: 208-212.

Schadt E E, Li C, Ellis B, Wong W H. Feature extraction and normalization algorithms for high-density oligonucleotide gene expression array data. *J Cell Biochem* 2001; 37: 120-5.

Taira M, Otani H, Saint-Jearmet J P, Dawid I B. Role of the LIM class homeodomain protein Xlim-1 in neural and muscle induction by the Spemann organizer in *Xenopus*. *Nature*. 1994 372:677-679.

Vaudin P, Delanoue R, Davidson I, Silber J, Zider A. TONDU (TDU), a novel human protein related to the product of vestigial (vg) gene of *Drosophila melanogaster* interacts with vertebrate TEF factors and substitutes for Vg function in wing formation. *Development* 1999; 126: 4807-4816.

Yasuda S. Townsend D, Michele D E, Favre E G, Day S M, Metzger J M. Dystrophic heart failure blocked by membrane sealant poloxamer. *Nature* 2005; 436: 1025-9.

TABLE 1

Clinical evaluations for members of the XMPMA family from Austria, including electromyogram, NCV, muscle MRI, histological examination of biopsied tissue, and involvement of heart, and of tendons in neck and Achilles heel.

| Patients ID | Age of onset | CK level | EMG | NCV studies | Muscle MRI | Athletic habitus at onset | Muscle biopsie | Heart affection | Neck and Achilles tendon |
|---|---|---|---|---|---|---|---|---|---|
| SK060666 | 26 | 620 | myopathic | normal | Nd | yes | nd | ? | |
| FM240432 | 30 | 500-900 | myopathic | normal | Nd | yes | myopathic | Cardio myopathy with arrhythmia | short |
| AJ020657 | 32 | 620 | | normal | Selective muscle atrophie, bent spine | yes | myopathic | Dialtativ cardio myopathy hypertrophic | short |
| AA030554 | 32 | 400-1774 | myopathic | normal | Selectiv muscle atrophy, bent spine | yes | myopathic | Normal heart evaluation | short |
| AF061160 | 30 | 780 | myopathic | normal | — | yes | nd | Unkown | short |
| MF250358 | 30 | 700 | myopathic | normal | Selective muscle atrophy bent spine | yes | myopathic | Hypertrophic cardiomyopathy | short |
| MW211168 | 31 | 550 | myopathic | normal | Nd | unkown | myopathic | Hypertrophic cardiomyopathy | short |
| BJ180830 | 30 | 800-1200 | myopathic | normal | -nd | yes | myopathic | Respiratory failure | short |

TABLE 2

Type I and type II muscle fibre distribution in several muscles in a patient in progressed stages of disease. Muscles represented in bold display significantly high portion of type I muscle fibres. There is a pronounced decrease in the proportion of type I muscle fibres in postural muscles; adductor magnus, biceps femoris, deltoideus, peronaeus longus, soleus, tibialis anterior, and vastus medialis muscles showed gradual atrophy of type I slow-twitch muscle fibres, whereas many muscles with a high percentage of fiber type II show mild to pronounced hypertrophy.

| Muscle | Typ I | Typ II | atrophic | hypertrophic | normal |
|---|---|---|---|---|---|
| Abductor digiti minimi | 51.8 | 48.2 | | | X |
| Abductor pollicis brevis | 63.0 | 37.0 | | | X |
| Abductor hallucis | | | | | X |
| Adductor magnus (surface) | 53.5 | 46.5 | | | |
| Adductor magnus (deep) | 63.3 | 36.7 | X | | |
| Adductor pollicis | 80.4 | 19.6 | | | ? |
| Biceps brachii (surface) | 42.3 | 57.7 | | X | |
| Biceps brachii (Deep) | 50.5 | 49.5 | | X | |
| Biceps fernoris | 66.9 | 33.1 | X | | |
| Brachioradialis | 39.8 | 60.2 | | | X |
| Deltoideus (Surface) | 53.3 | 46.7 | X | | |
| Deltoideus (Deep) | 61.0 | 39.0 | X | | |
| I dorsal interosseus | 57.4 | 42.6 | | | X |
| Erector spinae (Surface) | 58.4 | 41.6 | X | | |
| Erector spinae (Deep) | 54.9 | 45.1 | X | | |
| Extensor digitorum | 47.3 | 52.7 | | X | |
| Extensor digitorum brevis | 45.3 | 54.7 | | X | X |
| Flexor digitorum brevis | 44.5 | 55.5 | | X | |
| Flexor digitorum profundus | 47.3 | 52.7 | | X | |
| Frontalis | 64.1 | 35.9 | | | ? |
| Gastrocnemius (lat. head. Surface) | 43.5 | 56.5 | X | | |
| Gastrocnemius (lat. head. Deep) | 50.3 | 49.7 | X | | |
| Gastrocnemius (medial head) | 50.8 | 49.2 | X | | |
| Gluteus medius | | | | | X |
| Gluteus maximus | 52.4 | 47.6 | | | X |
| Iliopsoas | 49.2 | 50.8 | | | ? |
| Iliocostalis | | | | X | |
| Interspinales cervicis | | | | X | |
| Infraspinatus | 45.3 | 54.7 | | X | |
| Longus capitis | | | | | X |
| Longus colli | | | | | X |
| Longisimus dorsi | | | | X | |
| Latissimus dorsi | 50.5 | 49.5 | | | X |
| multifidus | | | | X | |
| Orbicularis oculi | 15.4 | 84.6 | | | X |
| Obliqus capitis | | | | X | |
| Pectoralis major (clavic. head) | 42.3 | 57.7 | | | ? |
| Pectoralis major (sternal head) | 43.1 | 56.9 | | | ? |
| Peronaeus longus | 62.5 | 37.5 | X | | |
| Psoas | | | | | X |
| Rectus abdominis | 46.1 | 53.9 | | X | |
| Rectus femoris (lat. head. Surface) | 29.5 | 10.5 | | | X |
| Rectus femoris (lat. head. Deep) | 42.0 | 58.0 | | | X |
| Rectus femoris (medial head) | 42.8 | 57.2 | | | X |
| Rhomboideus | 44.6 | 55.4 | | X | X |
| Sartorius | 49.6 | 50.4 | | | |
| Semimembranosus | | | | X | |
| semispinalis | | | | X | |
| Soleus (Surface) | 86.4 | 13.6 | X | | |
| Soleus (Deep) | 89.0 | 11.0 | X | | |
| Splenius | | | | | X |
| Sternocleidomastoideus | 35.2 | 64.8 | | X | X |

TABLE 2-continued

Type I and type II muscle fibre distribution in several muscles in a patient in progressed stages of disease. Muscles represented in bold display significantly high portion of type I muscle fibres. There is a pronounced decrease in the proportion of type I muscle fibres in postural muscles; adductor magnus, biceps femoris, deltoideus, peronaeus longus, soleus, tibialis anterior, and vastus medialis muscles showed gradual atrophy of type I slow-twitch muscle fibres, whereas many muscles with a high percentage of fiber type II show mild to pronounced hypertrophy.

| Muscle | Typ I | Typ II | atrophic | hypertrophic | normal |
|---|---|---|---|---|---|
| Supraspinatus | 59.3 | 40.7 | X | | |
| Temporalis | 46.5 | 53.5 | | | X |
| Tibialis anterior (Surface) | 73.4 | 26.6 | X | | |
| Tibialis anterior (Deep) | 72.7 | 27.3 | X | | |
| Trapezius | 53.7 | 46.2 | X | | X |
| Transversus occipitalis | | | | | |
| Triceps surae | | | | X | |
| Triceps (Surface) | 32.5 | 67.5 | | X | |
| Triceps (Deep) | 32.7 | 67.3 | | X | |
| Vastus lateralis (Surface) | 37.8 | 62.2 | | X | |
| Vastus lateralis (Deep) | 46.9 | 53.1 | X | | |
| Vastus medialis (surface) | 43.7 | 56.3 | | | X |
| Vastus medialis (Deep) | 61.5 | 38.5 | X | | |

JOHNSON et al. (1973).

What is claimed is:

1. A protein comprising amino acids 1-230 of SEQ ID NO:1, or a fragment thereof comprising the amino acid sequence VAKKCX$_1$GX$_2$X$_3$NPIT (SEQ ID NO:4) wherein X$_2$ corresponds to position 224 of SEQ ID NO: 1 and is any amino acid except C; and X$_1$ and X$_3$ are independently any amino acid.

2. The protein as defined in claim 1, wherein X$_2$ is tryptophan.

3. The protein of claim 1, defined by SEQ ID NO:2 or SEQ ID NO:3.

4. A nucleic acid comprising:
   a) a sequence encoding the amino acid sequence VAKKCX$_1$GX$_2$X$_3$NPIT (SEQ ID NO:4) wherein X$_2$ corresponds to position 224 of SEQ ID NO: 1 and is any amino acid except C; and X$_1$ and X$_3$ are independently any amino acid; or
   b) the full-length complement of the sequence of a);
   wherein the nucleic acid is capable of hybridizing to a sequence encoding a protein comprising amino acids 1-230 of SEQ ID NO:1, a fragment thereof, or a sequence exhibiting at least 95% identity to the protein under stringent hybridization conditions.

5. The nucleic acid of claim 4, wherein the fragment comprises the amino acids sequence GWK.

6. The nucleic acid of claim 4, wherein X$_2$ is tryptophan.

7. The nucleic acid of claim 4, wherein the protein is defined by SEQ ID NO:2 or SEQ ID NO:3.

8. A method of screening a subject for an X-linked muscular myopathy comprising:
   a) obtaining a biological sample from the subject, and;
   b) assaying the sample for a nucleic acid encoding a protein comprising the amino acid sequence VAKKCX$_1$GX$_2$X$_3$NPIT (SEQ ID NO:4) wherein X$_2$ corresponds to position 224 of SEQ ID NO: 1 and is any amino acid except C; and X$_1$ and X$_3$ are independently any amino acid, or
   c) assaying the sample for a protein comprising the amino acid sequence VAKKCX$_1$GX$_2$X$_3$NPIT (SEQ ID NO:4) wherein X$_2$ corresponds to position 224 of SEQ ID NO: 1 and is any amino acid except C; and X$_1$ and X$_3$ are independently any amino acid, wherein detection of the nucleic acid or protein indicates that the subject has an X-linked muscular myopathy.

9. The method as defined in claim 8 wherein X$_2$ is tryptophan.

10. The method as defined in claim 8 wherein the protein is defined by SEQ ID NO:2 or SEQ ID NO:3.

11. The method of claim 8, wherein the subject is a human subject.

12. The method of claim 8, wherein the biological sample is a blood sample.

13. The method of claim 8, wherein assaying comprises PCR, probe hybridization, immunohistochemistry, nucleotide sequencing or protein sequencing.

14. The method of claim 8, which is conducted using a kit comprising:
   i) a protein or fragment thereof that is associated with muscular myopathy as defined
   ii) an antibody that selectively binds to a protein or fragment thereof associated with muscular myopathy as defined herein, as compared to a wild-type protein not associated with muscular myopathy,
   iii) one or more nucleic acid primers to amplify a nucleotide sequence encoding a protein or fragment thereof which comprises a mutation associated with an X-linked muscular myopathy as provided herein,
   iv) one or more nucleic acid probes that hybridizes nucleotide sequence encoding a protein or fragment thereof which comprises a mutation associated with an X-linked muscular myopathy as provided herein,
   v) one or more reagents including, but not limited to buffer(s), dATP, dTTP, dCTP, dGTP, or DNA polymerase(s),
   vi) instructions for assaying, diagnosing or determining the risk of a subject to muscular myopathy,
   vii) instructions for using any component or practicing any method as described herein, or any combination thereof.

15. The method of claim 8, wherein the muscular myopathy is a skeletal muscle myopathy or a cardiomyopathy.

16. The method of claim 15, wherein the muscular myopathy is muscular dystrophy.

* * * * *

SEQUENCE LISTING

```
<160> NUMBER OF SEQ ID NOS: 41

<210> SEQ ID NO 1
<211> LENGTH: 230
<212> TYPE: PRT
<213> ORGANISM: homo sapiens
<220> FEATURE:
<221> NAME/KEY: misc_feature
<222> LOCATION: (224)..(224)
<223> OTHER INFORMATION: Xaa can be any naturally occurring amino acid

<400> SEQUENCE: 1

Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
            20                  25                  30

Asp Lys Phe Cys Ala Asn Thr Cys Val Glu Cys Arg Lys Pro Ile Gly
        35                  40                  45

Ala Asp Ser Lys Glu Val His Tyr Lys Asn Arg Phe Trp His Asp Thr
    50                  55                  60

Cys Phe Arg Cys Ala Lys Cys Leu His Pro Leu Ala Asn Glu Thr Phe
65                  70                  75                  80

Val Ala Lys Asp Asn Lys Ile Leu Cys Asn Lys Cys Thr Thr Arg Glu
                85                  90                  95

Asp Ser Pro Lys Cys Lys Gly Cys Phe Lys Ala Ile Val Ala Gly Asp
            100                 105                 110

Gln Asn Val Glu Tyr Lys Gly Thr Val Trp His Lys Asp Cys Phe Thr
        115                 120                 125

Cys Ser Asn Cys Lys Gln Val Ile Gly Thr Gly Ser Phe Phe Pro Lys
    130                 135                 140

Gly Glu Asp Phe Tyr Cys Val Thr Cys His Glu Thr Lys Phe Ala Lys
145                 150                 155                 160

His Cys Val Lys Cys Asn Lys Ala Ile Thr Ser Gly Gly Ile Thr Tyr
                165                 170                 175

Gln Asp Gln Pro Trp His Ala Asp Cys Phe Val Cys Val Thr Cys Ser
            180                 185                 190

Lys Lys Leu Ala Gly Gln Arg Phe Thr Ala Val Glu Asp Gln Tyr Tyr
```

```
                     195                 200                 205
Cys Val Asp Cys Tyr Lys Asn Phe Val Ala Lys Lys Cys Ala Gly Xaa
    210                 215                 220

Lys Asn Pro Ile Thr Gly
225                 230

<210> SEQ ID NO 2
<211> LENGTH: 280
<212> TYPE: PRT
<213> ORGANISM: homo sapiens

<400> SEQUENCE: 2

Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
            20                  25                  30

Asp Lys Phe Cys Ala Asn Thr Cys Val Glu Cys Arg Lys Pro Ile Gly
        35                  40                  45

Ala Asp Ser Lys Glu Val His Tyr Lys Asn Arg Phe Trp His Asp Thr
    50                  55                  60

Cys Phe Arg Cys Ala Lys Cys Leu His Pro Leu Ala Asn Glu Thr Phe
65                  70                  75                  80

Val Ala Lys Asp Asn Lys Ile Leu Cys Asn Lys Cys Thr Thr Arg Glu
                85                  90                  95

Asp Ser Pro Lys Cys Lys Gly Cys Phe Lys Ala Ile Val Ala Gly Asp
            100                 105                 110

Gln Asn Val Glu Tyr Lys Gly Thr Val Trp His Lys Asp Cys Phe Thr
        115                 120                 125

Cys Ser Asn Cys Lys Gln Val Ile Gly Thr Gly Ser Phe Phe Pro Lys
    130                 135                 140

Gly Glu Asp Phe Tyr Cys Val Thr Cys His Glu Thr Lys Phe Ala Lys
145                 150                 155                 160

His Cys Val Lys Cys Asn Lys Ala Ile Thr Ser Gly Gly Ile Thr Tyr
                165                 170                 175

Gln Asp Gln Pro Trp His Ala Asp Cys Phe Val Cys Val Thr Cys Ser
            180                 185                 190

Lys Lys Leu Ala Gly Gln Arg Phe Thr Ala Val Glu Asp Gln Tyr Tyr
        195                 200                 205

Cys Val Asp Cys Tyr Lys Asn Phe Val Ala Lys Lys Cys Ala Gly Trp
    210                 215                 220

Lys Asn Pro Ile Thr Gly Phe Gly Lys Gly Ser Ser Val Val Ala Tyr
225                 230                 235                 240

Glu Gly Gln Ser Trp His Asp Tyr Cys Phe His Cys Lys Lys Cys Ser
                245                 250                 255

Val Asn Leu Ala Asn Lys Arg Phe Val Phe His Gln Glu Gln Val Tyr
            260                 265                 270

Cys Pro Asp Cys Ala Lys Lys Leu
        275                 280

<210> SEQ ID NO 3
<211> LENGTH: 323
<212> TYPE: PRT
<213> ORGANISM: homo sapiens

<400> SEQUENCE: 3

Met Ala Glu Lys Phe Asp Cys His Tyr Cys Arg Asp Pro Leu Gln Gly
```

```
              1               5              10              15
            Lys Lys Tyr Val Gln Lys Asp Gly His His Cys Cys Leu Lys Cys Phe
                            20              25              30

Asp Lys Phe Cys Ala Asn Thr Cys Val Glu Cys Arg Lys Pro Ile Gly
                        35              40                  45

Ala Asp Ser Lys Glu Val His Tyr Lys Asn Arg Phe Trp His Asp Thr
                    50                  55              60

Cys Phe Arg Cys Ala Lys Cys Leu His Pro Leu Ala Asn Glu Thr Phe
            65              70              75                      80

Val Ala Lys Asp Asn Lys Ile Leu Cys Asn Lys Cys Thr Thr Arg Glu
                            85              90              95

Asp Ser Pro Lys Cys Lys Gly Cys Phe Lys Ala Ile Val Ala Gly Asp
                        100             105             110

Gln Asn Val Glu Tyr Lys Gly Thr Val Trp His Lys Asp Cys Phe Thr
                    115             120             125

Cys Ser Asn Cys Lys Gln Val Ile Gly Thr Gly Ser Phe Phe Pro Lys
            130             135             140

Gly Glu Asp Phe Tyr Cys Val Thr Cys His Glu Thr Lys Phe Ala Lys
            145             150             155             160

His Cys Val Lys Cys Asn Lys Ala Ile Thr Ser Gly Gly Ile Thr Tyr
                            165             170             175

Gln Asp Gln Pro Trp His Ala Asp Cys Phe Val Cys Val Thr Cys Ser
                        180             185             190

Lys Lys Leu Ala Gly Gln Arg Phe Thr Ala Val Glu Asp Gln Tyr Tyr
                    195             200             205

Cys Val Asp Cys Tyr Lys Asn Phe Val Ala Lys Lys Cys Ala Gly Trp
            210             215             220

Lys Asn Pro Ile Thr Gly Lys Arg Thr Val Ser Arg Val Ser Arg Pro
            225             230             235             240

Val Ser Lys Ala Arg Lys Pro Pro Val Cys His Gly Lys Arg Leu Pro
                            245             250             255

Leu Thr Leu Phe Pro Ser Ala Asn Leu Arg Gly Arg His Pro Gly Gly
                        260             265             270

Glu Arg Thr Cys Pro Ser Trp Val Val Leu Tyr Arg Lys Asn Arg
                    275             280             285

Ser Leu Ala Ala Pro Arg Gly Pro Gly Leu Val Lys Ala Pro Val Trp
                    290             295             300

Trp Pro Met Lys Asp Asn Pro Gly Thr Thr Ala Ser Thr Ala Lys
            305             310             315             320

Asn Ala Pro

<210> SEQ ID NO 4
<211> LENGTH: 13
<212> TYPE: PRT
<213> ORGANISM: homo sapiens
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(9)
<223> OTHER INFORMATION: Xaa can be any naturally occurring amino acid

<400> SEQUENCE: 4

Val Ala Lys Lys Cys Xaa Gly Xaa Xaa Asn Pro Ile Thr
1               5                   10
```

<210> SEQ ID NO 5
<211> LENGTH: 2398
<212> TYPE: DNA
<213> ORGANISM: homo sapiens
<220> FEATURE:
<221> NAME/KEY: misc_feature
<222> LOCATION: (880)..(880)
<223> OTHER INFORMATION: n is a nucleotide that results in C224W
      mutation associated with X-linked muscular myopathy

<400> SEQUENCE: 5

| | | | | | |
|---|---|---|---|---|---|
| cggagggggc | tcagtccgca | gccgccgccg | ccaccgccgc | gcctcggcct | cggtgcaggc | 60 |
| agcggccgcc | gccgccgaga | cagctgcgcg | ggcgagcatc | cccacgcagc | accttggaag | 120 |
| ttgttttcaa | ccatatccag | cctttgccga | atacatccta | tctgccacac | atccagcgtg | 180 |
| aggtccctcc | agctacaagg | tgggcaccat | ggcggagaag | tttgactgcc | actactgcag | 240 |
| ggatcccttg | caggggaaga | agtatgtgca | aaggatggc | caccactgct | gcctgaaatg | 300 |
| ctttgacaag | ttctgtgcca | acacctgtgt | ggaatgccgc | aagcccatcg | gtgcggactc | 360 |
| caaggaggtg | cactataaga | accgcttctg | gcatgacacc | tgcttccgct | gtgccaagtg | 420 |
| ccttcacccc | ttggccaatg | agaccttttg | ggccaaggac | aacaagatcc | tgtgcaacaa | 480 |
| gtgcaccact | cgggaggact | cccccaagtg | caaggggtgc | ttcaaggcca | ttgtggcagg | 540 |
| agatcaaaac | gtggagtaca | aggggaccgt | ctggcacaaa | gactgcttca | cctgtagtaa | 600 |
| ctgcaagcaa | gtcatcggga | ctggaagctt | cttccctaaa | ggggaggact | tctactgcgt | 660 |
| gacttgccat | gagaccaagt | tgccaagca | ttgcgtgaag | tgcaacaagg | ccatcacatc | 720 |
| tggaggaatc | acttaccagg | atcagccctg | gcatgccgat | tgctttgtgt | gtgttacctg | 780 |
| ctctaagaag | ctggctgggc | agcgtttcac | cgctgtggag | gaccagtatt | actgcgtgga | 840 |
| ttgctacaag | aactttgtgg | ccaagaagtg | tgctggatgn | aagaaccccca | tcactgggtt | 900 |
| tggtaaaggc | tccagtgtgg | tggcctatga | aggacaatcc | tggcacgact | actgcttcca | 960 |
| ctgcaaaaaa | tgctccgtga | atctggccaa | caagcgcttt | gttttccacc | aggagcaagt | 1020 |
| gtattgtccc | gactgtgcca | aaagctgta | aactgacagg | ggctcctgtc | ctgtaaaatg | 1080 |
| gcatttgaat | ctcgttcttt | gtgtccttac | tttctgccct | ataccatcaa | taggggaaga | 1140 |
| gtggtccttc | ccttctttaa | agttctcctt | ccgtctttc | tcccattta | cagtattact | 1200 |
| caaataaggg | cacacagtga | tcatattagc | atttagcaaa | aagcaaccct | gcagcaaagt | 1260 |
| gaatttctgt | ccggctgcaa | tttaaaaatg | aaaacttagg | tagattgact | cttctgcatg | 1320 |
| tttctcatag | agcagaaaag | tgctaatcat | ttagccactt | agtgatgtaa | gcaagaagca | 1380 |
| taggagataa | aaccccccact | gagatgcctc | tcatgcctca | gctgggaccc | accgtgtaga | 1440 |
| cacacgacat | gcaagagttg | cagcggctgc | tccaactcac | tgctcaccct | cttctgtgag | 1500 |
| caggaaaaga | accctactga | catgcatggt | ttaacttcct | catcagaact | ctgcccttcc | 1560 |
| ttctgttctt | ttgtgctttc | aaataactaa | cacgaacttc | cagaaaatta | acatttgaac | 1620 |
| ttagctgtaa | ttctaaactg | acctttcccc | gtactaacgt | ttggtttccc | cgtgtggcat | 1680 |
| gttttctgag | cgttcctact | ttaaagcatg | aacatgcag | gtgatttggg | aagtgtagaa | 1740 |
| agacctgaga | aaacgagcct | gtttcagagg | aacatcgtca | caacgaatac | ttctggaagc | 1800 |
| ttaacaaaac | taaccctgct | gtccttttta | ttgtttttaa | ttaatatttt | tgttttaatt | 1860 |
| gatagcaaaa | tagtttatgg | gtttggaaac | ttgcatgaaa | atattttagc | cccctcagat | 1920 |
| gttcctgcag | tgctgaaatt | catcctacgg | aagtaaccgc | aaaactctag | aggggagtt | 1980 |

```
gagcaggcgc cagggctgtc atcaacatgg atatgacatt tcacaacagt gactagttga    2040
atcccttgta acgtagtagt tgtctgctct ttgtccatgt gttaatgagg actgcaaagt    2100
cccttctgtt gtgattccta ggacttttcc tcaagaggaa atctggattt ccacctaccg    2160
cttacctgaa atgcaggatc acctacttac tgtattctac attattatat gacatagtat    2220
aatgagacaa tatcaaaagt aaacatgtaa tgacaataca tactaacatt cttgtaggag    2280
tggttagaga agctgatgcc tcatttctac attctgtcat tagctattat catctaacgt    2340
ttcagtgtat ccttacagaa ataaagcagc atatgaaaaa aaaaaaaaaa aaaaaaa       2398
```

<210> SEQ ID NO 6
<211> LENGTH: 1096
<212> TYPE: DNA
<213> ORGANISM: homo sapiens
<220> FEATURE:
<221> NAME/KEY: misc_feature
<222> LOCATION: (725)..(725)
<223> OTHER INFORMATION: n is a nucleotide that results in C224W
      mutation associated with X-linked muscular myopathy

<400> SEQUENCE: 6

```
tcctatctgc cacacatcca gcgtgaggtc cctccagcta caaggtgggc accatggcgg      60
agaagtttga ctgccactac tgcagggatc ccttgcaggg aagaagtat gtgcaaaagg     120 atggccacca ctgctgcctg aaatgctttg acaagttctg tgccaacacc tgtgtggaat    180
gccgcaagcc catcggtgcg gactccaagg aggtgcacta aagaaccgc ttctggcatg     240 acacctgctt ccgctgtgcc aagtgccttc accccttggc caatgagacc tttgtggcca    300
aggacaacaa gatcctgtgc aacaagtgca ccactcggga ggactccccc aagtgcaagg    360
ggtgcttcaa ggccattgtg gcaggagatc aaaacgtgga gtacaagggg accgtctggc    420
acaaagactg cttcacctgt agtaactgca agcaagtcat cgggactgga agcttcttcc    480
ctaaagggga ggacttctac tgcgtgactt gccatgagac caagtttgcc aagcattgcg    540
tgaagtgcaa caaggccatc acatctggag gaatcactta ccaggatcag ccctggcatg    600
ccgattgctt tgtgtgtgtt acctgctcta agaagctggc tgggcagcgt ttcaccgctg    660
tggaggacca gtattactgc gtggattgct acaagaactt tgtggccaag aagtgtgctg    720
gatgnaagaa ccccatcact gggaaaagga ctgtgtcaag agtgagccgc ccagtctcta    780
aagctaggaa gccccagtg tgccacggga acgcttgcc tctcaccctg tttcccagcg      840
ccaacctccg gggcaggcat ccgggtggag agaggacttg tccctcgtgg gtggtggttc    900
tttatagaaa aaatcgaagc ttagcagctc ctcgtggccc gggtttggta aaggctccag    960
tgtggtggcc tatgaaggac aatcctggca cgactactgc ttccactgca aaaaatgctc   1020
cgtgaatctg gccaacaagc gctttgtttt ccaccaggag caagtgtatt gtcccgactg   1080
tgccaaaaag ctgtaa                                                   1096
```

<210> SEQ ID NO 7
<211> LENGTH: 2398
<212> TYPE: DNA
<213> ORGANISM: homo sapiens

<400> SEQUENCE: 7

```
cggagggggc tcagtccgca gccgccgccg ccaccgccgc gcctcggcct cggtgcaggc     60
agcggccgcc gccgccgaga cagctgcgcg ggcgagcatc cccacgcagc accttggaag    120
ttgttttcaa ccatatccag cctttgccga atacatccta tctgccacac atccagcgtg    180
```

```
aggtccctcc agctacaagg tgggcaccat ggcggagaag tttgactgcc actactgcag    240
ggatcccttg caggggaaga agtatgtgca aaaggatggc caccactgct gcctgaaatg    300
ctttgacaag ttctgtgcca acacctgtgt ggaatgccgc aagcccatcg gtgcggactc    360
caaggaggtg cactataaga accgcttctg gcatgacacc tgcttccgct gtgccaagtg    420
ccttcacccc ttggccaatg agacctttgt ggccaaggac aacaagatcc tgtgcaacaa    480
gtgcaccact cgggaggact cccccaagtg caaggggtgc ttcaaggcca ttgtggcagg    540
agatcaaaac gtggagtaca aggggaccgt ctggcacaaa gactgcttca cctgtagtaa    600
ctgcaagcaa gtcatcggga ctggaagctt cttccctaaa ggggaggact ctactgcgt    660 gacttgccat gagaccaagt tgccaagca ttgcgtgaag tgcaacaagg ccatcacatc    720
tggaggaatc acttaccagg atcagccctg gcatgccgat tgctttgtgt gtgttacctg    780
ctctaagaag ctggctgggc agcgtttcac cgctgtggag gaccagtatt actgcgtgga    840
ttgctacaag aactttgtgg ccaagaagtg tgctggatgc aagaaccca tcactgggtt    900 tggtaaaggc tccagtgtgg tggcctatga aggacaatcc tggcacgact actgcttcca    960
ctgcaaaaaa tgctccgtga atctggccaa caagcgcttt gttttccacc aggagcaagt   1020
gtattgtccc gactgtgcca aaaagctgta aactgacagg ggctcctgtc ctgtaaaatg   1080
gcatttgaat ctcgttcttt gtgtccttac tttctgccct ataccatcaa taggggaaga   1140
gtggtccttc ccttctttaa agttctcctt ccgtcttttc tcccatttta cagtattact   1200
caaataaggg cacacagtga tcatattagc atttagcaaa aagcaaccct gcagcaaagt   1260
gaatttctgt ccggctgcaa tttaaaaatg aaaacttagg tagattgact cttctgcatg   1320
tttctcatag agcagaaaag tgctaatcat ttagccactt agtgatgtaa gcaagaagca   1380
taggagataa aaccccacct gagatgcctc tcatgcctca gctgggaccc accgtgtaga   1440
cacacgacat gcaagagttg cagcggctgc tccaactcac tgctcaccct cttctgtgag   1500
caggaaaaga accctactga catgcatggt ttaacttcct catcagaact ctgcccttcc   1560
ttctgttctt ttgtgctttc aaataactaa cacgaacttc cagaaaatta acatttgaac   1620
ttagctgtaa ttctaaactg acctttcccc gtactaacgt ttggtttccc cgtgtggcat   1680
gttttctgag cgttcctact ttaaagcatg aacatgcag gtgatttggg aagtgtagaa   1740
agacctgaga aaacgagcct gtttcagagg aacatcgtca caacgaatac ttctggaagc   1800
ttaacaaaac taaccctgct gtccttttta ttgtttttaa ttaatatttt tgtttttaatt   1860 gatagcaaaa tagtttatgg gtttggaaac ttgcatgaaa atattttagc cccctcagat   1920
gttcctgcag tgctgaaatt catcctacgg aagtaaccgc aaaactctag agggggagtt   1980
gagcaggcgc cagggctgtc atcaacatgg atatgacatt tcacaacagt gactagttga   2040
atcccttgta acgtagtagt tgtctgctct ttgtccatgt gttaatgagg actgcaaagt   2100
cccttctgtt gtgattccta ggacttttcc tcaagaggaa atctggattt ccacctaccg   2160
cttacctgaa atgcaggatc acctacttac tgtattctac attattatat gacatagtat   2220
aatgagacaa tatcaaaagt aaacatgtaa tgacaataca tactaacatt cttgtaggag   2280
tggttagaga agctgatgcc tcatttctac attctgtcat tagctattat catctaacgt   2340
ttcagtgtat ccttacagaa ataaagcagc atatgaaaaa aaaaaaaaaa aaaaaaa      2398

<210> SEQ ID NO 8
<211> LENGTH: 280
<212> TYPE: PRT
```

<213> ORGANISM: homo sapiens

<400> SEQUENCE: 8

```
Met Ala Glu Lys Phe Asp Cys His Tyr Cys Arg Asp Pro Leu Gln Gly
1               5                   10                  15
Lys Lys Tyr Val Gln Lys Asp Gly His His Cys Cys Leu Lys Cys Phe
            20                  25                  30
Asp Lys Phe Cys Ala Asn Thr Cys Val Glu Cys Arg Lys Pro Ile Gly
        35                  40                  45
Ala Asp Ser Lys Glu Val His Tyr Lys Asn Arg Phe Trp His Asp Thr
    50                  55                  60
Cys Phe Arg Cys Ala Lys Cys Leu His Pro Leu Ala Asn Glu Thr Phe
65                  70                  75                  80
Val Ala Lys Asp Asn Lys Ile Leu Cys Asn Lys Cys Thr Thr Arg Glu
                85                  90                  95
Asp Ser Pro Lys Cys Lys Gly Cys Phe Lys Ala Ile Val Ala Gly Asp
            100                 105                 110
Gln Asn Val Glu Tyr Lys Gly Thr Val Trp His Lys Asp Cys Phe Thr
        115                 120                 125
Cys Ser Asn Cys Lys Gln Val Ile Gly Thr Gly Ser Phe Phe Pro Lys
    130                 135                 140
Gly Glu Asp Phe Tyr Cys Val Thr Cys His Glu Thr Lys Phe Ala Lys
145                 150                 155                 160
His Cys Val Lys Cys Asn Lys Ala Ile Thr Ser Gly Gly Ile Thr Tyr
                165                 170                 175
Gln Asp Gln Pro Trp His Ala Asp Cys Phe Val Cys Val Thr Cys Ser
            180                 185                 190
Lys Lys Leu Ala Gly Gln Arg Phe Thr Ala Val Glu Asp Gln Tyr Tyr
        195                 200                 205
Cys Val Asp Cys Tyr Lys Asn Phe Val Ala Lys Lys Cys Ala Gly Cys
    210                 215                 220
Lys Asn Pro Ile Thr Gly Phe Gly Lys Gly Ser Ser Val Val Ala Tyr
225                 230                 235                 240
Glu Gly Gln Ser Trp His Asp Tyr Cys Phe His Cys Lys Lys Cys Ser
                245                 250                 255
Val Asn Leu Ala Asn Lys Arg Phe Val Phe His Gln Glu Gln Val Tyr
            260                 265                 270
Cys Pro Asp Cys Ala Lys Lys Leu
        275                 280
```

<210> SEQ ID NO 9
<211> LENGTH: 1096
<212> TYPE: DNA
<213> ORGANISM: homo sapiens

<400> SEQUENCE: 9

```
tcctatctgc cacacatcca gcgtgaggtc cctccagcta caaggtgggc accatggcgg    60
agaagtttga ctgccactac tgcagggatc ccttgcaggg aagaagtat gtgcaaaagg   120 atggccacca ctgctgcctg aaatgctttg acaagttctg tgccaacacc tgtgtggaat   180
gccgcaagcc catcggtgcg gactccaagg aggtgcacta taagaaccgc ttctggcatg   240
acacctgctt ccgctgtgcc aagtgccttc accccttggc caatgagacc tttgtggcca   300
aggacaacaa gatcctgtgc aacaagtgca ccactcggga ggactccccc aagtgcaagg   360
ggtgcttcaa ggccattgtg gcaggagatc aaaacgtgga gtacaagggg accgtctggc   420
```

-continued

```
acaaagactg cttcacctgt agtaactgca agcaagtcat cgggactgga agcttcttcc    480
ctaaagggga ggacttctac tgcgtgactt gccatgagac caagtttgcc aagcattgcg    540
tgaagtgcaa caaggccatc acatctggag gaatcactta ccaggatcag ccctggcatg    600
ccgattgctt tgtgtgtgtt acctgctcta agaagctggc tgggcagcgt ttcaccgctg    660
tggaggacca gtattactgc gtggattgct acaagaactt tgtggccaag aagtgtgctg    720
gatgcaagaa ccccatcact gggaaaagga ctgtgtcaag agtgagccgc ccagtctcta    780
aagctaggaa gccccccagtg tgccacggga acgcttgcc tctcaccctg tttcccagcg    840
ccaacctccg gggcaggcat ccgggtggag agaggacttg tccctcgtgg gtggtggttc    900
tttatagaaa aaatcgaagc ttagcagctc ctcgtggccc gggtttggta aaggctccag    960
tgtggtggcc tatgaaggac aatcctggca cgactactgc ttccactgca aaaaatgctc   1020
cgtgaatctg ccaacaagc gctttgtttt ccaccaggag caagtgtatt gtcccgactg    1080
tgccaaaaag ctgtaa                                                    1096
```

<210> SEQ ID NO 10
<211> LENGTH: 323
<212> TYPE: PRT
<213> ORGANISM: homo sapiens

<400> SEQUENCE: 10

```
Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
            20                  25                  30

Asp Lys Phe Cys Ala Asn Thr Cys Val Glu Cys Arg Lys Pro Ile Gly
        35                  40                  45

Ala Asp Ser Lys Glu Val His Tyr Lys Asn Arg Phe Trp His Asp Thr
    50                  55                  60

Cys Phe Arg Cys Ala Lys Cys Leu His Pro Leu Ala Asn Glu Thr Phe
65                  70                  75                  80

Val Ala Lys Asp Asn Lys Ile Leu Cys Asn Lys Cys Thr Thr Arg Glu
                85                  90                  95

Asp Ser Pro Lys Cys Lys Gly Cys Phe Lys Ala Ile Val Ala Gly Asp
            100                 105                 110

Gln Asn Val Glu Tyr Lys Gly Thr Val Trp His Lys Asp Cys Phe Thr
        115                 120                 125

Cys Ser Asn Cys Lys Gln Val Ile Gly Thr Gly Ser Phe Phe Pro Lys
    130                 135                 140

Gly Glu Asp Phe Tyr Cys Val Thr Cys His Glu Thr Lys Phe Ala Lys
145                 150                 155                 160

His Cys Val Lys Cys Asn Lys Ala Ile Thr Ser Gly Gly Ile Thr Tyr
                165                 170                 175

Gln Asp Gln Pro Trp His Ala Asp Cys Phe Val Cys Val Thr Cys Ser
            180                 185                 190

Lys Lys Leu Ala Gly Gln Arg Phe Thr Ala Val Glu Asp Gln Tyr Tyr
        195                 200                 205

Cys Val Asp Cys Tyr Lys Asn Phe Val Ala Lys Cys Ala Gly Cys
    210                 215                 220

Lys Asn Pro Ile Thr Gly Lys Arg Thr Val Ser Arg Val Ser Arg Pro
225                 230                 235                 240

Val Ser Lys Ala Arg Lys Pro Pro Val Cys His Gly Lys Arg Leu Pro
```

```
                    245                 250                 255
Leu Thr Leu Phe Pro Ser Ala Asn Leu Arg Gly Arg His Pro Gly Gly
            260                 265                 270

Glu Arg Thr Cys Pro Ser Trp Val Val Leu Tyr Arg Lys Asn Arg
            275                 280                 285

Ser Leu Ala Ala Pro Arg Gly Pro Gly Leu Val Lys Ala Pro Val Trp
            290                 295                 300

Trp Pro Met Lys Asp Asn Pro Gly Thr Thr Thr Ala Ser Thr Ala Lys
305                 310                 315                 320

Asn Ala Pro
```

<210> SEQ ID NO 11
<211> LENGTH: 585
<212> TYPE: DNA
<213> ORGANISM: homo sapiens

<400> SEQUENCE: 11

```
atggcggaga agtttgactg ccactactgc agggatccct tgcagggaa gaagtatgtg      60
caaaaggatg gccaccactg ctgcctgaaa tgctttgaca gttctgtgc caacacctgt     120
gtggaatgcc gcaagcccat cggtgcggac tccaaggagg tgcactataa gaaccgcttc     180
tggcatgaca cctgcttccg ctgtgccaag tgccttcacc ccttggccaa tgagaccttt     240
gtggccaagg acaacaagat cctgtgcaac aagtgcacca ctcgggagga ctcccccaag     300
tgcaaggggt gcttcaaggc cattgtggca ggagatcaaa acgtggagta caaggggacc     360
gtctggcaca agactgcttt cacctgtagt aactgcaagc aagtcatcgg gactggaagc     420
ttcttcccta aggggagga cttctactgc gtgacttgcc atgagaccaa gtttgccaag     480
cattgcgtga agtgcaacaa gggtttggta aaggctccag tgtggtggcc tatgaaggac     540
aatcctggca cgactactgc ttccactgca aaaaatgctc cgtga                    585
```

<210> SEQ ID NO 12
<211> LENGTH: 194
<212> TYPE: PRT
<213> ORGANISM: homo sapiens

<400> SEQUENCE: 12

```
Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
            20                  25                  30

Asp Lys Phe Cys Ala Asn Thr Cys Val Glu Cys Arg Lys Pro Ile Gly
            35                  40                  45

Ala Asp Ser Lys Glu Val His Tyr Lys Asn Arg Phe Trp His Asp Thr
50                  55                  60

Cys Phe Arg Cys Ala Lys Cys Leu His Pro Leu Ala Asn Glu Thr Phe
65                  70                  75                  80

Val Ala Lys Asp Asn Lys Ile Leu Cys Asn Lys Cys Thr Thr Arg Glu
                85                  90                  95

Asp Ser Pro Lys Cys Lys Gly Cys Phe Lys Ala Ile Val Ala Gly Asp
            100                 105                 110

Gln Asn Val Glu Tyr Lys Gly Thr Val Trp His Lys Asp Cys Phe Thr
            115                 120                 125

Cys Ser Asn Cys Lys Gln Val Ile Gly Thr Gly Ser Phe Phe Pro Lys
        130                 135                 140
```

```
Gly Glu Asp Phe Tyr Cys Val Thr Cys His Glu Thr Lys Phe Ala Lys
145                 150                 155                 160

His Cys Val Lys Cys Asn Lys Gly Leu Val Lys Ala Pro Val Trp Trp
                165                 170                 175

Pro Met Lys Asp Asn Pro Gly Thr Thr Thr Ala Ser Thr Ala Lys Asn
            180                 185                 190

Ala Pro

<210> SEQ ID NO 13
<211> LENGTH: 1997
<212> TYPE: DNA
<213> ORGANISM: homo sapiens

<400> SEQUENCE: 13
```

| | | | | | |
|---|---|---|---|---|---|
| agtccgcagc | cgccgccgcc | accgccgcgc | ctcggcctcg | gtgcaggcag | cggctgccgc | 60 |
| cgccgagaca | gctgcgcggg | cgagcatccc | cacgcagcac | cttggaagtt | gttttcaacc | 120 |
| atatccagcc | tttgccgaat | acatcctatc | tgccacacat | ccagcgtgag | gtccctccag | 180 |
| ctacaaggtg | ggcaccatgg | cggagaagtt | tgactgccac | tactgcaggg | atcccttgca | 240 |
| ggggaagaag | tatgtgcaaa | aggatggcca | ccactgctgc | ctgaaatgct | ttgacaagtt | 300 |
| tgccaagcat | tgcgtgaagt | gcaacaaggc | catcacatct | ggaggaatca | cttaccagga | 360 |
| tcagccctgg | catgccgatt | gctttgtgtg | tgttacctgc | tctaagaagc | tggctgggca | 420 |
| gcgtttcacc | gctgtggagg | accagtatta | ctgcgtggat | tgctacaaga | actttgtggc | 480 |
| caagaagtgt | gctggatgca | gaacccccat | cactgggttt | ggtaaaggct | ccagtgtggt | 540 |
| ggcctatgaa | ggacaatcct | ggcacgacta | ctgcttccac | tgcaaaaaat | gctccgtgaa | 600 |
| tctggccaac | aagcgctttg | ttttccacca | ggagcaagtg | tattgtcccg | actgtgccaa | 660 |
| aaagctgtaa | actgacaggg | gctcctgtcc | tgtaaaatgg | catttgaatc | tcgttctttg | 720 |
| tgtccttact | ttctgcccta | taccatcaat | aggggaagag | tggtccttcc | cttctttaaa | 780 |
| gttctccttc | cgtctttctt | cccatttttac | agtattactc | aaataagggc | acacagtgat | 840 |
| catattagca | tttagcaaaa | agcaaccctg | cagcaaagtg | aatttctgtc | cggctgcaat | 900 |
| ttaaaaatga | aaacttaggt | agattgactc | ttctgcatgt | ttctcataga | gcagaaaagt | 960 |
| gctaatcatt | tagccactta | gtgatgtaag | caagaagcat | aggagataaa | accccactg | 1020 |
| agatgcctct | catgcctcag | ctgggaccca | ccgtgtagac | acgacatg | caagagttgc | 1080 |
| agcggctgct | ccaactcact | gctcaccctc | ttctgtgagc | aggaaaagaa | ccctactgac | 1140 |
| atgcatggtt | taacttcctc | atcagaactc | tgcccttcct | tctgttcttt | tgtgctttca | 1200 |
| aataactaac | acgaacttcc | agaaaattaa | catttgaact | tagctgtaat | tctaaactga | 1260 |
| cctttccccg | tactaacgtt | tggtttcccc | gtgtggcatg | ttttctgagc | gttcctactt | 1320 |
| taaagcatgg | aacatgcagg | tgatttggga | agtgtagaaa | gacctgagaa | aacgagcctg | 1380 |
| tttcagagga | acatcgtcac | aacgaatact | tctggaagct | taacaaaact | aaccctgctg | 1440 |
| tccttttttat | tgttttttaat | taatattttt | gttttaattg | atagcaaaat | agtttatggg | 1500 |
| tttggaaact | tgcatgaaaa | tattttagcc | ccctcagatg | ttcctgcagt | gctgaaattc | 1560 |
| atcctacaga | agtaaccgca | aaactctaga | ggggagttga | agcaggcgcc | agggctgtca | 1620 |
| tcaacatgga | tatgacattt | cacaacagtg | actagttgaa | tcccttgtaa | cgtagtagtt | 1680 |
| gtctgctctt | tgtccatgtg | ttaatgagga | ctgcaaagtc | ccttctgttg | tgattcctag | 1740 |
| gacttttcct | caagaggaaa | tctggatttc | cacctaccgc | ttacctgaaa | tgcaggatca | 1800 |

```
cctacttact gtattctaca ttattatatg acatagtata atgagacaat atcaaaagta    1860
aacatgtaat gacaatacat actaacattc ttgtaggagt ggttagagaa gctgatgcct    1920
catttctaca ttctgtcatt agctattatc atctaacgtt tcagtgtatc cttacagaaa    1980
taaagcagca tatgaat                                                   1997
```

<210> SEQ ID NO 14
<211> LENGTH: 157
<212> TYPE: PRT
<213> ORGANISM: homo sapiens

<400> SEQUENCE: 14

```
Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
            20                  25                  30

Asp Lys Phe Ala Lys His Cys Val Lys Cys Asn Lys Ala Ile Thr Ser
        35                  40                  45

Gly Gly Ile Thr Tyr Gln Asp Gln Pro Trp His Ala Asp Cys Phe Val
    50                  55                  60

Cys Val Thr Cys Ser Lys Lys Leu Ala Gly Gln Arg Phe Thr Ala Val
65                  70                  75                  80

Glu Asp Gln Tyr Tyr Cys Val Asp Cys Tyr Lys Asn Phe Val Ala Lys
                85                  90                  95

Lys Cys Ala Gly Cys Lys Asn Pro Ile Thr Gly Phe Gly Lys Gly Ser
            100                 105                 110

Ser Val Val Ala Tyr Glu Gly Gln Ser Trp His Asp Tyr Cys Phe His
        115                 120                 125

Cys Lys Lys Cys Ser Val Asn Leu Ala Asn Lys Arg Phe Val Phe His
    130                 135                 140

Gln Glu Gln Val Tyr Cys Pro Asp Cys Ala Lys Lys Leu
145                 150                 155
```

<210> SEQ ID NO 15
<211> LENGTH: 1997
<212> TYPE: DNA
<213> ORGANISM: homo sapiens

<400> SEQUENCE: 15

```
agtccgcagc cgccgccgcc accgccgcgc tcggcctcg gtgcaggcag cggctgccgc     60
cgccgagaca gctgcgcggg cgagcatccc cacgcagcac cttggaagtt gttttcaacc   120
atatccagcc tttgccgaat acatcctatc tgccacacat ccagcgtgag gtccctccag   180
ctacaaggtg ggcaccatgg cggagaagtt tgactgccac tactgcaggg atcccttgca   240
ggggaagaag tatgtgcaaa aggatggcca ccactgctgc ctgaaatgct ttgacaagtt   300
tgccaagcat tgcgtgaagt gcaacaaggc catcacatct ggaggaatca cttaccagga   360
tcagccctgg catgccgatt gctttgtgtg tgttacctgc tctaagaagc tggctgggca   420
gcgtttcacc gctgtggagg accagtatta ctgcgtggat tgctacaaga actttgtggc   480
caagaagtgt gctggatgca agaaccccat cactgggttt ggtaaaggct ccagtgtggt   540
ggcctatgaa ggacaatcct ggcacgacta ctgcttccac tgcaaaaaat gctccgtgaa   600
tctggccaac aagcgctttg ttttccacca ggagcaagtg tattgtcccg actgtgccaa   660
aaagctgtaa actgacaggg gctcctgtcc tgtaaaatgg catttgaatc tcgttctttg   720
tgtccttact ttctgcccta taccatcaat aggggaagag tggtccttcc cttctttaaa   780
```

```
gttctccttc cgtctttttct cccattttac agtattactc aaataagggc acacagtgat    840
catattagca tttagcaaaa agcaaccctg cagcaaagtg aatttctgtc cggctgcaat    900
ttaaaaatga aaacttaggt agattgactc ttctgcatgt ttctcataga gcagaaaagt    960
gctaatcatt tagccactta gtgatgtaag caagaagcat aggagataaa accccccactg   1020 agatgcctct catgcctcag ctgggaccca ccgtgtagac acacgacatg caagagttgc   1080
agcggctgct ccaactcact gctcaccctc ttctgtgagc aggaaaagaa ccctactgac   1140
atgcatggtt taacttcctc atcagaactc tgcccttcct tctgttcttt tgtgctttca   1200
aataactaac acgaacttcc agaaaattaa catttgaact tagctgtaat tctaaactga   1260 cctttcccccg tactaacgtt tggtttcccc gtgtggcatg ttttctgagc gttcctactt   1320
taaagcatgg aacatgcagg tgatttggga agtgtagaaa gacctgagaa acgagcctg    1380 tttcagagga acatcgtcac aacgaatact tctggaagct taacaaaact aaccctgctg   1440 tccttttttat tgtttttaat taatattttt gttttaattg atagcaaaat agtttatggg   1500
tttggaaact tgcatgaaaa tatttttagcc ccctcagatg ttcctgcagt gctgaaattc   1560
atcctacaga agtaaccgca aaactctaga ggggagttg agcaggcgcc agggctgtca   1620
tcaacatgga tatgacattt cacaacagtg actagttgaa tcccttgtaa cgtagtagtt   1680
gtctgctctt tgtccatgtg ttaatgagga ctgcaaagtc ccttctgttg tgattcctag   1740 gactttttcct caagaggaaa tctggatttc cacctaccgc ttacctgaaa tgcaggatca   1800
cctacttact gtattctaca ttattatatg acatagtata atgagacaat atcaaaagta   1860
aacatgtaat gacaatacat actaacattc ttgtaggagt ggttagagaa gctgatgcct   1920
catttctaca ttctgtcatt agctattatc atctaacgtt tcagtgtatc cttacagaaa   1980
taaagcagca tatgaat                                                    1997

<210> SEQ ID NO 16
<211> LENGTH: 157
<212> TYPE: PRT
<213> ORGANISM: homo sapiens

<400> SEQUENCE: 16

Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
            20                  25                  30

Asp Lys Phe Ala Lys His Cys Val Lys Cys Asn Lys Ala Ile Thr Ser
        35                  40                  45

Gly Gly Ile Thr Tyr Gln Asp Gln Pro Trp His Ala Asp Cys Phe Val
    50                  55                  60

Cys Val Thr Cys Ser Lys Lys Leu Ala Gly Gln Arg Phe Thr Ala Val
65                  70                  75                  80

Glu Asp Gln Tyr Tyr Cys Val Asp Cys Tyr Lys Asn Phe Val Ala Lys
                85                  90                  95

Lys Cys Ala Gly Cys Lys Asn Pro Ile Thr Gly Phe Gly Lys Gly Ser
            100                 105                 110

Ser Val Val Ala Tyr Glu Gly Gln Ser Trp His Asp Tyr Cys Phe His
        115                 120                 125

Cys Lys Lys Cys Ser Val Asn Leu Ala Asn Lys Arg Phe Val Phe His
    130                 135                 140

Gln Glu Gln Val Tyr Cys Pro Asp Cys Ala Lys Lys Leu
145                 150                 155
```

<210> SEQ ID NO 17
<211> LENGTH: 2356
<212> TYPE: DNA
<213> ORGANISM: mus musculus

<400> SEQUENCE: 17

| | | | | | |
|---|---|---|---|---|---|
| agtcctgtgc | tgccgctgtc | gccgctgcgc | tttggtctcg | gagctggcag | cggccgccgg | 60 |
| tgccgcctag | acagctgcgc | gggcaactgg | tagctgttct | tagctgtgcc | cagtccttct | 120 |
| ggaacacatc | ctgtgtgagg | tccctccagc | tataaggtgg | gcaccatgtc | ggagaagttc | 180 |
| gactgtcact | actgcaggga | ccccttgcag | gggaagaagt | acgtgcagaa | ggatggccgt | 240 |
| cactgctgcc | tgaagtgctt | tgacaagttc | tgcgccaaca | cctgcgtgga | ctgccgcaag | 300 |
| cccataagcg | ctgatgccaa | ggaggtgcat | ataagaatc | gctactggca | cgacaactgc | 360 |
| ttccgctgtg | ccaagtgcct | tcacccccttg | gccagtgaga | cctttgtgtc | caaggatggc | 420 |
| aagatcctgt | gcaacaagtg | cgctactcgg | gaggactccc | ccaggtgcaa | aggtgcttc | 480 |
| aaggccattg | tggcaggaga | ccagaacgtg | gagtacaagg | gcaccgtctg | cataaagac | 540 |
| tgcttcacct | gcagcaactg | caagcaagtc | attgggaccg | gaagcttctt | cccgaaaggg | 600 |
| gaggacttct | actgtgtgac | ttgccatgag | accaagttcg | ccaaacattg | cgtgaagtgc | 660 |
| aacaaggcca | tcacatctgg | aggaatcact | taccaggatc | agccctggca | tgccgagtgc | 720 |
| tttgtgtgtg | ttacctgctc | taagaagctg | gctgggcagc | gtttcaccgc | tgtggaggac | 780 |
| cagtattact | gcgtggattg | ctacaagaac | tttgtggcca | agaagtgtgc | tggatgcaag | 840 |
| aaccccatca | ctgggtttgg | taaaggctcc | agtgtggtgg | cctatgaagg | acaatcctgg | 900 |
| cacgactact | gcttccactg | caaaaatgc | tccgtgaatc | tggccaacaa | gcgctttgta | 960 |
| tttcataatg | agcaggtgta | ttgccctgac | tgtgccaaaa | agctgtaact | tgacaggggc | 1020 |
| tcctgtcctg | taaaatggca | ttggaaccat | tcttttgtgtc | ctttgctccc | tccctccctc | 1080 |
| tgtaccatcc | atagggcaag | agtgggcttt | cacctctta | aagttgctct | ttccgtcttt | 1140 |
| tctcccattt | tacagtatta | atcaacgaag | gacacacagt | gatcatatta | agatttagca | 1200 |
| aagagcaacc | ttgcagcaaa | aataatttct | ctgttgctgc | actggaaaaa | caaaaccta | 1260 |
| gactgactct | tctgcatgtt | tctcatagag | cagaaaagtg | ctaaccatgt | agccacttca | 1320 |
| cgatgtaaac | gagaagcata | ggcgataaag | ctcccactga | gacacctttg | gggctcagtc | 1380 |
| tggatgcgct | gtgcggtcac | gtgactgcgg | tgtaagagtt | gcagcggctg | ctccaactcc | 1440 |
| cttctcgcct | tctctgggca | gttaagaact | tgccagaatg | catggtttaa | cttccttatc | 1500 |
| aaaactctga | ccttccttct | gttcttttgt | gctttcacac | gactaacaca | gatttccaga | 1560 |
| gaattaacat | tttgaacttt | gttgtaattc | tcaagtgact | ttccccccat | actaacattt | 1620 |
| gactccctta | cgtggcgtgt | tctctgagcg | ttcctacttt | aaagcatgga | acacacaggt | 1680 |
| gatttgaagc | atctaagcag | atctgagaaa | acgagcctgt | tcagaacaa | actcaccaca | 1740 |
| gtgactactt | cggaagctta | acaagactaa | ctctcctgtc | cttttttaatt | tttttttta | 1800 |
| aattttgttt | taatgagtag | taaaatagtt | tatgggtttg | gaaacttgca | tgacaatatt | 1860 |
| tgagcctcct | caaacgttcc | tgcagttttg | agattcatcc | tgtagacatg | acaaaaactc | 1920 |
| tagagccgca | gctgagcagg | cacagggctg | tcatcaaagt | agggacaagg | tgaagtcctt | 1980 |
| gtaacataac | cgttgtctgc | tctttgtctg | catccaggaa | gagtgcaaag | tccctttgct | 2040 |
| tgtgattctt | agaactttcc | ctccagaatt | gcagttagac | tctgggctg | tcggaggtgg | 2100 |

```
tcgtcatcct tcacaggcag gactgggttt tcaccccctt ctctgaaacg caggattgcc    2160
tccttaactg tactctccat tttattacat atataacgag ccaatatcaa agtaaagatg    2220
taatgaaaac acacactcat atattactgt aggagtggtt atagatgcca cacctcatt    2280 tccatatttg tcattagctg tttccatcta ctgtttgatt gtatccttac aaaaataaag    2340
cagcatagaa agagca                                                    2356
```

<210> SEQ ID NO 18
<211> LENGTH: 280
<212> TYPE: PRT
<213> ORGANISM: mus musculus

<400> SEQUENCE: 18

```
Met Ser Glu Lys Phe Asp Cys His Tyr Cys Arg Asp Pro Leu Gln Gly
1               5                   10                  15

Lys Lys Tyr Val Gln Lys Asp Gly Arg His Cys Cys Leu Lys Cys Phe
            20                  25                  30

Asp Lys Phe Cys Ala Asn Thr Cys Val Asp Cys Arg Lys Pro Ile Ser
        35                  40                  45

Ala Asp Ala Lys Glu Val His Tyr Lys Asn Arg Tyr Trp His Asp Asn
    50                  55                  60

Cys Phe Arg Cys Ala Lys Cys Leu His Pro Leu Ala Ser Glu Thr Phe
65                  70                  75                  80

Val Ser Lys Asp Gly Lys Ile Leu Cys Asn Lys Cys Ala Thr Arg Glu
                85                  90                  95

Asp Ser Pro Arg Cys Lys Gly Cys Phe Lys Ala Ile Val Ala Gly Asp
            100                 105                 110

Gln Asn Val Glu Tyr Lys Gly Thr Val Trp His Lys Asp Cys Phe Thr
        115                 120                 125

Cys Ser Asn Cys Lys Gln Val Ile Gly Thr Gly Ser Phe Phe Pro Lys
    130                 135                 140

Gly Glu Asp Phe Tyr Cys Val Thr Cys His Glu Thr Lys Phe Ala Lys
145                 150                 155                 160

His Cys Val Lys Cys Asn Lys Ala Ile Thr Ser Gly Gly Ile Thr Tyr
                165                 170                 175

Gln Asp Gln Pro Trp His Ala Glu Cys Phe Val Cys Val Thr Cys Ser
            180                 185                 190

Lys Lys Leu Ala Gly Gln Arg Phe Thr Ala Val Glu Asp Gln Tyr Tyr
        195                 200                 205

Cys Val Asp Cys Tyr Lys Asn Phe Val Ala Lys Cys Ala Gly Cys
    210                 215                 220

Lys Asn Pro Ile Thr Gly Phe Gly Lys Gly Ser Ser Val Val Ala Tyr
225                 230                 235                 240

Glu Gly Gln Ser Trp His Asp Tyr Cys Phe His Cys Lys Lys Cys Ser
                245                 250                 255

Val Asn Leu Ala Asn Lys Arg Phe Val Phe His Asn Glu Gln Val Tyr
            260                 265                 270

Cys Pro Asp Cys Ala Lys Lys Leu
        275                 280
```

<210> SEQ ID NO 19
<211> LENGTH: 2605
<212> TYPE: DNA
<213> ORGANISM: mus musculus

```
<400> SEQUENCE: 19 ggggagccg cagctcgtgc tccgtggccg ctactccggg gctgcgcgga cctgctgggc         60
ttgggtacct gcggcctccg gcctccgctg cctcgcccac gttggggct gaggaacctg        120 gggctccaag gtcccttagg gcaactggta gctgttctta gctgtgccca gtccttctgg       180
aacacatcct gtgtgaggtc cctccagcta taaggtgggc accatgtcgg agaagttcga       240
ctgtcactac tgcagggacc ccttgcaggg aagaagtac gtgcagaagg atggccgtca        300
ctgctgcctg aagtgctttg acaagttctg cgccaacacc tgcgtggact gccgcaagcc       360
cataagcgct gatgccaagg aggtgcatta taagaatcgc tactggcacg acaactgctt       420
ccgctgtgcc aagtgccttc accccttggc cagtgagacc tttgtgtcca aggatggcaa       480
gatcctgtgc aacaagtgcg ctactcggga ggactccccc aggtgcaaag ggtgcttcaa       540
ggccattgtg gcaggagacc agaacgtgga gtacaagggc accgtctggc ataaagactg       600
cttcacctgc agcaactgca agcaagtcat tgggaccgga agcttcttcc gaaagggga       660 ggacttctac tgtgtgactt gccatgagac caagttcgcc aaacattgcg tgaagtgcaa       720
caaggccatc acatctggag gaatcactta ccaggatcag ccctggcatg ccgagtgctt       780
tgtgtgtgtt acctgctcta agaagctggc tgggcagcgt tcaccgctg tggaggacca       840 gtattactgc gtggattgct acaagaactt tgtggccaag aagtgtgctg atgcaagaa       900 ccccatcact gggaaaagga ctgtgtcaag agtgagccac ccagtctcta agctaggaa       960 gtccccagtg tgccacggga acgcttgcc tctcaccctg tttcccagcg ccaacctccg       1020
gggcaggcat ccgggtggag agaggacttg tccctcgtgg gtggtggttc tttatagaaa      1080
aaatcgaagc ttagcagctc ctcgaggccc gggtttggta aaggctccag tgtggtggcc       1140
tatgaaggac aatcctggca cgactactgc ttccactgca aaaatgctc cgtgaatctg        1200 gccaacaagc gctttgtatt tcataatgag caggtgtatt gccctgactg tgccaaaaag       1260
ctgtaacttg acaggggctc ctgtcctgta aaatggcatt ggaaccattc tttgtgtcct       1320
ttgctccctc cctccctctg taccatccat agggcaagag tgggctttca cctctttaaa       1380
gttgctcttt ccgtcttttc tcccatttta cagtattaat caacgaagga cacacagtga       1440
tcatattaag atttagcaaa gagcaacctt gcagcaaaaa taatttctct gttgctgcac       1500
tggaaaaaca aaaccttaga ctgactcttc tgcatgtttc tcatagagca gaaaagtgct       1560
aaccatgtag ccacttcacg atgtaaacga gaagcatagg cgataaagct cccactgaga       1620
cacctttggg gctcagtctg gatgcgctgt gcggtcacgt gactgcggtg taagagttgc       1680
agcggctgct ccaactccct tctcgccttc tctgggcagt taagaacttg ccagaatgca       1740
tggtttaact tccttatcaa aactctgacc ttccttctgt tcttttgtgc tttcacacga       1800
ctaacacaga tttccagaga attaacattt tgaactttgt tgtaattctc aagtgacttt       1860
tcccccatac taacatttga ctcccttacg tggcgtgttc tctgagcgtt cctactttaa       1920
agcatggaac acacaggtga tttgaagcat ctaagcagat ctgagaaaac gagcctgttt       1980
cagaacaaac tcaccacagt gactacttcg gaagcttaac aagactaact ctcctgtcct      2040
ttttaatttt tttttttaaat tttgttttaa tgagtagtaa aatagtttat gggtttggaa       2100
acttgcatga caatatttga gcctcctcaa acgttcctgc agttttgaga ttcatcctgt       2160
agacatgaca aaaactctag agccgcagct gagcaggcac agggctgtca tcaaagtagg       2220
gacaaggtga agtccttgta acataaccgt tgtctgctct ttgtctgcat ccaggaagag       2280
tgcaaagtcc ctttgcttgt gattcttaga actttccctc cagaattgca gttagactct       2340
```

-continued

```
gggctgtcg gaggtggtcg tcatccttca caggcaggac tgggttttca cccccttctc      2400
tgaaacgcag gattgcctcc ttaactgtac tctccatttt attacatata taacgagcca      2460
atatcaaagt aaagatgtaa tgaaaacaca cactcatata ttactgtagg agtggttata      2520
gatgccaaca cctcatttcc atatttgtca ttagctgttt ccatctactg tttgattgta      2580
tccttacaaa aataaagcag catag                                            2605
```

<210> SEQ ID NO 20
<211> LENGTH: 323
<212> TYPE: PRT
<213> ORGANISM: mus musculus

<400> SEQUENCE: 20

```
Met Ser Glu Lys Phe Asp Cys His Tyr Cys Arg Asp Pro Leu Gln Gly
 1               5                  10                  15

Lys Lys Tyr Val Gln Lys Asp Gly Arg His Cys Cys Leu Lys Cys Phe
            20                  25                  30

Asp Lys Phe Cys Ala Asn Thr Cys Val Asp Cys Arg Lys Pro Ile Ser
        35                  40                  45

Ala Asp Ala Lys Glu Val His Tyr Lys Asn Arg Tyr Trp His Asp Asn
    50                  55                  60

Cys Phe Arg Cys Ala Lys Cys Leu His Pro Leu Ala Ser Glu Thr Phe
65                  70                  75                  80

Val Ser Lys Asp Gly Lys Ile Leu Cys Asn Lys Cys Ala Thr Arg Glu
                85                  90                  95

Asp Ser Pro Arg Cys Lys Gly Cys Phe Lys Ala Ile Val Ala Gly Asp
           100                 105                 110

Gln Asn Val Glu Tyr Lys Gly Thr Val Trp His Lys Asp Cys Phe Thr
       115                 120                 125

Cys Ser Asn Cys Lys Gln Val Ile Gly Thr Gly Ser Phe Phe Pro Lys
   130                 135                 140

Gly Glu Asp Phe Tyr Cys Val Thr Cys His Glu Thr Lys Phe Ala Lys
145                 150                 155                 160

His Cys Val Lys Cys Asn Lys Ala Ile Thr Ser Gly Gly Ile Thr Tyr
                165                 170                 175

Gln Asp Gln Pro Trp His Ala Glu Cys Phe Val Cys Val Thr Cys Ser
           180                 185                 190

Lys Lys Leu Ala Gly Gln Arg Phe Thr Ala Val Glu Asp Gln Tyr Tyr
       195                 200                 205

Cys Val Asp Cys Tyr Lys Asn Phe Val Ala Lys Cys Ala Gly Cys
   210                 215                 220

Lys Asn Pro Ile Thr Gly Lys Arg Thr Val Ser Arg Val Ser His Pro
225                 230                 235                 240

Val Ser Lys Ala Arg Lys Ser Pro Val Cys His Gly Lys Arg Leu Pro
                245                 250                 255

Leu Thr Leu Phe Pro Ser Ala Asn Leu Arg Gly Arg His Pro Gly Gly
           260                 265                 270

Glu Arg Thr Cys Pro Ser Trp Val Val Leu Tyr Arg Lys Asn Arg
       275                 280                 285

Ser Leu Ala Ala Pro Arg Gly Pro Gly Leu Val Lys Ala Pro Val Trp
   290                 295                 300

Trp Pro Met Lys Asp Asn Pro Gly Thr Thr Thr Ala Ser Thr Ala Lys
305                 310                 315                 320
```

Asn Ala Pro

<210> SEQ ID NO 21
<211> LENGTH: 64
<212> TYPE: PRT
<213> ORGANISM: homo sapiens

<400> SEQUENCE: 21

Val Ala Lys Lys Cys Ala Gly Cys Lys Asn Pro Ile Thr Gly Phe Gly
1               5                   10                  15

Lys Gly Ser Ser Val Val Ala Tyr Glu Gly Gln Ser Trp His Asp Tyr
            20                  25                  30

Cys Phe His Cys Lys Lys Cys Ser Val Asn Leu Ala Asn Lys Arg Phe
        35                  40                  45

Val Phe His Gln Glu Gln Val Tyr Cys Pro Asp Cys Ala Lys Lys Leu
    50                  55                  60

<210> SEQ ID NO 22
<211> LENGTH: 64
<212> TYPE: PRT
<213> ORGANISM: macca mulatta

<400> SEQUENCE: 22

Val Ala Lys Lys Cys Ala Gly Cys Lys Asn Pro Ile Thr Gly Phe Gly
1               5                   10                  15

Lys Gly Ser Ser Val Val Ala Tyr Glu Gly Gln Ser Trp His Asp Tyr
            20                  25                  30

Cys Phe His Cys Lys Lys Cys Ser Val Asn Leu Ala Asn Lys Arg Phe
        35                  40                  45

Val Phe His Gln Glu Gln Val Tyr Cys Pro Asp Cys Ala Lys Lys Leu
    50                  55                  60

<210> SEQ ID NO 23
<211> LENGTH: 64
<212> TYPE: PRT
<213> ORGANISM: mus musculus

<400> SEQUENCE: 23

Val Ala Lys Lys Cys Ala Gly Cys Lys Asn Pro Ile Thr Gly Phe Gly
1               5                   10                  15

Lys Gly Ser Ser Val Val Ala Tyr Glu Gly Gln Ser Trp His Asp Tyr
            20                  25                  30

Cys Phe His Cys Lys Lys Cys Ser Val Asn Leu Ala Asn Lys Arg Phe
        35                  40                  45

Val Phe His Asn Glu Gln Val Tyr Cys Pro Asp Cys Ala Lys Lys Leu
    50                  55                  60

<210> SEQ ID NO 24
<211> LENGTH: 64
<212> TYPE: PRT
<213> ORGANISM: didelphimoorphia

<400> SEQUENCE: 24

Val Ala Lys Lys Cys Ala Gly Cys Lys Asn Pro Ile Thr Gly Phe Gly
1               5                   10                  15

Lys Gly Ser Ser Val Val Asn Tyr Glu Gly Gln Ser Trp His Asp Tyr
            20                  25                  30

Cys Phe His Cys Lys Lys Cys Ser Met Asn Leu Ala Asn Lys Arg Phe
        35                  40                  45

Val Cys His Asn Glu Gln Ile Tyr Cys Pro Asp Cys Ala Lys Lys Leu
    50                  55                  60

<210> SEQ ID NO 25
<211> LENGTH: 64
<212> TYPE: PRT
<213> ORGANISM: gallus gallus

<400> SEQUENCE: 25

Val Ala Lys Lys Cys Ala Gly Cys Lys Asn Pro Ile Thr Gly Phe Gly
1               5                   10                  15

Arg Gly Thr Ser Val Val Asn Tyr Glu Asp Glu Ser Trp His Asp Tyr
            20                  25                  30

Cys Phe Lys Cys Thr Lys Cys Ala Arg Gly Leu Ala Asn Lys Arg Phe
        35                  40                  45

Val Cys His Asn Gly Lys Ile Tyr Cys Ala Glu Cys Pro Lys Arg Leu
    50                  55                  60

<210> SEQ ID NO 26
<211> LENGTH: 64
<212> TYPE: PRT
<213> ORGANISM: Xenopus

<400> SEQUENCE: 26

Val Ala Lys Lys Cys Ala Gly Cys Asn Asn Pro Ile Thr Gly Phe Gly
1               5                   10                  15

Lys Gly Ser Asn Val Val Asn Tyr Glu Gly Asn Ser Trp His Glu Tyr
            20                  25                  30

Cys Phe Thr Cys Lys Lys Cys Ser Leu Asn Leu Ala Asn Lys Arg Phe
        35                  40                  45

Val Arg His Asn Glu Gln Val Tyr Cys Gln Asp Cys Ala Lys Lys Met
    50                  55                  60

<210> SEQ ID NO 27
<211> LENGTH: 64
<212> TYPE: PRT
<213> ORGANISM: danio rerio

<400> SEQUENCE: 27

Val Ala Lys Lys Cys Ser Gly Cys Gln Asn Pro Ile Thr Gly Phe Gly
1               5                   10                  15

Arg Gly Thr Asn Val Val Asn Tyr Glu Asp Lys Ser Trp His Glu Tyr
            20                  25                  30

Cys Phe Asn Cys Lys Lys Cys Ser Leu Ser Met Ala His Lys Arg Phe
        35                  40                  45

Val Ile Asn Gly Glu Asp Ile Tyr Cys Ser Asp Cys Ala Lys Lys Leu
    50                  55                  60

<210> SEQ ID NO 28
<211> LENGTH: 63
<212> TYPE: PRT
<213> ORGANISM: tetraodon

<400> SEQUENCE: 28

Val Ala Lys Lys Cys Ala Gly Cys Lys Asn Pro Ile Thr Gly Phe Gly
1               5                   10                  15

Lys Gly Ser Ser Val Val Ala Tyr Glu Gly Gln Ser Trp His Asp Tyr
            20                  25                  30

Cys Phe His Cys Lys Lys Cys Ser Val Asn Leu Ala Asn Lys Arg Phe
        35                  40                  45

```
Val Phe His Gln Glu Gln Val Tyr Cys Pro Asp Cys Gly Ser Asn
 50                  55                  60
```

<210> SEQ ID NO 29
<211> LENGTH: 25
<212> TYPE: DNA
<213> ORGANISM: homo sapiens

<400> SEQUENCE: 29
tccaacattg gaaatcacat ttcaa                                     25

<210> SEQ ID NO 30
<211> LENGTH: 24
<212> TYPE: DNA
<213> ORGANISM: homo sapiens

<400> SEQUENCE: 30
tcatcacaaa tagatgtttc acag                                      24

<210> SEQ ID NO 31
<211> LENGTH: 25
<212> TYPE: DNA
<213> ORGANISM: homo sapiens

<400> SEQUENCE: 31
gaggctataa ttctttaact ttggc                                     25

<210> SEQ ID NO 32
<211> LENGTH: 25
<212> TYPE: DNA
<213> ORGANISM: homo sapiens

<400> SEQUENCE: 32
ctctttccct ctttattcat gttac                                     25

<210> SEQ ID NO 33
<211> LENGTH: 21
<212> TYPE: DNA
<213> ORGANISM: homo sapiens

<400> SEQUENCE: 33
gctggcttta ttttaagagg a                                         21

<210> SEQ ID NO 34
<211> LENGTH: 20
<212> TYPE: DNA
<213> ORGANISM: homo sapiens

<400> SEQUENCE: 34
ggttttcagt ttcctgggta                                           20

<210> SEQ ID NO 35
<211> LENGTH: 24
<212> TYPE: DNA
<213> ORGANISM: homo sapiens

<400> SEQUENCE: 35
cgtttaccag ctcaaaatct caac                                      24

<210> SEQ ID NO 36
<211> LENGTH: 24
<212> TYPE: DNA
<213> ORGANISM: homo sapiens
<210> SEQ ID NO 37
<211> LENGTH: 25
<212> TYPE: DNA
<213> ORGANISM: homo sapiens

<400> SEQUENCE: 37
aaggttcctc cagtaacaga tttgg         25

<210> SEQ ID NO 38
<211> LENGTH: 25
<212> TYPE: DNA
<213> ORGANISM: homo sapiens

<400> SEQUENCE: 38
tatgctacat agtatgtcct cagac         25

<210> SEQ ID NO 39
<211> LENGTH: 280
<212> TYPE: PRT
<213> ORGANISM: homo sapiens

<400> SEQUENCE: 39

```
Met Ala Glu Lys Phe Asp Cys His Tyr Cys Arg Asp Pro Leu Gln Gly
1               5                   10                  15

Lys Lys Tyr Val Gln Lys Asp Gly His His Cys Cys Leu Lys Cys Phe
            20                  25                  30

Asp Lys Phe Cys Ala Asn Thr Cys Val Glu Cys Arg Lys Pro Ile Gly
        35                  40                  45

Ala Asp Ser Lys Glu Val His Tyr Lys Asn Arg Phe Trp His Asp Thr
    50                  55                  60

Cys Phe Arg Cys Ala Lys Cys Leu His Pro Leu Ala Asn Glu Thr Phe
65                  70                  75                  80

Val Ala Lys Asp Asn Lys Ile Leu Cys Asn Lys Cys Thr Thr Arg Glu
                85                  90                  95

Asp Ser Pro Lys Cys Lys Gly Cys Phe Lys Ala Ile Val Ala Gly Asp
            100                 105                 110

Gln Asn Val Glu Tyr Lys Gly Thr Val Trp His Lys Asp Cys Phe Thr
        115                 120                 125

Cys Ser Asn Cys Lys Gln Val Ile Gly Thr Gly Ser Phe Phe Pro Lys
    130                 135                 140

Gly Glu Asp Phe Tyr Cys Val Thr Cys His Glu Thr Lys Phe Ala Lys
145                 150                 155                 160

His Cys Val Lys Cys Asn Lys Ala Ile Thr Ser Gly Gly Ile Thr Tyr
                165                 170                 175

Gln Asp Gln Pro Trp His Ala Asp Cys Phe Val Cys Val Thr Cys Ser
            180                 185                 190

Lys Lys Leu Ala Gly Gln Arg Phe Thr Ala Val Glu Asp Gln Tyr Tyr
        195                 200                 205

Cys Val Asp Cys Tyr Lys Asn Phe Val Ala Lys Lys Cys Ala Gly Cys
    210                 215                 220

Lys Asn Pro Ile Thr Gly Phe Gly Lys Gly Ser Ser Val Val Ala Tyr
225                 230                 235                 240

Glu Gly Gln Ser Trp His Asp Tyr Cys Phe His Cys Lys Lys Cys Ser
```

```
                    245                 250                 255
Val Asn Leu Ala Asn Lys Arg Phe Val Phe His Gln Glu Gln Val Tyr
            260                 265                 270

Cys Pro Asp Cys Ala Lys Lys Leu
            275                 280

<210> SEQ ID NO 40
<211> LENGTH: 15
<212> TYPE: DNA
<213> ORGANISM: homo sapiens

<400> SEQUENCE: 40
ctggatgcaa gaacc                                                      15

<210> SEQ ID NO 41
<211> LENGTH: 15
<212> TYPE: DNA
<213> ORGANISM: homo sapiens

<400> SEQUENCE: 41
ctggatggaa gaacc                                                      15
```